United States Patent
Bregeon

(10) Patent No.: US 10,071,169 B2
(45) Date of Patent: Sep. 11, 2018

(54) ENZYMATIC CONJUGATION OF POLYPEPTIDES

(71) Applicant: Innate Pharma, Marseilles (FR)

(72) Inventor: Delphine Bregeon, Marseilles (FR)

(73) Assignee: INNATE PHARMA, Marseilles (FR)

(*) Notice: Subject to any disclaimer, the term of this patent is extended or adjusted under 35 U.S.C. 154(b) by 1 day.

(21) Appl. No.: 14/898,693

(22) PCT Filed: Jun. 20, 2014

(86) PCT No.: PCT/EP2014/063061
§ 371 (c)(1),
(2) Date: Dec. 15, 2015

(87) PCT Pub. No.: WO2014/202773
PCT Pub. Date: Dec. 24, 2014

(65) Prior Publication Data
US 2016/0114056 A1    Apr. 28, 2016

Related U.S. Application Data

(60) Provisional application No. 61/837,564, filed on Jun. 20, 2013.

(51) Int. Cl.
| | |
|---|---|
| *A61K 47/48* | (2006.01) |
| *A61K 38/05* | (2006.01) |
| *C07K 16/00* | (2006.01) |
| *C12P 21/00* | (2006.01) |

(52) U.S. Cl.
CPC ........ *A61K 47/48415* (2013.01); *A61K 38/05* (2013.01); *A61K 47/48384* (2013.01); *C07K 16/00* (2013.01); *C12P 21/005* (2013.01); *C07K 2317/14* (2013.01)

(58) Field of Classification Search
None
See application file for complete search history.

(56) References Cited

U.S. PATENT DOCUMENTS

| | | | |
|---|---|---|---|
| 4,741,900 A | 5/1988 | Alvarez et al. |
| 4,816,567 A | 3/1989 | Cabilly et al. |
| 5,156,956 A | 10/1992 | Motoki et al. |
| 5,225,539 A | 7/1993 | Winter |
| 5,229,275 A | 7/1993 | Goroff |
| 5,252,469 A | 10/1993 | Andou et al. |
| 5,530,101 A | 6/1996 | Queen et al. |
| 5,565,332 A | 10/1996 | Hoogenboom et al. |
| 5,567,610 A | 10/1996 | Borrebaeck et al. |
| 5,573,905 A | 11/1996 | Lerner et al. |
| 5,585,089 A | 12/1996 | Queen et al. |
| 5,693,761 A | 12/1997 | Queen et al. |
| 5,693,762 A | 12/1997 | Queen et al. |
| 5,712,120 A | 1/1998 | Rodriguez et al. |
| 5,714,350 A | 2/1998 | Co et al. |
| 5,731,183 A | 3/1998 | Kobayashi et al. |
| 5,736,356 A | 4/1998 | Sano et al. |
| 5,766,886 A | 6/1998 | Studnicka et al. |
| 5,770,196 A | 6/1998 | Studnicka |
| 5,777,085 A | 7/1998 | Co et al. |
| 5,821,123 A | 10/1998 | Studnicka |
| 5,821,337 A | 10/1998 | Carter et al. |
| 5,869,619 A | 2/1999 | Studnicka |
| 5,877,293 A | 3/1999 | Adair et al. |
| 5,886,152 A | 3/1999 | Nakatani et al. |
| 5,895,205 A | 4/1999 | Werner et al. |
| 5,929,212 A | 7/1999 | Jolliffe et al. |
| 6,054,297 A | 4/2000 | Carter et al. |
| 6,162,963 A | 12/2000 | Kucherlapati et al. |
| 6,180,370 B1 | 1/2001 | Queen et al. |
| 6,204,388 B1 | 3/2001 | Danishefsky et al. |
| 6,380,394 B1 | 4/2002 | Nicolaou et al. |
| 6,387,927 B1 | 5/2002 | Altmann et al. |
| 6,407,213 B1 | 6/2002 | Carter et al. |
| 6,548,640 B1 | 4/2003 | Winter |
| 6,632,927 B2 | 10/2003 | Adair et al. |
| 6,639,055 B1 | 10/2003 | Carter et al. |
| 6,750,325 B1 | 6/2004 | Jolliffe et al. |
| 6,797,492 B2 | 9/2004 | Daugherty et al. |
| 6,881,557 B2 | 4/2005 | Foote |
| 7,087,409 B2 | 8/2006 | Barbas, III et al. |
| 7,090,843 B1 | 8/2006 | Francisco et al. |
| 7,117,096 B2 | 10/2006 | Luo et al. |
| 7,135,174 B2 | 11/2006 | Corvalan et al. |
| 7,338,933 B2 | 3/2008 | DeFrees et al. |

(Continued)

FOREIGN PATENT DOCUMENTS

| | | |
|---|---|---|
| DE | 19907588 A1 | 8/2000 |
| EP | 0555649 A2 | 8/1993 |

(Continued)

OTHER PUBLICATIONS

Alley et al (Current Opinion in chemical Biology, 2010, vol. 14, pp. 529-537).*
MGT Scientific Chart (downloaded from the web Aug. 2017).*
Agard et al., "A Strain-Promoted [3+2] Azide-Alkyne Cycloaddition for Covalent Modification of Biomolecules in Living Systems", J Am Chem Soc Comm. (2004) 126:15046-15047.
Chari, Ravi V.J., "Targeted Cancer Therapy: Conferring Specificity to Cytotoxic Drugs", Acc of Chem Res, (Jan. 2008) 41(1):98-107.
U.S. Response to Office Action filed May 23, 2016 in U.S. Appl. No. 13/725,382, filed Dec. 21, 2012.
U.S. Office Action dated Aug. 8, 2016 in U.S. Appl. No. 13/725,382, filed Dec. 21, 2012.

(Continued)

*Primary Examiner* — Karen A Canella
(74) *Attorney, Agent, or Firm* — Knobbe Martens Olson & Bear LLP

(57) ABSTRACT

One embodiment relates to methods for the enzymatic functionalization of immunoglobulins, in particular with drugs. Also disclosed herein are linking reagents, functionalized antibodies, pharmaceutical compositions, and method of treating disease and/or conditions.

27 Claims, 4 Drawing Sheets
Specification includes a Sequence Listing.

(56) References Cited

U.S. PATENT DOCUMENTS

| | | |
|---|---|---|
| 7,378,091 B2 | 5/2008 | Gudas et al. |
| 7,393,648 B2 | 7/2008 | Rother et al. |
| 7,498,298 B2 | 3/2009 | Doronina et al. |
| 7,657,380 B2 | 2/2010 | Lazar et al. |
| 7,659,241 B2 | 2/2010 | Senter et al. |
| 7,763,736 B2 | 7/2010 | Sharpless et al. |
| 7,807,619 B2 | 10/2010 | Bertozzi et al. |
| 7,981,843 B2 | 7/2011 | Flynn et al. |
| 8,133,515 B2 | 3/2012 | Boons et al. |
| 9,340,615 B2 | 5/2016 | Maeda et al. |
| 9,427,478 B2 | 8/2016 | Bregeon et al. |
| 9,676,871 B2 | 6/2017 | Strop et al. |
| 9,717,803 B2 | 8/2017 | Bregeon et al. |
| 9,764,038 B2 | 9/2017 | Dennler et al. |
| 2002/0034765 A1 | 3/2002 | Daugherty et al. |
| 2002/0052028 A1 | 5/2002 | Santi et al. |
| 2002/0058286 A1 | 5/2002 | Danishefsky et al. |
| 2002/0062030 A1 | 5/2002 | White et al. |
| 2002/0102208 A1 | 8/2002 | Chinn et al. |
| 2002/0161201 A1 | 10/2002 | Filpula et al. |
| 2003/0153043 A1 | 8/2003 | Carr et al. |
| 2004/0253645 A1 | 12/2004 | Daugherty et al. |
| 2005/0026263 A1 | 2/2005 | Meares et al. |
| 2005/0238646 A1 | 10/2005 | Ledbetter et al. |
| 2005/0238649 A1 | 10/2005 | Doronina et al. |
| 2005/0256030 A1 | 11/2005 | Feng |
| 2006/0073137 A1 | 4/2006 | Adair et al. |
| 2006/0116422 A1 | 6/2006 | de Groot et al. |
| 2007/0122408 A1 | 5/2007 | Barbas, III et al. |
| 2008/0038260 A1 | 2/2008 | Ponath et al. |
| 2009/0028856 A1 | 1/2009 | Chen et al. |
| 2010/0004431 A1 | 1/2010 | Bernett et al. |
| 2011/0184147 A1 | 7/2011 | Kamiya et al. |
| 2011/0256157 A1 | 10/2011 | Howard et al. |
| 2011/0305631 A1 | 12/2011 | Govindan et al. |
| 2012/0322686 A1 | 12/2012 | Lyon et al. |
| 2013/0122020 A1 | 5/2013 | Liu et al. |
| 2013/0189287 A1 | 7/2013 | Bregeon et al. |
| 2013/0230543 A1* | 9/2013 | Pons ............ A61K 47/48369 424/178.1 |
| 2014/0088089 A1 | 3/2014 | Chari |
| 2014/0356385 A1 | 12/2014 | Dennler et al. |
| 2015/0284713 A1 | 10/2015 | Fischer et al. |
| 2015/0346195 A1 | 12/2015 | Belmant et al. |
| 2016/0022833 A1 | 1/2016 | Bregeon et al. |
| 2016/0331842 A1 | 11/2016 | Bregeon et al. |
| 2017/0313787 A1 | 11/2017 | Strop et al. |

FOREIGN PATENT DOCUMENTS

| | | |
|---|---|---|
| EP | 1859811 A1 | 11/2007 |
| JP | 2003199569 A | 7/2003 |
| WO | WO 1992/02190 | 1/1992 |
| WO | WO 1992/11018 | 7/1992 |
| WO | WO 1992/22583 | 12/1992 |
| WO | WO 1993/10102 | 5/1993 |
| WO | WO 1996/06931 | 3/1996 |
| WO | WO 1996/22366 | 7/1996 |
| WO | WO 1998/25929 A1 | 6/1998 |
| WO | WO 1999/02514 A2 | 1/1999 |
| WO | WO 1999/07692 A2 | 2/1999 |
| WO | WO 1999/58534 A2 | 11/1999 |
| WO | WO 1999/67252 A2 | 12/1999 |
| WO | WO 1999/67253 A2 | 12/1999 |
| WO | WO 2000/000485 A1 | 1/2000 |
| WO | WO 2000/037473 A1 | 6/2000 |
| WO | WO 2000/049019 A2 | 8/2000 |
| WO | WO 2000/049020 A2 | 8/2000 |
| WO | WO 2000/049021 A2 | 8/2000 |
| WO | WO 2000/057874 A1 | 10/2000 |
| WO | WO 2000/066589 A1 | 11/2000 |
| WO | WO 2000/071521 A1 | 11/2000 |
| WO | WO 2001/027308 A2 | 4/2001 |
| WO | WO 2001/064650 A2 | 9/2001 |
| WO | WO 2001/070716 A1 | 9/2001 |
| WO | WO 2001/073103 A2 | 10/2001 |
| WO | WO 2001/081342 A2 | 11/2001 |
| WO | WO 2001/092255 A2 | 12/2001 |
| WO | WO 2002/008440 A2 | 1/2002 |
| WO | WO 2002/014323 A2 | 2/2002 |
| WO | WO 2002/030356 A2 | 4/2002 |
| WO | WO 2002/032844 A2 | 4/2002 |
| WO | WO 2002/080846 A2 | 10/2002 |
| WO | WO 2002/083180 A1 | 10/2002 |
| WO | WO 2003/074053 A1 | 9/2003 |
| WO | WO 2004/014919 A1 | 2/2004 |
| WO | WO 2004/043493 A1 | 5/2004 |
| WO | WO 2004/043880 A2 | 5/2004 |
| WO | WO 2005/040219 A1 | 5/2005 |
| WO | WO 2005/070468 A2 | 8/2005 |
| WO | WO 2005/085251 A1 | 9/2005 |
| WO | WO 2007/008603 A1 | 1/2007 |
| WO | WO 2007/008848 A2 | 1/2007 |
| WO | WO 2007/020290 A1 | 2/2007 |
| WO | WO 2008/017122 A1 | 2/2008 |
| WO | WO 2008/102008 A1 | 8/2008 |
| WO | WO 2009/067663 A1 | 5/2009 |
| WO | WO 2009/105969 A1 | 9/2009 |
| WO | WO 2010/115630 A1 | 10/2010 |
| WO | WO 2010/136598 A1 | 12/2010 |
| WO | WO 2011/023883 A1 | 3/2011 |
| WO | WO 2011/136645 A1 | 3/2011 |
| WO | WO 2011/085523 A1 | 7/2011 |
| WO | WO 2011/120053 A1 | 9/2011 |
| WO | WO 2011/130616 A1 | 10/2011 |
| WO | WO 2012/041504 A1 | 4/2012 |
| WO | WO 2012/059882 A2 | 5/2012 |
| WO | WO 2012/112687 A1 | 8/2012 |
| WO | WO 2013/092983 A2 | 6/2013 |
| WO | WO 2013/092998 A1 | 6/2013 |
| WO | WO 2013/177481 A1 | 11/2013 |
| WO | WO 2014/009426 A1 | 1/2014 |
| WO | WO 2014/072482 A1 | 5/2014 |
| WO | WO 2014/140300 A1 | 9/2014 |

OTHER PUBLICATIONS

U.S. Response to Office Action filed Nov. 9, 2016 in U.S. Appl. No. 13/725,382, filed Dec. 21, 2012.

U.S. Response to Office Action filed Mar. 25, 2016 in U.S. Appl. No. 14/367,840, filed Jun. 20, 2014.

U.S. Office Action dated Jun. 17, 2016 in U.S. Appl. No. 14/367,840, filed Jun. 20, 2014.

U.S. Response to Office Action filed Nov. 14, 2016 in U.S. Appl. No. 14/367,840, filed Jun. 20, 2014.

U.S. Office Action dated Feb. 11, 2016 in U.S. Appl. No. 14/582,040, filed Dec. 23, 2014.

Response to Office Action filed Feb. 29, 2016 in U.S. Appl. No. 14/582,040, filed Dec. 23, 2014.

U.S. Notice of Allowance dated Jun. 6, 2016 in U.S. Appl. No. 14/582,040, filed Dec. 23, 2014.

U.S. Office Action dated Aug. 17, 2016 in U.S. Appl. No. 14/414,432, filed Jan. 12, 2015.

U.S. Response to Office Action filed Nov. 17, 2016 in U.S. Appl. No. 14/414,432, filed Jan. 12, 2015.

U.S. Response dated May 2, 2016 in U.S. Appl. No. 13/883,535, filed May 3, 2013.

U.S. Office Action dated Jul. 5, 2016 in U.S. Appl. No. 13/883,535, filed May 3, 2013.

U.S. Response dated Sep. 1, 2016 in U.S. Appl. No. 13/883,535, filed May 3, 2013.

Altschul et al., "Gapped BLAST and PSI-BLAST: A new generation of protein database search programs", Nucl Acids Res. (1997) 25(17): 3389-3402.

Altschul et al., "Basic Local Alignment Search Tool", J Mol Biol. (1990) 215:403-410.

Amersham Biosciences, Antibody Purification Handbook, (2002) Publication No. 18-1037-46 Edition AC, 112 pages.

Amsberry et al., "The Lactonization of 2'-Hydroxyhydrocinnamic Acid Amides: A Potential Prodrug of Amines", J. Org Chem (Apr. 1990) 55:5867-5877.

(56) References Cited

OTHER PUBLICATIONS

Ando et al., "Purification and Characteristics of a Novel Transglutaminase Derived from Microorganisms", Agric Biol Chem. (1989) 53(10):2613-2617.
Ausubel et al. (Eds.) Current Protocols in Molecular Biology (1993) John Wiley & Sons, Inc., Table of Contents, 15 pages.
Baeuerle et al., "Bispecific T-cell engaging antibodies for cancer therapy", Cancer Res. (2009) 69(12):4941-4944.
Bernhard et al., "Cysteine analogs of recombinant barley ribosome inactivating protein form antibody conjugates with enhanced stability and potency in vitro", Bioconjugate Chem., (1994) 5(2):126-132.
Brabez et al., "Design, synthesis and biological studies of efficient multivalent melanotropin ligands: tools towards melanoma diagnosis and treatment", J Med Chem. (2011) 54(20):7375-7384.
Carillo et al., "The Multiple Sequence Alignment Problem in Biology", Siam J. Appl Math. (1988) 48(5):1073-1082.
Carter et al., "Improved oligonucleotide site-directed mutagenesis using M13 vectors", Nucl Acids Res. (May 1985) 13(12):4431-4443.
Carter et al., "Humanization of an anti-p185HER2 antibody for human cancer therapy", Proc Natl Acad Sci. USA (1992) 89:4285-4289.
Chapman, Andrew P., "PEGylated antibodies and antibody fragments for improved therapy: a review", Advan Drug Del Rev. (Jan. 2002) 54:531-545.
Chothia et al., "Canonical Structures for the Hypervariable Regions of Immunoglobulins", J Mol Biol. (1987) 196:901-917.
Connolly et al., "In Vivo Inhibition of Fas Ligand-Mediated Killing by TR6, a Fas Ligand Decoy Receptor", J Pharmacol Exp Ther. (Jan. 2001) 298(1):25-33.
De Pascalis et al., "Grafting of "Abbreviated" Complementarity-Determining Regions Containing Specificity-Determining Residues Essential for Ligand Contact to Engineer a Less Immunogenic Humanized Monoclonal Antibody", J Immunol. (2002) 169(6):3076-3084.
Dennler et al., Transglutaminase-based chemo-enzymatic conjugation approach yields homogeneous antibody-drug conjugates. Bioconjugate Chemistry, (2014) 25(3):569-578.
Devereux et al., "A comprehensive set of sequence analysis programs for the VAX" Nucl Acids Res. (1984) 12(1):387-395.
Doronina et al., "Development of potent monoclonal antibody Auristatin conjugates for cancer therapy", Nat Biotech. (2003) 21(7):778-784 & Erratum Nat Biotech. (2003)21(8):941.
Doronina et al., "Enhanced activity of monomethylauristatin F through Monoclonal Antibody Delivery", Bioconjugate Chem. (2006) 17(1):114-124.
Dosio et al., "Immunotoxins and Anticancer Drug Conjugate Assemblies: The Role of the Linkage between Components", Toxins (2011) 3:848-883.
Edelaman et al., "The Covalent Structure of an Entire γG Immunoglobulin Molecule", Proc Natl Acad. USA, (1969) 63:78-85.
Folk et al., "Polyamines as Physiological Substrates for Transglutaminases", J. Biol. Chem. (Apr. 1980) 255(8):3695-3700.
Genbank Reference Sequence NM_024003.2; "Homo sapiens L1 cell adhesion molecule (L1CAM), transcript variant 2, mRNA", May 4, 2013; 8 pages.
Genbank Reference Sequence NM_024003.3; "Homo sapiens L1 cell adhesion molecule (L1CAM), transcript variant 2, mRNA", May 26, 2013; 10 pages.
Genbank Reference Sequence NM_0764493.1; "Neural cell adhesion molecule L1 isoform 2 precursor [Homo sapiens]", May 26, 2014; 6 pages.
Golay et al., "Mechanism of action of therapeutic monoclonal antibodies: Promises and pitfalls of in vitro and in vivo assays", Arch Biochem Biophys (2012) 526:146-153.
Gorman et al., "Transglutaminase Amine Substrates for Photochemical Labeling and Cleavable Cross-linking of Proteins", J Biol Chem. (1980) 255(3):1175-1180.
Green et al., "Antigen-specific human monoclonal antibodies from mice engineered with human Ig heavy and light chain YACs", Nature Gen. (1994) 7:13-21.
Gregson et al., "Linker Length Modules DNA Cross-Linking Reactivity and Cytotoxic Potency of C8/C8' Ether-linked C2-exo-Unsaturated Pyrrolo[2,1-c][1,4]benzodiazepine (PBD) Dimers", J Med Chem (2004) 47:1161-1174.
Gribskov et al., (Eds.) Sequence Analysis Primer; Stockton Press (1991); Table of Contents, 7 pages.
Griffin et al., (Eds.) Methods in Molecular Biology-24: Computer Analysis of Sequence Data; Part I & II; Humana Press, New Jersey (1994) Tables of Contents, 8 pages.
Griffiths et al., "Human anti-self antibodies with high specificity from phage display libraries", EMBO J. (1993) 12(2):725-734.
Griffiths et al., "Isolation of high affinity human antibodies directly from large synthetic repertoires", EMBO J. (1994) 13(14):3245-3260.
Grünberg et al. 2013. DOTA-functionalized polylysine: A high number of DOTA chelates positively influences the biodistribution of enzymatic conjugated anti-tumor antibody chCE7agl. PLOS ONE, 8(4):e60350.
Hamblett et al., "Effects of Drug Loading on the Antitumor Activity of a Monoclonal Antibody Drug Conjugate", Clin Cancer Res. (Oct. 2004) 10:7063-7070.
Harlow et al., (Eds.), Antibodies—A Laboratory Manual; Table of Contents, Cold Spring Harbor Laboratory Press, Cold Spring Harbor, NY (1988) TOC; 9 pages.
Hay et al., "A 2-nitroimidazole carbamate prodrug of 5-amino-1-(Chloromethyl)-3-[(5,6,7-Trimethoxyindol-2-YL)Carbonyl]-1,2-dihydro-3H-Benz[e]indole (amino-SECO-CBI-TMI) for use with ADEPT and GDEPT", Bioorg Med Chem Lttrs. (Jun. 1999) 9:2237-2242.
Hay et al., "Clinical development success rates for investigational drugs", Nat Biotech. (Jan. 2014) 32(1):40-51.
Higuchi, Russell "Recombinant PCR" Chapter 22 in Part II of PCR Protocols, A Guide to Methods and Applications [Innis et al. (Eds.)], Academic Press, (1990) pp. 177-183.
Ho et al. Site-directed Mutagenesis by Overlap Extension Using the Polymerase Chain Reaction. Gene (1989) 77(1):51-59.
Holliger et al., "Engineered antibody fragments and the rise of single domains", Nature Biotech. (2005) 23(9):1126-1136.
Hu et al., "Rational design of transglutaminase substrate peptides for rapid enzymatic formation of hydrogels", J Am Chem Soc. (Nov. 2003) 125(47):14298-14299.
Ill et al., "Design and construction of a hybrid immunoglobulin domain with properties of both heavy and light chain variable regions", Prot Engineer. (1997) 10(8):949-957.
Ito et al., "A General Method for Introducing a Series of Mutations into Cloned DNA Using the Polymerase Chain Reaction", Gene (Nov. 1991) 102(1):67-70.
Jackman et al., "Development of a two-part strategy to identify a therapeutic human bispecific antibody that inhibits IgE receptor signaling", J Biol Chem. (2010) 285(27):20850-20859.
Jakobovits et al., "Germ-line transmission and expression of a human-derived yeast artificial chromosome", Nature (1993) 362:255-258.
Jeffrey et al., "Development and Properties of beta-Glucuronide Linkers for Monoclonal Antibody-Drug Conjugates", Bioconj Chem. (2006) 17:831-840.
Jeger. Site-Specific Conjugation of Tumour-Targeting Antibodies Using Transglutaminase. Dissertation. ETH Zurich: University of Basel (2009) 1-135.
Jeger et al., "Site-Specific and Stoichiometric Modification of Antibodies by Bacterial Transglutaminase", Angew Chem Int Ed. (2010) 49(51):9995-9997.
Jeger et al., "Site-specific and stoichiometric modification of antibodies by bacterial transglutaminase", Supporting Information. Angewandte Chemie International Edition, Wiley VCH, (2010) 49(51): 46 pages.
Jones et al., "Replacing the complementarity-determining regions in a human antibody with those from a mouse", Nature (1986) 321:522-525.

(56) References Cited

OTHER PUBLICATIONS

Josten et al., "Use of microbial transglutaminase for the enzymatic biotinylation of antibodies", J Immunol Meth. (2000) 240:47-54.
Jubala et al., "CD20 Expression in Normal Canine B Cells and in Canine non-Hodgkin Lymphoma", Vet Pathol. (2005) 42:368-476.
Junutula et al., "Site-specific conjugation of a cytotoxic drug to an antibody improves the therapeutic index", Nature Biotech (2008) 26(8):925-932.
Kabat et al., (Eds.) Sequences of Proteins of Immunological Interest, 5th Edition; (1991) Table of Contents; 11 pages.
Kamal et al., "Synthesis of 1,2,3-triazole-linked pyrrolobenzodiazepine conjugates employing 'click' chemistry: DNA-binding affinity and anticancer activity", Bioorg Med Chem Lett. (Feb. 2008) 18(4):1468-1473.
Kämpfer et al., "A numerical classification of the genera *Streptomyces* and *Streptoverticillium* using miniaturized physiological tests", J Gen Microbiol. (Feb. 1991) 137:1831-1891.
Kajiwara et al., "Expression of L1 Cell Adhesion Molecule and Morphologic Features at the Invasive Front of Colorectal Cancer", Anat Pathol. (2011) 136(1):138-144.
Kamiya et al., "S-Peptide as a Potent Peptidyl Linker for Protein Cross-Linking by Microbial Transglutaminase from *Streptomyces mobaraensis*", Bioconj Chem. (2003) 14:351-357.
Kamiya et al., "Site-specific cross-linking of functional proteins by transglutamination", Enzy Micro Tech. (2003) 33:492-496.
Kingsbury et al., "A Novel Peptide Delivery System Involving Peptidase Activated Prodrugs as Antimicrobial Agents. Synthesis and Biological Activity of Peptidyl Derivatives of 5-Fluorouracil" J Med Chem. (Apr. 1984) 27:1447-1451.
Knappik et al., "Fully Synthetic Human Combinatorial Antibody Libraries (HuCAL) Based on Modular Consensus Frameworks and CDRs Randomized with Trinucleotides", J Mol Biol. (2000) 296:57-86.
Knogler et al., "Copper-67 Radioimmunotherapy and Growth Inhibition by Anti-L1-Cell Adhesion Molecule Monoclonal Antibodies in a Therapy Model of Ovarian Cancer Metastasis", Clin Cancer Res (2007) 13(2):603-611.
Kuil et al., "ITAM-derived phosphopeptide-containing dendrimers as multivalent ligands for Syk tandem SH2 domain", Org Biomol Chem. (2009) 7:4088-4094.
Kunkel, Thomas A., "Rapid and efficient site-specific mutagenesis without phenotypic selection", Proc Natl Acad Sci USA (Jan. 1985) 82:488-492.
Lesk, Arthur M. (Ed.) Computational Molecular Biology, Oxford University Press (1988); Table of Contents; 4 pages.
Lhospice et al., "Cite-specific conjugation of monomethyl auristatin E to Anti-CD30 antibodies improves their pharmacokinetics and therapeutic index in rodent models", Mol Pharmaceutics (2015) 12:1863-1871.
Lin et al., "Transglutaminase-catalyzed site-specific conjugation of small-molecule probes to proteins in vitro and on the surface of living cells", J Am Chem Soc. (2006) 128(14):4542-4543 (7pages).
Liu et al., "Identification of Active Site Residues in the "GyrA" Half of Yeast DNA Topoisomerase II", J Biol Chem. (Aug. 1998) 273(32):20252-20260.
Lonberg et al., "Antigen-specific human antibodies from mice comprising four distinct genetic modifications", Nature (1994) 368:856-859.
Lonberg, Nils, "Human antibodies from transgenic animals", Nature Biotech. (2005) 211, 123(9):1117-1125.
Lorand et al., "Specificity of Guinea Pig Liver Transglutaminase for Amine Substrates", Biochem. (1979) 18(9):1756-1765.
Lorand et al., "Transglutaminases: Cross-linking enzymes with pleiotropic functions", Nature (Feb. 2003) 4:140-156.
Lyon et al., "Conjugation of Anticancer Drugs through Endogenous Monoclonal Antibody Cysteine Residues", Meth Enzymol. (2012) 502:123-138.
Maeda et al., "Susceptibility of human T-cell leukemia virus type I-infected cells to humanized anti-CD30 monoclonal antibodies in vitro and in vivo", Cancer Sci. (2010) 101(1):224-230.
McCafferty et al., "Phage antibodies: Filamentous phage displaying antibody variable domains", Nature (1990) 348:552-554.
Mindt et al., Modification of Different IgG1 Antibodies Glutamine and Lysine Using Bacterial and Human Tissue Transglutaminase. Bioconjug Chem. (2008) 19(1):271-278.
Morrison et al., "Chimeric human antibody molecules: Mouse antigen-binding domains with human constant region domains", Proc Natl Acad Sci. USA (1984) 81:6851-6855.
Moses et al., "The growing applications of click chemistry", Chem Soc Rev. (Aug. 2007) 36(8):1249-1262.
Murthy et al., "Residue Gln-30 of Human Erythrocyte Anion Transporter is a Prime Site for Reaction with Intrinsic Transglutaminase" J Biolog Chem. (Sep. 1994) 269(36):22907-22911.
Murthy et al., "Selectivity in the Post-Translational, Transglutaminase-dependent Acylation of Lysine Residues", Biochem. (Feb. 2009) 48:2654-2660.
Nilsson et al., A synthetic IgG-binding domain based on stapylococcal protein A. Protein Eng. (1987) 1(2):107-113.
Pearson, William R., "Rapid and Sensitive Sequence Comparison with FASTP and FASTA", Meth Enzymol. (1990) 183(5):63-98.
Pearson, William R., "Flexible sequence similarity searching with the FASTA3 program package", Methods Mol Biol. (2000) 132:185-219.
Plagmann et al., "Transglutaminase-catalyzed covalent multimerization of camelidae anti-human TNF single domain antibodies improves neutralizing activity", J Biotech. (2009) 142:170-178.
Presta, Leonard G., "Antibody engineering", Curr Opin Struct Biol. (1992) 2:593-596.
Presta et al., "Humanization of an Antibody Directed Against IgE", J Immunol. (1993) 151(5):2623-2632.
Riechmann et al., "Reshaping human antibodies for therapy", Nature (1988) 332:323-327.
Rodrigues et al., "Synthesis and β-lactamase-mediated activation of a cephalosporin-taxol prodrug", Chem Biol. (Apr. 1995) 2:223-227.
Roguska et al., "Humanization of murine monoclonal antibodies through variable domain resurfacing", Proc Natl Acad Sci. (1994) 91:969-973.
Sambrook et al., (Eds.) Molecular Cloning—A Laboratory Manual, [2nd Edition]; Cold Spring Harbor Laboratory Press, NY; (1989) Table of Contents, 30 pages.
Sambrook et al., (Eds.) Molecular Cloning—A Laboratory Manual, [3rd Edition]; Cold Spring Harbor Laboratory Press, NY; (2001); Table of Contents, 18 pages.
Sazinsky et al., "Aglycosylated immunoglobulin G1 variants productively engage activating Fc receptors" PNAS (2008) 105(51):20167-20172.
Sims et al., "A Humanized CD18 Antibody can block Function without Cell Destruction", J Immunol. (1993) 151:2296-2308.
Smith, Douglas W. (Ed.), Biocomputing—Informatics and Genome Projects, Academic Press, Inc. (1993) Table of Contents, 7 pages.
Stancovski et al., "Mechanistic aspects of the opposing effects of monoclonal antibodies to the ERBB2 receptor on tumor growth", Proc Natl Acad Sci USA. (Oct. 1991) 88(19):8691-8695.
Sung et al., "Functional glass surface displaying a glutamyl donor substrate for transglutaminase-mediated protein immobilization", Biotech J. (2010) (5):456-462.
Suzuki et al., Glycopinion Mini-Review: N-Glycosylation/Deglycosylation as a Mechanism for the Post-Translational Modification/Remodification of Proteins. Glycoconjug J. (1995) 12:183-193.
Takazawa et al., Enzymatic Labeling of a Single Chain Variable Fragment of an Antibody With Alkaline Phosphates by Microbial Transglutaminase. Biotech Engin. (2004) 86(4):399-404.
Tan et al., "Superhumanized" Antibodies: Reduction of Immunogenic Potential by Complementarity-Determining Region Grafting with Human Germline Sequences: Application to an Anti-CD28. J Immunol. (2002) 169:1119-1125.
Tomlinson et al., The Repertoire of Human Germline VH Sequences Reveals about Fifty Groups of VH Segments with Different Hypervariable Loops. J Mol Biol. (1992) 227:776-798.

(56) References Cited

OTHER PUBLICATIONS

Uhlén et al., Complete Sequence of the Staphylococcal Gene Encoding Protein A—A Gene Evolved Through Multiple Duplications. J Biol Chem. (1984) 259(3):1695-1702.
Vallette et al., Construction of Mutant and Chimeric Genes Using the Polymerase Chain Reaction. Nuc Acids Res. (Jan. 1989) 17(2):723-733.
Verhoeyen et al., Reshaping Human Antibodies: Grafting an Antilysozyme Activity. Science (1988) 239:1534-1536.
Von Heinje, Gunnar [Ed.] "Sequence Analysis in Molecular Biology—Treasure Trove or Trivial Pursuit", 1987, Academic Press [TOC Only].
Wakankar et al., Analytical Methods for Physicochemical Characterization of Antibody Drug Conjugates. mAbs, Landes Biosci. (Mar./Apr. 2011) 3(2):161-172.
Wängler et al., "Antibody-Dendrimer Conjugates: The Number, Not the Size of the Dendrimers, Determines the Immunoreactivity" Bioconjugate Chem. (2008) (19)4:813-820.
Ward et al., Binding Activities of a Repertoire of Single Immunoglobulin Variable Domains Secreted From *Escherichia coli*. Nature (1989) 341:544-546.
Wells et al., Cassette Mutagenesis: An Efficient Method for Generation of Multiple Mutations at Defined Sites. Gene (Jan. 1985) 34(2-3):315-323.
Xu et al., "Characterization of intact antibody-drug conjugates from plasma/serum in vivo by affinity capture capillary liquid chromatography mass spectrometry", Anal Biochem. (2011) 412(1): 56-66.
Yu et al., "Interaction between Bevacizumab and Murine VEGF-A: A Reassessment", Invest Ophtalmol Vis Sci. (Feb. 2008); 49(2):522-527.
Yurkovetskiy et al., Synthesis of a Macromolecular Camptothecin Conjugate with Dual Phase Drug Release. Mol Pharm. (Jun. 2004) 1(5):375-382.
Zoller et al., "Oligonuoleotide-directed mutagenesis using M13-derived vectors: an efficient and general procedure for the production of point mutations in any fragment of DNA", Nucl Acids Res. (Aug. 1982) 10(20):6487-6500.
Zoller et al., "Oligonccleotide-directed mutagenesis of DNA fragments cloned into M13 vectors", Methods Enzymol. (1983) 100:468-500.
International Search Report dated Apr. 23, 2013 for International Application No. PCT/EP2012/076631 filed Dec. 21, 2012.
International Search Report dated Feb. 5, 2014 for International Application No. PCT/EP2012/076606 filed Dec. 21, 2012.
International Search Report and Written Opinion dated Sep. 24, 2014 for International Application No. PCT/EP2014/063064 filed Jun. 20, 2014, 16 pages.
International Search Report dated Jan. 31, 2014 for International Application No. PCT/EP2013/064605 filed Jul. 10, 2013.
International Search Report dated Apr. 15, 2014 for International Application No. PCT/EP2013/073428 filed Nov. 8, 2013.
International Search Report dated Jun. 25, 2014 for International Application No. PCT/EP2014/055140 filed Mar. 14, 2014.
U.S. Appl. No. 61/410,840, filed Nov. 5, 2010.
U.S. Appl. No. 61/553,917, filed Oct. 31, 2011.
U.S. Appl. No. 61/579,908, filed Dec. 23, 2011.
U.S. Appl. No. 61/661,569, filed Jun. 19, 2012.
U.S. Appl. No. 61/671,122, filed Jul. 13, 2012.
U.S. Appl. No. 61/671,128, filed Jul. 13, 2012.
U.S. Appl. No. 61/837,932, filed Jun. 21, 2013.
U.S. Office Action dated Feb. 27, 2015 in U.S. Appl. No. 13/725,382, filed Dec. 21, 2012.
U.S. Response to Office Action filed May 28, 2015 in U.S. Appl. No. 13/725,382, filed Dec. 21, 2012.
U.S. Office Action dated Aug. 13, 2015 in U.S. Appl. No. 13/725,382, filed Dec. 21, 2012.
U.S. Response to Office Action filed Dec. 11, 2015 in U.S. Appl. No. 13/725,382, filed Dec. 21, 2012.
U.S. Office Action dated Apr. 23, 2015 in U.S. Appl. No. 14/582,040, filed Dec. 23, 2014.
U.S. Response to Office Action filed May 20, 2015 in U.S. Appl. No. 14/582,040, filed Dec. 23, 2014.
U.S. Pre-Interview Communication dated Jul. 2, 2015 in U.S. Appl. No. 14/582,040, filed Dec. 23, 2014.
U.S. Response to Pre-Interview Communication filed Jul. 31, 2015 in U.S. Appl. No. 14/582,040, filed Dec. 23, 2014.
U.S. Office Action dated Oct. 8, 2015 in U.S. Appl. No. 14/582,040, filed Dec. 23, 2014.
Response to Office Action filed Dec. 8, 2015 in U.S. Appl. No. 14/582,040, filed Dec. 23, 2014.
U.S. Preliminary Amendment dated May 3, 2013 in U.S. Appl. No. 13/883,535, filed May 3, 2013.
U.S. Office Action dated Dec. 19, 2014 in U.S. Appl. No. 13/883,535, filed May 3, 2013.
U.S. Second Preliminary Amendment dated Feb. 17, 2015 in U.S. Appl. No. 13/883,535, filed May 3, 2013.
U.S. Office Action dated Sep. 16, 2015 in U.S. Appl. No. 13/883,535, filed May 3, 2013.
U.S. Response dated Nov. 16, 2015 in U.S. Appl. No. 13/883,535, filed May 3, 2013.
U.S. Office Action dated Dec. 30, 2015 in U.S. Appl. No. 13/883,535, filed May 3, 2013.
U.S. Office Action dated Jan. 29, 2016 in U.S. Appl. No. 14/367,840, filed Jun. 20, 2014.
Dennler et al., Enzymatic antibody modification by bacterial transglutaminase. Bioconjugate Chemistry, (Jan. 2013) 1045:205-215.
Strop et al., "Location Matters: Site of Conjugation Modulates Stability and Pharmacokinetics of Antibody Drug Conjugates", Chem Biol. (Feb. 2013) 20(2):161-167.
International Search Report and Written Opinion of the International Searching Authority dated Aug. 20, 2014 for International Application No. PCT/EP2014/063061 filed Jun. 20, 2014.
Starling et al., "In vivo antitumor activity of a panel of four monoclonal antibody-vinca alkaloid immunoconjugates which bind to three distinct epitopes of carcinoembryonic antigen", Bioconjug Chem. (1992) 3(4):315-322.
U.S. Notice of Allowance dated Mar. 28, 2017 in U.S. Appl. No. 13/725,382, filed Dec. 21, 2012.
U.S. Notice of Allowability/Examiner's Amendment dated Apr. 28, 2017 in U.S. Appl. No. 13/725,382, filed Dec. 21, 2012.
U.S. Office Action dated Jan. 31, 2017 in U.S. Appl. No. 14/367,840, filed Jun. 20, 2014.
U.S. Response to Office Action filed Apr. 28, 2017 in U.S. Appl. No. 14/367,840, filed Jun. 20, 2014.
U.S. Notice of Allowance dated May 16, 2017 in U.S. Appl. No. 14/367,840, filed Jun. 20, 2014.
Preliminary Amendment dated Jan. 9, 2017 in U.S. Appl. No. 15/214,331, filed Jul. 19, 2016.
U.S. Office Action dated Mar. 31, 2017 in U.S. Appl. No. 14/414,432, filed Jan. 12, 2015.
U.S. Office Action dated Feb. 28, 2017 in U.S. Appl. No. 14/441,157, filed May 6, 2015.
U.S. Response to Office Action filed Apr. 26, 2017 in U.S. Appl. No. 14/441,157, filed May 6, 2015.
U.S. Office Action dated Mar. 28, 2017 in U.S. Appl. No. 14/775,647, filed Sep. 11, 2015.
U.S. Response to Office Action filed Jun. 28, 2017 in U.S. Appl. No. 14/775,647, filed Sep. 11, 2015.
U.S. Notice of Allowance dated Feb. 8, 2017 in U.S. Appl. No. 13/883,535, filed May 3, 2013.
U.S. Rule 312 Amendment dated Apr. 3, 2017 in U.S. Appl. No. 13/883,535, filed May 3, 2013.
U.S. Preliminary Amendment dated Jul. 19, 2017 in U.S. Appl. No. 15/654,585, filed Jul. 19, 2017.
U.S. Response to Office Action filed Aug. 29, 2017 in U.S. Appl. No. 14/414,432, filed Jan. 12, 2015.
U.S. Office Action dated Nov. 17, 2017 in U.S. Appl. No. 14/414,432, filed Jan. 12, 2015.
U.S. Office Action dated Sep. 19, 2017 in U.S. Appl. No. 14/441,157, filed May 6, 2015.
U.S. Office Action dated Aug. 22, 2017 in U.S. Appl. No. 14/775,647, filed Sep. 11, 2015.

(56) References Cited

OTHER PUBLICATIONS

U.S. Response to Office Action filed Nov. 21, 2017 in U.S. Appl. No. 14/775,647, filed Sep. 11, 2015.
U.S. Divisional Application/Preliminary Amendment dated May 11, 2017 in U.S. Appl. No. 15/593,259, filed May 11, 2017.

* cited by examiner

SEQUENCE LISTING

<160> NUMBER OF SEQ ID NOS: 4

<210> SEQ ID NO 1
<211> LENGTH: 989
<212> TYPE: DNA
<213> ORGANISM: HOMO SAPIENS

<400> SEQUENCE: 1
gggcccaagc gtgttccccc tggcccccag cagcaagagc accagcggcg gcacagccgc      60
cctgggctgc ctggtgaagg actacttccc cgagcccgtg accgtgtcct ggaacagcgg     120
agccctgacc tccggcgtgc acaccttccc cgccgtgctg cagagcagcg gcctgtacag     180

-continued

```
cctgagcagc gtggtgaccg tgcccagcag cagcctgggc acccagacct acatctgtaa    240
cgtgaaccac aagcccagca acaccaaggt ggacaagaga gtggagccca agagctgtga    300
caagacccac acctgccccc cctgcccagc ccccgagctg ctgggcggac ccagcgtgtt    360
cctgttcccc cccaagccca aggacaccct gatgatcagc agaaccccg aggtgacctg     420 tgtggtggtg gacgtgtccc acgaggaccc agaggtgaag ttcaactggt acgtggacgg    480
cgtggaggtg cacaacgcca agaccaagcc cagagaggag cagtacagca gcacctacag    540
ggtggtgtcc gtgctgaccg tgctgcacca ggactggctg aacggcaagg agtacaagtg    600
taaggtgtcc aacaaggccc tgccagcccc aatcgaaaag accatcagca aggccaaggg    660
ccagccaaga gagcccagg tgtacaccct gccacccagc agggaggaga tgaccaagaa     720
ccaggtgtcc ctgacctgtc tggtgaaggg cttctaccca agcgacatcg ccgtggagtg    780
ggagagcaac ggccagcccg agaacaacta caagaccacc cccccagtgc tggacagcga    840
cggcagcttc ttcctgtaca gcaagctgac cgtggacaag agcagatggc agcagggcaa    900
cgtgttcagc tgctccgtga tgcacgaggc cctgcacaac cactacaccc agaagagcct    960
gagcctgtcc ccaggcaagt gatgaattc                                      989
```

<210> SEQ ID NO 2
<211> LENGTH: 326
<212> TYPE: PRT
<213> ORGANISM: HOMO SAPIENS

<400> SEQUENCE: 2

```
Gly Pro Ser Val Phe Pro Leu Ala Pro Ser Ser Lys Ser Thr Ser Gly
1               5                   10                  15

Gly Thr Ala Ala Leu Gly Cys Leu Val Lys Asp Tyr Phe Pro Glu Pro
            20                  25                  30

Val Thr Val Ser Trp Asn Ser Gly Ala Leu Thr Ser Gly Val His Thr
        35                  40                  45

Phe Pro Ala Val Leu Gln Ser Ser Gly Leu Tyr Ser Leu Ser Ser Val
    50                  55                  60

Val Thr Val Pro Ser Ser Ser Leu Gly Thr Gln Thr Tyr Ile Cys Asn
65                  70                  75                  80

Val Asn His Lys Pro Ser Asn Thr Lys Val Asp Lys Arg Val Glu Pro
                85                  90                  95

Lys Ser Cys Asp Lys Thr His Thr Cys Pro Pro Cys Pro Ala Pro Glu
            100                 105                 110

Leu Leu Gly Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Ser
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
        195                 200                 205

Ala Pro Ile Glu Lys Thr Ile Ser Lys Ala Lys Gly Gln Pro Arg Glu
    210                 215                 220
```

```
Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
            245                 250                 255

Ala Val Glu Trp Glu Ser Asn Gly Gln Pro Glu Asn Asn Tyr Lys Thr
        260                 265                 270

Thr Pro Pro Val Leu Asp Ser Asp Gly Ser Phe Phe Leu Tyr Ser Lys
    275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 3
<211> LENGTH: 989
<212> TYPE: DNA
<213> ORGANISM: HOMO SAPIENS

<400> SEQUENCE: 3
gggcccaagc gtgttccccc tggcccccag cagcaagagc accagcggcg gcacagccgc        60
cctgggctgc ctggtgaagg actacttccc cgagcccgtg accgtgtcct ggaacagcgg       120
agccctgacc tccggcgtgc acaccttccc cgccgtgctg cagagcagcg gcctgtacag       180
cctgagcagc gtggtgaccg tgcccagcag cagcctgggc acccagacct acatctgtaa       240
cgtgaaccac aagcccagca caccaaggt ggacaagaga gtggagccca gagctgtga        300 caagacccac acctgccccc ctgcccagc ccccgagctg ctgggcggac ccagcgtgtt       360
cctgttcccc ccaagcccca ggacaccct gatgatcagc agaaccccg aggtgacctg        420 tgtggtggtg gacgtgtccc acgaggaccc agaggtgaag ttcaactggt acgtggacgg       480
cgtggaggtg cacaacgcca agaccaagcc cagagaggag cagtaccaaa gcacctacag       540
ggtggtgtcc gtgctgaccg tgctgcacca ggactggctg aacggcaagg agtacaagtg       600
taaggtgtcc aacaaggccc tgccagcccc aatcgaaaag accatcagca aggccaaggg       660
ccagccaaga gagccccagg tgtacaccct gccacccagc agggaggaga tgaccaagaa       720
ccaggtgtcc ctgacctgtc tggtgaaggg cttctaccca gcgacatcg ccgtggagtg        780 ggagagcaac ggccagcccg agaacaacta caagaccacc cccccagtgc tggacagcga       840
cggcagcttc ttcctgtaca gcaagctgac cgtggacaag agcagatggc agcagggcaa       900
cgtgttcagc tgctccgtga tgcacgaggc cctgcacaac cactacaccc agaagagcct       960
gagcctgtcc ccaggcaagt gatgaattc                                        989

<210> SEQ ID NO 4
<211> LENGTH: 326
<212> TYPE: PRT
<213> ORGANISM: HOMO SAPIENS

<400> SEQUENCE: 4

Gly Pro Ser Val Phe Pro Leu Ala Pro Ser Ser Lys Thr Ser Gly
1               5                   10                  15

Gly Thr Ala Ala Leu Gly Cys Leu Val Lys Asp Tyr Phe Pro Glu Pro
            20                  25                  30

Val Thr Val Ser Trp Asn Ser Gly Ala Leu Thr Ser Gly Val His Thr
        35                  40                  45
```

-continued

```
Phe Pro Ala Val Leu Gln Ser Ser Gly Leu Tyr Ser Leu Ser Ser Val
    50                  55                  60
Val Thr Val Pro Ser Ser Ser Leu Gly Thr Gln Thr Tyr Ile Cys Asn
65                  70                  75                  80
Val Asn His Lys Pro Ser Asn Thr Lys Val Asp Lys Arg Val Glu Pro
                85                  90                  95
Lys Ser Cys Asp Lys Thr His Thr Cys Pro Pro Cys Pro Ala Pro Glu
            100                 105                 110
Leu Leu Gly Gly Pro Ser Val Phe Leu Phe Pro Pro Lys Pro Lys Asp
            115                 120                 125
Thr Leu Met Ile Ser Arg Thr Pro Glu Val Thr Cys Val Val Val Asp
    130                 135                 140
Val Ser His Glu Asp Pro Glu Val Lys Phe Asn Trp Tyr Val Asp Gly
145                 150                 155                 160
Val Glu Val His Asn Ala Lys Thr Lys Pro Arg Glu Glu Gln Tyr Gln
                165                 170                 175
Ser Thr Tyr Arg Val Val Ser Val Leu Thr Val Leu His Gln Asp Trp
            180                 185                 190
Leu Asn Gly Lys Glu Tyr Lys Cys Lys Val Ser Asn Lys Ala Leu Pro
            195                 200                 205
Ala Pro Ile Glu Lys Thr Ile Ser Lys Ala Lys Gly Gln Pro Arg Glu
    210                 215                 220
Pro Gln Val Tyr Thr Leu Pro Pro Ser Arg Glu Glu Met Thr Lys Asn
225                 230                 235                 240
Gln Val Ser Leu Thr Cys Leu Val Lys Gly Phe Tyr Pro Ser Asp Ile
                245                 250                 255
Ala Val Glu Trp Glu Ser Asn Gly Gln Pro Glu Asn Asn Tyr Lys Thr
            260                 265                 270
Thr Pro Pro Val Leu Asp Ser Asp Gly Ser Phe Phe Leu Tyr Ser Lys
            275                 280                 285
Leu Thr Val Asp Lys Ser Arg Trp Gln Gln Gly Asn Val Phe Ser Cys
    290                 295                 300
Ser Val Met His Glu Ala Leu His Asn His Tyr Thr Gln Lys Ser Leu
305                 310                 315                 320
Ser Leu Ser Pro Gly Lys
                325
```

ENZYMATIC CONJUGATION OF POLYPEPTIDES

CROSS-REFERENCE TO RELATED APPLICATIONS

This application is the U.S. National Phase of Application No. PCT/EP2014/063061 entitled "ENZYMATIC CONJUGATION OF POLYPEPTIDES" filed Jun. 20, 2014, which designated the United States and claims the benefit of U.S. Provisional Application No. 61/837,564, filed 20 Jun. 2013, which is incorporated herein by reference in its entirety, including any drawings.

REFERENCE TO SEQUENCE LISTING

The present application is being filed along with a Sequence Listing in electronic format. The Sequence Listing is provided as a file entitled "TGase9 PCT_ST25", created Jun. 20, 2014, which is 9 KB in size. The information in the electronic format of the Sequence Listing is incorporated herein by reference in its entirety.

FIELD OF THE INVENTION

The present application relates to the field of chemistry, biochemistry, and medicine. Disclosed herein are methods for the functionalization of immunoglobulins, in particular with drugs. Also disclosed herein are linking reagents, functionalized antibodies, pharmaceutical compositions, and method of treating disease and/or conditions.

BACKGROUND

Immunoglobulins conjugated to a drug of interest, generally known as antibody drug conjugates (ADCs), are a promising area of therapeutic research. Recent developments in ADC technology have focused on linker technology that provides for intracellular cleavage or more recently, non-cleavable linkers that provide greater in vivo stability and reduced toxicity. However, current linker technology does not provide stoichiometric coupling of drugs to antibodies. There is a need in the field for improved linker systems.

Transglutaminases (TGases) have been exploited for some time in the food industry for their ability to cross-link proteins. Such utilization has avoided the need to cross-link in quantitative or stoichiometric fashion. TGases have been shown to be capable of conjugating glutamine and lysine residues, including on antibodies (see, e.g., Josten et al. (2000) J. Immunol. Methods 240, 47-54; Mindt et al (2008) Bioconjug. Chem. 19, 271-278; Jeger et al (2010) Angew. Chem. Int. Ed. 49: 9995-9997); Kamiya et al (2003) Enzyme. Microb. Technol. 33, 492-496 and US patent publication no. 2011/0184147. While previous attempts to cross-link proteins have studied protein motifs that gave rise to conjugation and identified peptides that can be conjugated, the rules which govern selection by TGases of glutamine residues for modification are still largely unknown. Additionally, little is known about TGases' ability to take up different substrates, or their effect on the ability to TGases to conjugate in quantitative fashion.

SUMMARY OF THE INVENTION

Provided herein are methods using transglutaminase (TGase) to stoichiometrically functionalize acceptor glutamines on antibodies with large, charged and/or hydrophobic substrates. The disclosure arises from the finding that antibody substrates of TGase-mediated conjugation undergo deamidation of acceptor glutamines at reaction kinetics similar to conjugation of linkers such that significant deamidation occurs prior to conjugation of lysine-based linkers, particularly in cases where more difficult-to-conjugate linkers are used as TGase substrates (e.g. higher molecular weight, negatively charged and/or hydrophobic linkers). The deamidation correlates with a conjugation plateau in which small numbers of non-fully conjugated antibodies remain even if the amounts of TGase activity or linker substrate are increased (relative to antibody or acceptor glutamines). For example, for antibodies having one acceptor glutamine on each heavy or light chain, TGase-mediated conjugation has not been reported to provide a drug:antibody ratio (DAR) beyond the 1.6-1.8 range in a single step reaction. For antibodies having two acceptor glutamines on each heavy or light chain, TGase-mediated conjugation has not been reported to provide a drug:antibody ratio (DAR) beyond the 3.5 range.

It has been further discovered that modifying the coupling reaction process can resolve the problems of the coupling plateau. Surprisingly, by lowering rather than increasing TGase activity (the amount of activity determined by standard TGase activity assays), relative to the amount of antibody, high levels of conjugation can be achieved. A DAR of greater than 1.90 (e.g. 1.98) is achieved for antibodies having two acceptor glutamines per antibody, respectively. While increasing the concentration of linking reagent substrate can influence the conjugation reaction, large increases in linking reagent substrates in the absence of lowered TGase activity did not permit higher DARs to be obtained for coupling onto glutamines contained within heavy chain constant regions of antibodies, e.g. the naturally occurring acceptor glutamine at residue 295 (EU numbering). The environment of acceptor glutamines within the constant region of antibodies may thus hinder the ability of TGase to conjugate larger and/or hydrophobic linker substrates such that deamidation is favored at these residues.

The methods disclosed herein are particularly advantageous to achieve high levels of coupling of larger and/or hydrophobic molecules with cyclic groups onto constant regions of antibodies, e.g. onto naturally occurring acceptor glutamines or glutamines present on a TGase recognition tag introduced to an antibody by modifying one or more amino acids.

In one embodiment, the disclosure provides a method for producing an antibody conjugated to a moiety of interest, comprising the steps of:

a) providing a composition comprising a plurality of antibodies each comprising an acceptor glutamine residue; and b) reacting said antibody comprising an acceptor glutamine residue with a linking reagent comprising a primary amine and a moiety of interest in the presence of a TGase, wherein the ratio of TGase to antibodies that each comprise an acceptor glutamine residue is sufficient to obtain a composition comprising a plurality of antibodies comprising an acceptor glutamine residue linked to the linking reagent, wherein no more than 10%, optionally no more than 5%, optionally no more than 2%, or optionally no more than 1%, of the antibodies in the composition comprise a deamidated acceptor acceptor glutamine residue. In one embodiment, the TGase is present in an amount providing between about 0.001 and about 0.075 U/nmole of acceptor glutamine.

In one embodiment, the disclosure provides a method for producing an antibody conjugated to a moiety of interest, comprising the steps of:

a) providing a composition comprising a plurality of antibodies each comprising an acceptor glutamine residue; and b) reacting said antibody comprising an acceptor glutamine residue with a linking reagent comprising a primary amine and a moiety of interest, under suitable conditions, in the presence of an amount of TGase enzyme providing less than about 0.075 enzyme units (U), as determined by a hydroxamate activity assay, per nanomole (nmole) of acceptor glutamine, to obtain (e.g., in a single step) a composition comprising a plurality of antibodies comprising an acceptor glutamine residue linked (covalently) to the linking reagent, wherein no more than 10%, optionally no more than 5%, optionally no more than 2%, or optionally no more than 1%, of the antibodies in the composition comprise a deamidated acceptor acceptor glutamine residue.

In one embodiment, the disclosure provides a method for producing an antibody conjugated to a moiety of interest, comprising the steps of:

a) providing a composition comprising a plurality of antibodies each comprising an acceptor glutamine residue; and b) reacting said antibody comprising an acceptor glutamine residue with a linking reagent comprising a primary amine and a moiety of interest, under suitable conditions, in the presence of between about 0.001 and 0.075 enzyme units (U) of TGase, as determined by a hydroxamate activity assay, per nanomole (nmole) of acceptor glutamine, to obtain a composition comprising a plurality of antibodies comprising an acceptor glutamine residue linked to the linking reagent, wherein no more than 10%, optionally no more than 5%, optionally no more than 2%, or optionally no more than 1%, of the antibodies in the composition comprise a deamidated acceptor acceptor glutamine residue.

In one embodiment, the disclosure provides a method for producing an antibody conjugated to a moiety of interest, comprising the steps of:

a) providing a composition comprising a plurality of antibodies each comprising an acceptor glutamine residue; and b) reacting said antibody comprising an acceptor glutamine residue with a linking reagent comprising a primary amine and a moiety of interest, under suitable conditions, in the presence of between about 0.004 and 0.3 enzyme units (U) of TGase, as determined by a hydroxamate activity assay, per nanomole (nmole) of antibody, to obtain a composition comprising a plurality of antibodies comprising an acceptor glutamine residue linked to the linking reagent, wherein no more than 10%, optionally no more than 5%, optionally no more than 2%, or optionally no more than 1%, of the antibodies in the composition comprise a deamidated acceptor acceptor glutamine residue.

In one embodiment of any of the methods herein, the method further comprises a step of removing any excess (unreacted) linking reagent. In one embodiment, the method further comprises a step of removing any TGase enzyme. In one embodiment, any of said removing steps comprise a step of contacting the antibody composition with an affinity medium, optionally a washing step to remove unreacted linking reagent and/or TGase, and optionally a step of eluting said antibodies.

In one embodiment of any of the methods herein, the moiety of interest is an organic compound that is electrically negatively charged, hydrophobic and/or that has a molecular weight of at least 400 g/mol, 500 g/mol, 600 g/mol, 700 g/mol, 800 g/mol, 900 g/mol, 1000 g/mol or 2000 g/mol; optionally the moiety of interest (Z) is an anticancer agent selected from the group consisting of taxanes, anthracyclines, camptothecins, epothilones, mytomycins, combretastatins, vinca alkaloids, nitrogen mustards, maytansinoids, calicheamycins, duocarmycins, tubulysins, dolastatins and auristatins, enediynes, amatoxins, pyrrolobenzodiazepines, ethylenimines, radioisotopes, therapeutic proteins and peptides, and toxins or fragments thereof.

In one embodiment, TGase is present in an amount providing less than 0.2, optionally less than about 0.15 U/nmole of antibody, wherein the antibody has two acceptor glutamines (e.g., one acceptor glutamine on each heavy chain). In one embodiment, the TGase is present in an amount providing less than about 0.07, optionally less than about 0.06, optionally less than about 0.05, optionally less than about 0.04, or optionally about about 0.0375 or less than about 0.0375 U/nmole of acceptor glutamine. In one embodiment, TGase is present in an amount providing about 0.075 or less than about 0.075 U/nmole antibody, wherein the antibody has two acceptor glutamines. In one embodiment, TGase is present in an amount providing about 0.015 or less than about 0.15 U/nmole of antibody, wherein the antibody has four acceptor glutamines (e.g., two acceptor glutamines on each heavy chain).

In one embodiment, TGase is present in an amount providing less than about 0.03, 0.02, or 0.01, optionally less than about 0.0075 U/nmole of acceptor glutamine. In one embodiment, TGase is present in an amount providing less than about 0.06, 0.04, or 0.02, optionally less than about 0.015 U/nmole per nanomole of antibody, wherein the antibody has two acceptor glutamines. In one embodiment, TGase is present in an amount providing less than about 0.075 U/nmole of antibody, wherein the antibody has four acceptor glutamines. In one embodiment, TGase is present in an amount providing less than about 0.12, 0.08, 0.04, or 0.03 U/nmole of antibody, optionally less than about 0.015 U/nmole of antibody, wherein the antibody has four acceptor glutamines.

Optionally, in any embodiment herein, TGase is present in an amount providing at least about 0.0002 U/nmole of acceptor glutamine, at least about 0.0004 U/nmole of acceptor glutamine, at least about 0.001 U/nmole of acceptor glutamine, at least about 0.002 U/nmole of acceptor glutamine, at least about 0.005 U/nmole of acceptor glutamine, at least about 0.01 U/nmole of acceptor glutamine, or at least 0.015 U/nmole of acceptor glutamine. Optionally, in any embodiment herein, TGase is present in an amount providing at least 0.0004 U/nmole of antibody, at least about 0.0008 U/nmole of antibody, at least about 0.0016 U/nmole of antibody, at least about 0.004 U/nmole of antibody, or at least about 0.01 U/nmole of antibody.

In one embodiment, said moiety of interest of step (b) is a reactive group (R), optionally a protected reactive group and the method further comprises a step (c): reacting the composition comprising a plurality of antibodies obtained in step (b), optionally immobilized on a solid support, with a compound comprising (i) a moiety (Z) that improves pharmacokinetic properties, a therapeutic moiety or a diagnostic moiety, and (ii) a reactive group (R') capable of reacting with reactive group R, under conditions sufficient to obtain a composition comprising antibodies comprising an acceptor glutamine linked to a moiety (Z) via said linking reagent, optionally wherein no more than 10%, optionally no more than 5%, optionally no more than 2%, optionally no more than 1%, of the antibodies in the composition comprise a deamidated acceptor acceptor glutamine residue.

In one aspect of any embodiment herein, at least 90%, 95%, 98% or 99% of the antibodies in said composition obtained have (m) functionalized acceptor glutamine residues (Q) per antibody, wherein m is an integer selected from 1, 2 or 4.

In one aspect of any embodiment herein, the antibody comprises one acceptor glutamine on each heavy chain. In one aspect of any embodiment herein, at least 90%, 95%, 98% or 99% of the antibodies in said composition obtained comprise on each heavy or light chain one functionalized acceptor glutamine residue (Q) having the structure of Formula IVa. In one embodiment, the moiety of interest (Z or R): antibody ratio (DAR) is at least 1.9, optionally at least 1.95, optionally at least 1.98.

In one aspect of any embodiment herein, the antibody comprises two acceptor glutamines on each heavy chain. In one aspect of any embodiment herein, at least 90%, 95%, 98% or 99% of the antibodies in said composition obtained comprise on each heavy chain two functionalized acceptor glutamine residues (Q) having the structure of Formula IVa. In one embodiment, the moiety of interest (Z or R): antibody ratio (DAR) is at least 3.8, optionally at least 3.9, optionally 3.95.

In one embodiment, the disclosure provides a vessel (e.g. container, reaction vessel) comprising:

(a) a plurality of antibodies each comprising an acceptor glutamine residue, wherein no more than 10%, optionally no more than 5%, optionally no more than 2%, or optionally no more than 1%, of the antibodies comprise a deamidated acceptor acceptor glutamine residue;

(b) optionally, a linking reagent comprising a primary amine and a moiety of interest; and (c) a transglutaminase (TGase) enzyme capable of causing the formation of a covalent bond between the acceptor glutamine residue and the linking reagent (at the primary amine of the linking reagent).

In one embodiment, the moiety of interest is an organic compound that is electrically negatively charged, hydrophobic and/or that has a molecular weight of at least 400 g/mol, 500 g/mol, 600 g/mol, 700 g/mol, 800 g/mol, 900 g/mol, 1000 g/mol or 2000 g/mol; optionally the moiety of interest (Z) is an anticancer agent selected from the group consisting of taxanes, anthracyclines, camptothecins, epothilones, mytomycins, combretastatins, vinca alkaloids, nitrogen mustards, maytansinoids, calicheamycins, duocarmycins, tubulysins, dolastatins and auristatins, enediynes, amatoxins, pyrrolobenzodiazepines, ethylenimines, radioisotopes, therapeutic proteins and peptides, and toxins or fragments thereof.

In one embodiment, the amount of TGase provides less than 0.075 enzyme units (U), as determined by a hydroxamate activity assay, per nanomole (nmole) of acceptor glutamine. In one embodiment, TGase is present in an amount providing less than about 0.15 U/nmole of antibody, wherein the antibody has two acceptor glutamines (e.g., one acceptor glutamine on each heavy chain). In one embodiment, TGase is present in an amount providing less than about 0.07, optionally less than about 0.06, optionally less than about 0.05, optionally less than about 0.04, or optionally about about 0.0375 or less than about 0.0375 U/nmole of acceptor glutamine. In one embodiment, TGase is present in an amount providing less than about 0.08, optionally less than about 0.075 U/nmole antibody, wherein the antibody has two acceptor glutamines. In one embodiment, TGase is present in an amount providing less than about 0.2, optionally less than about 0.15 U/nmole of antibody, wherein the antibody has four acceptor glutamines (e.g., two acceptor glutamines on each heavy chain).

In one embodiment, TGase is present in an amount providing less than about 0.03, 0.02, or 0.01, optionally less than about 0.0075 U/nmole of acceptor glutamine. In one embodiment, TGase is present in an amount providing less than about 0.06, 0.04, or 0.02, optionally less than about 0.015 U/nmole per nanomole of antibody, wherein the antibody has two acceptor glutamines. In one embodiment, TGase is present in an amount providing less than about 0.075 U/nmole of antibody, wherein the antibody has four acceptor glutamines. In one embodiment, TGase is present in an amount providing less than about 0.06, 0.04, or 0.02, optionally less than about 0.015 U/nmole of antibody, wherein the antibody has four acceptor glutamines.

Optionally, in any embodiment herein, TGase is present in an amount providing at least about 0.0002 U/nmole of acceptor glutamine, at least about 0.0004 U/nmole of acceptor glutamine, at least about 0.001 U/nmole of acceptor glutamine, at least about 0.002 U/nmole of acceptor glutamine, at least about 0.005 U/nmole of acceptor glutamine or at least about 0.01 U/nmole of acceptor glutamine. Optionally, in any embodiment herein, TGase is present in an amount providing at least about 0.0004 U/nmole of antibody, at least about 0.0008 U/nmole of antibody, at least about 0.0016 U/nmole of antibody, at least about 0.004 U/nmole of antibody, or at least about 0.01 U/nmole of antibody.

The elements comprised in the vessel may be fully reacted, unreacted or partially reacted. In one embodiment, the elements comprised in the vessel represent a reaction intermediate. In one embodiment, less than 90%, 80%, 60% or 50% of the antibodies in said vessel have (m) functionalized acceptor glutamine residues (Q) per antibody, wherein m is an integer selected from 1, 2 or 4. In one embodiment, the elements comprised in the vessel represent the product of a completed coupling reaction. In one embodiment, at least 90%, 95%, 98% or 99% of the antibodies in said vessel have (m) functionalized acceptor glutamine residues (Q) per antibody, wherein m is an integer selected from 1, 2 or 4.

In one embodiment, the antibody comprises one acceptor glutamine on each heavy chain. In one aspect of any embodiment herein, at least 90%, 95%, 98% or 99% of the antibodies in said vessel comprise on each heavy or light chain one functionalized acceptor glutamine residue (Q) having the structure of Formula IVa. In one embodiment, the moiety of interest (Z or R): antibody ratio (DAR) is at least 1.9, optionally at least 1.95, optionally at least 1.98.

In one embodiment, the antibody comprises two acceptor glutamines on each heavy chain. In one aspect of any embodiment herein, at least 90%, 95%, 98% or 99% of the antibodies in said vessel comprise on each heavy chain two functionalized acceptor glutamine residues (Q) having the structure of Formula IVa. In one embodiment, the moiety of interest (Z or R): antibody ratio (DAR) is at least 3.8, optionally at least 3.9, optionally 3.95.

In one aspect the disclosure provides a composition comprising a plurality of antibodies comprising a functionalized glutamine residue linked (covalently) to a linking reagent comprising a moiety of interest, wherein no more than 10%, optionally no more than 5%, optionally no more than 2%, optionally no more than 1%, of the antibodies comprise a deamidated acceptor acceptor glutamine residue. In one embodiment, the moiety of interest (or moiety Z) is an organic compound that is electrically negatively charged, hydrophobic and/or that has a molecular weight of at least 400 g/mol. In one embodiment, at least 90%, 95%, 98% or 99% of the antibodies in said composition obtained have (m) functionalized acceptor glutamine residues (Q) per antibody, wherein m is an integer selected from 1, 2 or 4. In one embodiment, the moiety of interest is an organic compound that is electrically negatively charged, hydrophobic and/or that has a molecular weight of at least 500 g/mol, 600 g/mol, 700 g/mol, 800 g/mol, 900 g/mol, 1000 g/mol or 2000 g/mol; optionally the moiety of interest (Z) is an anticancer agent selected from the group consisting of taxanes, anthracyclines, camptothecins, epothilones, mytomycins, combretastatins, vinca alkaloids, nitrogen mustards, maytansinoids, calicheamycins, duocarmycins, tubulysins, dolastatins and auristatins, enediynes, amatoxins, pyrrolobenzodiazepines, ethylenimines, radioisotopes, therapeutic proteins and peptides, and toxins or fragments thereof.

In one embodiment, at least 90%, 95%, 98% or 99% of the antibodies in said composition comprise two functionalized acceptor glutamine residue (Q) having the structure of Formula IVa,

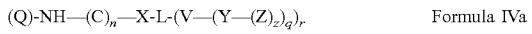
(Q)-NH—(C)$_n$—X-L-(V—(Y—(Z)$_z$)$_q$)$_r$     Formula IVa or a pharmaceutically acceptable salt or solvate thereof, wherein:

Q is a glutamine residue present in an antibody or antibody fragment;

(C)$_n$ is a substituted or unsubstituted alkyl or heteroalkyl chain, optionally wherein any carbon of the chain is substituted with an alkoxy, hydroxyl, alkylcarbonyloxy, alkyl-S—, thiol, alkyl-C(O)S—, amine, alkylamine, amide, or alkylamide;

n is an integer selected from among the range of 2 to 20;

X is NH, O, S, absent, or a bond;

L is independently absent, a bond or a continuation of a bond, or a carbon comprising framework of 5 to 200 atoms substituted at one or more atoms;

r is an integer selected from among 1, 2, 3 or 4;

q is an integer selected from among 1, 2, 3 or 4;

z is an integer selected from among 1, 2, 3 or 4; and

V is independently absent, a bond or a continuation of a bond, a non-cleavable moiety or a conditionally-cleavable moiety;

Y is independently absent, a bond or a continuation of a bond, or a spacer system which is comprised of 1 or more spacers; and Z is a moiety that improves pharmacokinetic properties, a therapeutic moiety or a diagnostic moiety.

In one embodiment, at least 90%, 95%, 98% or 99% of the antibodies in said composition comprise four functionalized acceptor glutamine residues (Q) having the structure of Formula IVa,

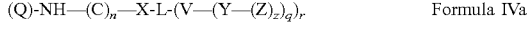
(Q)-NH—(C)$_n$—X-L-(V—(Y—(Z)$_z$)$_q$)$_r$     Formula IVa or a pharmaceutically acceptable salt or solvate thereof, wherein:

Q is a glutamine residue present in an antibody or antibody fragment;

(C)$_n$ is a substituted or unsubstituted alkyl or heteroalkyl chain, optionally wherein any carbon of the chain is substituted with an alkoxy, hydroxyl, alkylcarbonyloxy, alkyl-S—, thiol, alkyl-C(O)S—, amine, alkylamine, amide, or alkylamide;

n is an integer selected from among the range of 2 to 20;

X is NH, O, S, absent, or a bond;

L is independently absent, a bond or a continuation of a bond, or a carbon comprising framework of 5 to 200 atoms substituted at one or more atoms;

r is an integer selected from among 1, 2, 3 or 4;

q is an integer selected from among 1, 2, 3 or 4;

z is an integer selected from among 1, 2, 3 or 4; and

V is independently absent, a bond or a continuation of a bond, a non-cleavable moiety or a conditionally-cleavable moiety;

Y is independently absent, a bond or a continuation of a bond, or a spacer system which is comprised of 1 or more spacers; and Z is a moiety that improves pharmacokinetic properties, a therapeutic moiety or a diagnostic moiety.

In one embodiment, at least 90%, 95%, 98% or 99% of the antibodies in said composition obtained comprise one, two or four functionalized acceptor glutamine residues (Q) having the structure of Formula II:

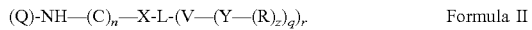
(Q)-NH—(C)$_n$—X-L-(V—(Y—(R)$_z$)$_q$)$_r$     Formula II or a pharmaceutically acceptable salt or solvate thereof, wherein:

Q is a glutamine residue present in an antibody or antibody fragment;

(C)$_n$ is a substituted or unsubstituted alkyl or heteroalkyl chain, optionally wherein any carbon of the chain is optionally substituted with alkoxy, hydroxyl, alkylcarbonyloxy, alkyl-S—, thiol, alkyl-C(O)S—, amine, alkylamine, amide, or alkylamide;

n is an integer from among the range of 2 to 20;

X is NH, O, S, absent or a bond;

L is independently absent, a bond or a continuation of a bond, or a carbon comprising framework of 1 to 200 atoms substituted at one or more atoms, optionally wherein the carbon comprising framework comprises a linear framework of 3 to 30 carbon atoms optionally substituted at one or more atoms, optionally wherein the carbon comprising framework is a linear hydrocarbon, a symmetrically or asymmetrically branched hydrocarbon, monosaccharide, disaccharide, linear or branched oligosaccharide (asymmetrically branched or symmetrically branched), other natural linear or branched oligomers (asymmetrically branched or symmetrically branched), or a dimer, trimer, or higher oligomer (linear, asymmetrically branched or symmetrically branched) resulting from any chain-growth or step-growth polymerization process;

r is an integer selected from among 1, 2, 3 or 4;

q is an integer selected from among 1, 2, 3 or 4;

z is an integer selected from among 1, 2, 3 or 4; and

V is independently absent, a bond or a continuation of a bond, a non-cleavable moiety or a conditionally-cleavable moiety;

Y is independently absent, a bond or a continuation of a bond, or a spacer system which is comprised of 1 or more spacers; and R is a reactive moiety.

In one embodiment, at least 90%, 95%, 98% or 99% of the antibodies in said composition obtained comprise one, two or four functionalized acceptor glutamine residues (Q) having the structure of Formula IVb,

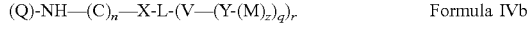
(Q)-NH—(C)$_n$—X-L-(V—(Y-(M)$_z$)$_q$)$_r$     Formula IVb or a pharmaceutically acceptable salt or solvate thereof, wherein:

Q is a glutamine residue present in an antibody or antibody fragment;

(C)$_n$ is a substituted or unsubstituted alkyl or heteroalkyl chain, optionally wherein any carbon of the chain is substituted with a alkoxy, hydroxyl, alkylcarbonyloxy, alkyl-S—, thiol, alkyl-C(O)S—, amine, alkylamine, amide, or alkylamide;

n is an integer selected from among the range of 2 to 20;

X is NH, O, S, absent, or a bond;

L is independently absent, a bond or a continuation of a bond, or a carbon comprising framework of 1 to 200 atoms substituted at one or more atoms, optionally, wherein the carbon comprising framework comprises a linear framework of 3 to 30 carbon atoms optionally substituted at one or more atoms, optionally wherein the carbon comprising framework is a linear hydrocarbon, a symmetrically or asymmetrically branched hydrocarbon, monosaccharide, disaccharide, linear or branched oligosaccharide (asymmetrically branched or symmetrically branched), other natural linear or branched oligomers (asymmetrically branched or symmetrically branched), or a dimer, trimer, or higher oligomer (linear, asymmetrically branched or symmetrically branched) resulting from any chain-growth or step-growth polymerization process;

r is an integer selected from among 1, 2, 3 or 4;

q is an integer selected from among 1, 2, 3 or 4;

z is an integer selected from among 1, 2, 3 or 4;

V is independently absent, a bond or a continuation of a bond, a non-cleavable moiety or a conditionally-cleavable moiety;

Y is independently absent, a bond or a continuation of a bond, or a spacer system which is comprised of 1 or more spacers;

M is independently: R or (RR')-L'-(V'—(Y'—(Z)$_z$)$_{q'}$)$_{r'}$, wherein

R is a reactive moiety;

(RR') is an addition product between R and a complementary reactive moiety R';

L' is independently absent, a bond or a continuation of a bond, or a carbon comprising framework of 1 to 200 atoms substituted at one or more atoms, optionally, wherein the carbon comprising framework comprises a linear framework of 3 to 30 carbon atoms optionally substituted at one or more atoms, optionally wherein the carbon comprising framework is a linear hydrocarbon, a symmetrically or asymmetrically branched hydrocarbon, monosaccharide, disaccharide, linear or branched oligosaccharide (asymmetrically branched or symmetrically branched), other natural linear or branched oligomers (asymmetrically branched or symmetrically branched), or a dimer, trimer, or higher oligomer (linear, asymmetrically branched or symmetrically branched) resulting from any chain-growth or step-growth polymerization process;

V' is independently absent, a bond or a continuation of a bond, a non-cleavable moiety or a conditionally-cleavable moiety;

Y' is independently absent, a bond or a continuation of a bond, or a spacer system which is comprised of 1 or more spacers;

Z is independently a reactive group, a moiety that improves the pharmacokinetic properties, a therapeutic or diagnostic moiety, and each Z is directly coupled to either Y or V when Y is absent, or L when both Y and V are absent; and z', q' and r' are each independently an integer selected from among 1, 2, 3 or 4.

In one embodiment, substantially no free linking reagent is present in the composition. In another embodiment, free linking reagent is present in an amount which is equal to or less than 20, 10, 6, 5, 4, 2 or 1.5 molar equivalents per acceptor glutamine present on the antibody. In one embodiment, substantially no TGase is present in the composition. In another embodiment, the composition further comprises an amount of TGase providing between 0.001 and 0.075 enzyme units (U), as determined by a hydroxamate activity assay, per nanomole (nmole) of acceptor glutamine.

In one embodiment, the disclosure provides a composition comprising a plurality of antibodies comprising a functionalized acceptor glutamine residue linked (covalently) to a linking reagent, wherein at least 90%, 95%, 98% or 99% of the antibodies in said composition obtained comprise two or four functionalized acceptor glutamine residue (Q) having the structure of Formula IVa,

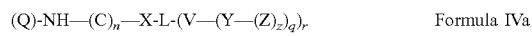

(Q)-NH—(C)$_n$—X-L-(V—(Y—(Z)$_z$)$_q$)$_r$    Formula IVa or a pharmaceutically acceptable salt or solvate thereof, wherein:

Q is a glutamine residue present in an antibody or antibody fragment;

(C)$_n$ is a substituted or unsubstituted alkyl or heteroalkyl chain, optionally wherein any carbon of the chain is substituted with an alkoxy, hydroxyl, alkylcarbonyloxy, alkyl-S—, thiol, alkyl-C(O)S—, amine, alkylamine, amide, or alkylamide;

n is an integer selected from among the range of 2 to 20;

X is NH, O, S, absent, or a bond;

L is independently absent, a bond or a continuation of a bond, or a carbon comprising framework of 5 to 200 atoms substituted at one or more atoms;

r is an integer selected from among 1, 2, 3 or 4;

q is an integer selected from among 1, 2, 3 or 4;

z is an integer selected from among 1, 2, 3 or 4; and

V is independently absent, a bond or a continuation of a bond, a non-cleavable moiety or a conditionally-cleavable moiety;

Y is independently absent, a bond or a continuation of a bond, or a spacer system which is comprised of 1 or more spacers; and Z is a moiety that improves pharmacokinetic properties, a therapeutic moiety or a diagnostic moiety, wherein Z is an organic compound that is electrically negatively charged, hydrophobic and/or that has a molecular weight of at least 400 g/mol, 500 g/mol, 600 g/mol, 700 g/mol, 800 g/mol, 900 g/mol, 1000 g/mol or 2000 g/mol.

In one aspect of any of the antibody compositions herein, the moiety of interest (Z or R): antibody ratio (DAR) is at least 1.9, optionally at least 1.95, optionally at least 1.98 (e.g. for antibodies having two acceptor glutamine per antibody). In one aspect of any of the antibody compositions herein, the moiety of interest (Z or R): antibody ratio (DAR) is at least 3.8, optionally at least 3.9, optionally 3.95 (e.g. for antibodies having four acceptor glutamine per antibody).

In one aspect of any of the embodiments herein, the linking reagent comprising a moiety of interest (e.g., a reactive group (R) or a moiety (Z) that improves pharmacokinetic properties, a therapeutic moiety or a diagnostic moiety) is provided in an amount which is equal or less than about 20, 10, 6, 5, 4, 2 or 1.5 molar equivalents per acceptor glutamine present on the antibody.

In one aspect of any of the embodiments herein, the linking reagent is provided in an amount which is between about 2 and about 15, optionally between about 8 and about 12, or optionally about 10 or at least 10 molar equivalents per acceptor glutamine present on the antibody.

In one aspect of any of the embodiments herein, the linking reagent is provided in an amount which is at least about 15, optionally between about 15 and about 25, optionally between about 18 and about 22, or optionally about about 20 or at least about 20 molar equivalents per acceptor glutamine present on the antibody.

In one aspect of any of the embodiments herein, the antibody comprises an acceptor glutamine residue is provided at a concentration of between about 0.01 mg/mL and about 10 mg/m L.

In one aspect of any of the embodiments herein, the transglutaminase enzyme is provided at a concentration of between about 0.1 U mg/mL and about 5 U mg/mL.

In one aspect of any of the embodiments herein, the antibody is a tetrameric antibody comprising two Ig heavy chains having Fc regions and two Ig light chains.

In one aspect of any embodiment herein, the antibody is an antibody fragment.

In one aspect of any embodiment herein, the antibody comprises an acceptor amino acid residue within a constant region. Optionally, the acceptor amino acid residue is an acceptor glutamine naturally present in an Fc region, optionally in a CH2 or CH3 domain, optionally at residue 295 (Kabat EU numbering).

In one aspect of any embodiment herein, said plurality of antibodies in the composition share the same heavy and/or light chain amino acid sequences.

In one aspect of any embodiment herein, said linking reagent comprises a NH—(C)$_n$ group, wherein (C)$_n$ is a substituted or unsubstituted alkyl or heteroalkyl chain, wherein any carbon of the chain is optionally substituted with an alkoxy, hydroxyl, alkylcarbonyloxy, alkyl-S—, thiol, alkyl-C(O)S—, amine, alkylamine, amide, or alkylamide; and n is an integer selected from among the range of 2 to 20.

In one aspect of any embodiment herein, said acceptor glutamine residue is flanked at position +2 by a non-aspartic acid residue. In one aspect of any embodiment herein, said antibody comprises a N297X or a Q295X substitution, wherein X is any amino acid other than aspartic acid. In one aspect of any embodiment herein, said antibody comprises a N297X or a Q295X substitution, wherein X is any amino acid other than aspartic acid or glutamine.

In one aspect the disclosure provides a composition obtained according to any of the methods of disclosed herein.

In one aspect the disclosure provides a pharmaceutical composition comprising an antibody composition disclosed herein and a pharmaceutically acceptable excipient. In one aspect, the composition is substantially free of TGase enzyme and/or of free (not conjugated to a acceptor glutamine) linking reagent.

In one aspect the disclosure provides a method for treating a subject having a disease comprising administering to the subject a composition according to any aspect disclosed herein and a pharmaceutically acceptable excipient.

Reference to "Formulas I", "Formula II", "Formula III" or "Formula IV", unless the context clearly indicates otherwise, designates all compounds derived from such Formulas I to IV, including e.g., Formula I includes reference to Ia and/or Ib, Formula IV includes IVa and IVb.

Any of the methods of the disclosure can further be characterized as comprising any step described in the application, including notably in the "Detailed Description of the Invention"). Further provided is an antibody obtainable by any of present methods. Further provided are pharmaceutical or diagnostic formulations of the antibodies disclosed herein. The disclosure further provides methods of using an antibody composition in a method of treatment or diagnosis.

The disclosure of U.S. application Ser. No. 13/725,382 filed on Dec. 21, 2012, and entitled "Enzymatic Conjugation of Polypeptides" is hereby incorporated by reference in its entirety.

These and additional advantageous aspects and features may be further described elsewhere herein.

BRIEF DESCRIPTION OF THE DRAWINGS

FIG. 2A shows results for an antibody having a N297S mutation (1 acceptor glutamine on each heavy chain) and FIG. 2B shows results for an antibody having a N297Q mutation (2 acceptor glutamines on each heavy chain).

DETAILED DESCRIPTION OF THE INVENTION

Introduction

Figure 1:
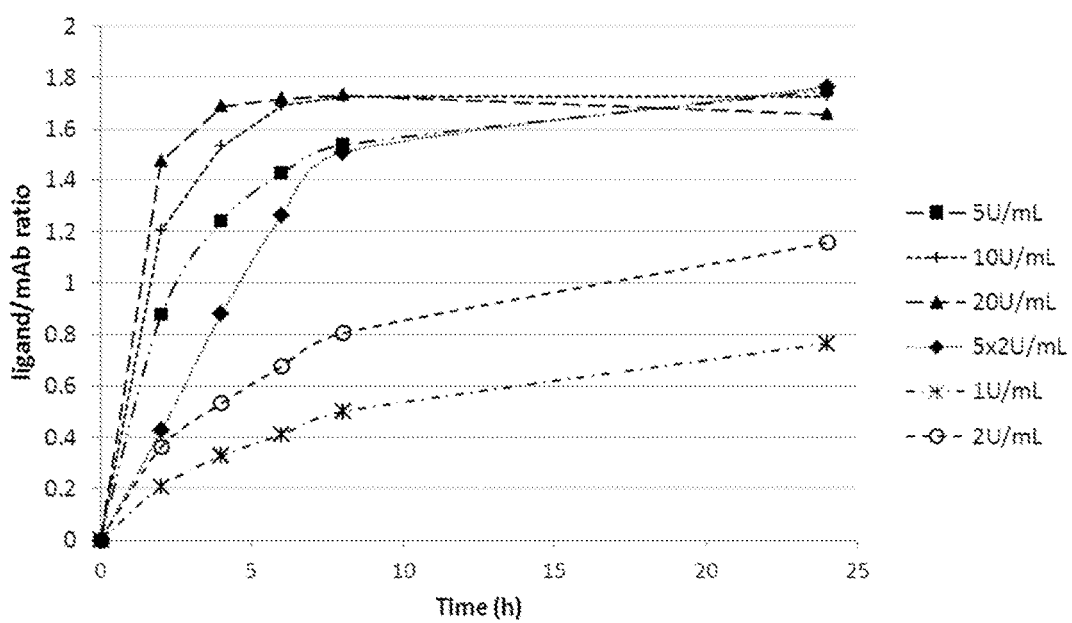
FIG. 1 shows BTG concentrations conditions for BTG coupling of small non-hydrophobic linkers onto PNGaseF-deglycosylated antibodies; increasing concentrations of BTG improves coupling of small non-hydrophobic linkers.

According to the embodiments provided herein, the functionalization of antibodies is site-specific and occurs via, respectively between a primary amine (e.g. of a lysine or lysine-like moiety) and an acceptor glutamine residue of an antibody by transglutaminase.

The inventors now present a convenient method for the site-specific functionalization by large chemical molecules (e.g., cytotoxic drugs such as duocarmycins, auristatins, etc.) of immunoglobulins under near physiological conditions. The enzymatic activity of the transglutaminase family catalyzes an acyl transfer reaction between the γ-carboxamide groups of peptide-bound glutamine residues and various primary amines or ε-amino groups of lysine residues, thus forming isopeptidic bonds which are stable and resistant to chemical, enzymatic, and physical degradation. The function of TGases can be described as incorporation of alkylamine derivatives into specific glutamine residues or vice versa. This specificity has been recognized before and has already been applied successfully for different purposes.

Definitions

As used in the specification, "a" or "an" may mean one or more. As used in the claim(s), when used in conjunction with the word "comprising", the words "a" or "an" may mean one or more than one. As used herein "another" may mean at least a second or more.

Where "comprising" is used, this can be replaced by "consisting essentially of", or by "consisting of".

As used herein, the term 'about' means plus or minus 10-20 percent of the amount to which the term 'about' refers.

The term "transglutaminase", used interchangeably with "TGase" or "TG", refers to an enzyme capable of cross-linking proteins through an acyl-transfer reaction between the γ-carboxamide group of peptide-bound glutamine and the ε-amino group of a lysine or a structurally related primary amine such as amino pentyl group, e.g. a peptide-bound lysine, resulting in a ε-(γ-glutamyl)lysine isopeptide bond. TGases include, inter alia, bacterial transglutaminase (BTG) such as the enzyme having EC reference EC 2.3.2.13 (protein-glutamine-γ-glutamyltransferase).

The term "acceptor glutamine residue", when referring to a glutamine residue of an antibody, means a glutamine residue that is recognized by a TGase and can be cross-linked by a TGase through a reaction between the glutamine and a lysine or a structurally related primary amine such as amino pentyl group. Preferably the acceptor glutamine residue is a surface-exposed glutamine residue.

The term "TGase recognition tag", which refers to a sequence of amino acids that when incorporated into (e.g. appended to) a polypeptide sequence, under suitable conditions, is recognized by a TGase and leads to cross-linking by the TGase through a reaction between an amino acid side chain within the sequence of amino acids and a reaction partner.

The term "antibody" herein is used in the broadest sense and specifically includes full-length monoclonal antibodies, polyclonal antibodies, multispecific antibodies (e.g., bispecific antibodies), and antibody fragments, so long as they exhibit the desired biological activity. Various techniques relevant to the production of antibodies are provided in, e.g., Harlow, et al., ANTIBODIES: A LABORATORY MANUAL, Cold Spring Harbor Laboratory Press, Cold Spring Harbor, N.Y., (1988).

An "antibody fragment" comprises a portion of a full-length antibody, preferably antigen-binding or variable regions thereof. Examples of antibody fragments include Fab, Fab', F(ab)$_2$, F(ab)$_2$, F(ab)$_3$, Fv (typically the VL and VH domains of a single arm of an antibody), single-chain Fv (scFv), dsFv, Fd fragments (typically the VH and CH1 domain), and dAb (typically a VH domain) fragments; VH, VL, VhH, and V-NAR domains; minibodies, diabodies, triabodies, tetrabodies, and kappa bodies (see, e.g., Ill et al., Protein Eng 1997; 10: 949-57); camel IgG; IgNAR; and multispecific antibody fragments formed from antibody fragments, and one or more isolated CDRs or a functional paratope, where isolated CDRs or antigen-binding residues or polypeptides can be associated or linked together so as to form a functional antibody fragment. Various types of antibody fragments have been described or reviewed in, e.g., Holliger and Hudson, Nat Biotechnol 2005; 23, 1126-1136; WO2005040219, and published U.S. Patent Applications 20050238646 and 20020161201.

By "variable region" as used herein is meant the region of an antibody that comprises one or more Ig domains substantially encoded by any of the VL (including Vkappa and Vlambda) and/or VH genes that make up the light chain (including kappa and lambda) and heavy chain immunoglobulin genetic loci respectively. A light or heavy chain variable region (VL and VH) consists of a "framework" or "FR" region interrupted by three hypervariable regions referred to as "complementarity determining regions" or "CDRs". The extent of the framework region and CDRs have been precisely defined, for example as in Kabat (see "Sequences of Proteins of Immunological Interest," E. Kabat et al., U.S. Department of Health and Human Services, (1983)), and as in Chothia. The framework regions of an antibody, that is the combined framework regions of the constituent light and heavy chains, serves to position and align the CDRs, which are primarily responsible for binding to an antigen.

By "constant region" of an antibody as defined herein is meant the region of the antibody that is encoded by one of the light or heavy chain immunoglobulin constant region genes. By "constant light chain" or "light chain constant region" as used herein is meant the region of an antibody encoded by the kappa (Ckappa) or lambda (Clambda) light chains. The constant light chain typically comprises a single domain, and as defined herein refers to positions 108-214 of Ckappa, or Clambda, wherein numbering is according to the EU index of Kabat (Kabat et al., 1991, Sequences of Proteins of Immunological Interest, 5th Ed., United States Public Health Service, National Institutes of Health, Bethesda) and/or Edelman, G. M. et al., Proc. Natl. Acad. USA, 63, 78-85 (1969). By "constant heavy chain" or "heavy chain constant region" as used herein is meant the region of an antibody encoded by the mu, delta, gamma, alpha, or epsilon genes to define the antibody's isotype as IgM, IgD, IgG, IgA, or IgE, respectively. For full length IgG antibodies, the constant heavy chain, as defined herein, refers to the N-terminus of the CH1 domain to the C-terminus of the CH3 domain, thus comprising positions 118-447. Unless indicated otherwise, numbering within the constant region is according to the EU index of Kabat (1991) and/or Edelman, G. M. et al., Proc. Natl. Acad. USA, 63, 78-85 (1969).

By "Fab" or "Fab region" as used herein is meant the polypeptide that comprises the VH, CH1, VL, and CL immunoglobulin domains. Fab may refer to this region in isolation, or this region in the context of a full length antibody, antibody fragment or Fab fusion protein, or any other antibody embodiments as outlined herein.

By "Fv" or "Fv fragment" or "Fv region" as used herein is meant a polypeptide that comprises the VL and VH domains of a single antibody.

By "Fc", "Fc domain" or "Fc region", as used herein is meant the polypeptide comprising the constant region of an antibody excluding the first constant region immunoglobulin domain. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM, Fc may include the J chain. For IgG, as illustrated in FIG. 1, Fc comprises immunoglobulin domains Cγ2 and Cγ3 and the hinge between Cγ1 and Cγ2. Although the boundaries of the Fc region may vary, the human IgG heavy chain Fc region is usually defined to comprise residues C226 or P230 to its carboxyl-terminus, wherein the numbering is according to the EU index as in Kabat. Fc may refer to this region in isolation, or this region in the context of an Fc polypeptide, as described below.

By "full length antibody" as used herein is meant the structure that constitutes the natural biological form of an antibody, including variable and constant regions. For example, in most mammals, including humans and mice, the full length antibody of the IgG isotype is a tetramer and consists of two identical pairs of two immunoglobulin chains, each pair having one light and one heavy chain, each light chain comprising immunoglobulin domains VL and CL, and each heavy chain comprising immunoglobulin domains VH, Cγ1, Cγ2, and Cγ3. In some mammals, for example in camels and llamas, IgG antibodies may consist of only two heavy chains, each heavy chain comprising a variable domain attached to the Fc region.

By "amino acid modification" herein is meant an amino acid substitution, insertion, and/or deletion in a polypeptide sequence. The preferred amino acid modification herein is a substitution. By "amino acid modification" herein is meant an amino acid substitution, insertion, and/or deletion in a polypeptide sequence. By "amino acid substitution" or "substitution" herein is meant the replacement of an amino acid at a given position in a protein sequence with another amino acid. For example, the substitution Y50W refers to a variant of a parent polypeptide, in which the tyrosine at position 50 is replaced with tryptophan. A "variant" of a polypeptide refers to a polypeptide having an amino acid sequence that is substantially identical to a reference polypeptide, typically a native or "parent" polypeptide. The polypeptide variant may possess one or more amino acid substitutions, deletions, and/or insertions at certain positions within the native amino acid sequence.

"Conservative" amino acid substitutions are those in which an amino acid residue is replaced with an amino acid residue having a side chain with similar physicochemical properties. Families of amino acid residues having similar side chains are known in the art, and include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine).

An "isolated" molecule is a molecule that is the predominant species in the composition wherein it is found with respect to the class of molecules to which it belongs (i.e., it makes up at least about 50% of the type of molecule in the composition and typically will make up at least about 70%, at least about 80%, at least about 85%, at least about 90%, at least about 95%, or more of the species of molecule, e.g., peptide, in the composition). Commonly, a composition of an antibody molecule will exhibit 98%, 98%, or 99% homogeneity for antibody molecules in the context of all present peptide species in the composition or at least with respect to substantially active peptide species in the context of proposed use.

In the context of the present disclosure, "treatment" or "treating" refers to preventing, alleviating, managing, curing or reducing one or more symptoms or clinically relevant manifestations of a disease or disorder, unless contradicted by context. For example, "treatment" of a patient in whom no symptoms or clinically relevant manifestations of a disease or disorder have been identified is preventive or prophylactic therapy, whereas "treatment" of a patient in whom symptoms or clinically relevant manifestations of a disease or disorder have been identified generally does not constitute preventive or prophylactic therapy.

The term "reactive moiety" herein refers to a moiety that can be coupled with another moiety without prior activation or transformation.

The term "protecting group" refers to a group that temporarily protects or blocks, i e., intended to prevent from reacting, a functional group, e.g., an amino group, a hydroxyl group, or a carboxyl group, during the transformation of a first molecule to a second molecule.

The phrase "moiety that improves the pharmacokinetic properties", when referring to a compound (e.g. an antibody) refers to a moiety that changes the pharmacokinetic properties of the one or more moieties Z in such a way that a better therapeutic or diagnostic effect can be obtained. The moiety can for example increase the water solubility, increase the circulation time, or reduce immunogenicity.

The phrase "linking group" refers to a structural element of a compound that links one structural element of said compound to one or more other structural elements of said same compound.

The phrase "a number representing degree of branching" is used to denote that the subscript number next to a closing bracket represents how many units of the moiety within the brackets are attached to the moiety directly to the left of the corresponding opening bracket. For example, A-(B)$_b$ with b being a number representing a degree of branching means that b units B are all directly attached to A. This means that when b is 2, the formula reduces to B-A-B.

The phrase "a number representing degree of polymerization" is used to denote that the subscript number next to a closing bracket represents how many units of the moiety within the brackets are connected to each other. For example, A-(B)$_1$, with b being a number representing a degree of polymerization means that when b is 2, the formula reduces to A-B-B.

The term "identity" or "identical", when used in a relationship between the sequences of two or more polypeptides, refers to the degree of sequence relatedness between polypeptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988).

Preferred methods for determining identity are designed to give the largest match between the sequences tested. Methods of determining identity are described in publicly available computer programs. Preferred computer program methods for determining identity between two sequences include the GCG program package, including GAP (Devereux et al., Nucl. Acid. Res. 12, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well known Smith Waterman algorithm may also be used to determine identity.

As used herein, "alkyl" refers to a straight or branched hydrocarbon chain that comprises a fully saturated (no double or triple bonds) hydrocarbon group. The alkyl group may have, for example, 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, the term "heteroalkyl" refers to a straight or branched alkyl group that contains one or more heteroatoms, that is, an element other than carbon (including but not limited to oxygen, sulfur, nitrogen, phosphorus) in place of one or more carbon atoms.

Whenever a group is described as being "substituted" that group substituted with one or more of the indicated substituents. If no substituents are indicated, it is meant that the indicated "substituted" group may be substituted with one or more group(s) individually and independently selected from alkyl, alkenyl, alkynyl, cycloalkyl, cycloalkenyl, cycloalkynyl, heteroalkyl, aryl, heteroaryl, heteroalicyclyl, aralkyl, heteroaralkyl, (heteroalicyclyl)alkyl, hydroxy, alkoxy, aryloxy, acyl, mercapto, alkylthio, arylthio, cyano, halogen, thiocarbonyl, carbamyl, thiocarbamyl, amido, sulfonamido, sulfonamido, carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group, and protected derivatives thereof.

Where the number of substituents is not specified (e.g. haloalkyl), there may be one or more substituents present. For example "haloalkyl" may include one or more of the same or different halogens. As another example, "$C_1$-$C_3$ alkoxyphenyl" may include one or more of the same or different alkoxy groups containing one, two or three atoms.

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluensulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

Producing Antibodies

Antibodies may be produced by a variety of techniques known in the art. Typically, they are produced by immunization of a non-human animal, preferably a mouse, with an immunogen comprising a polypeptide, or a fragment or derivative thereof, typically an immunogenic fragment, for which it is desired to obtain antibodies (e.g. a human polypeptide). The step of immunizing a non-human mammal with an antigen may be carried out in any manner well known in the art for stimulating the production of antibodies in a mouse (see, for example, E. Harlow and D. Lane, Antibodies: A Laboratory Manual., Cold Spring Harbor Laboratory Press, Cold Spring Harbor, N.Y. (1988), the entire disclosure of which is herein incorporated by reference). Other protocols may also be used as long as they result in the production of B cells expressing an antibody directed to the antigen used in immunization. Lymphocytes from a non-immunized non-human mammal may also be isolated, grown in vitro, and then exposed to the immunogen in cell culture. The lymphocytes are then harvested and the fusion step described below is carried out. For preferred monoclonal antibodies, the next step is the isolation of splenocytes from the immunized non-human mammal and the subsequent fusion of those splenocytes with an immortalized cell in order to form an antibody-producing hybridoma. The hybridoma colonies are then assayed for the production of antibodies that specifically bind to the polypeptide against which antibodies are desired. The assay is typically a colorimetric ELISA-type assay, although any assay may be employed that can be adapted to the wells that the hybridomas are grown in. Other assays include radioimmunoassays or fluorescence activated cell sorting. The wells positive for the desired antibody production are examined to determine if one or more distinct colonies are present. If more than one colony is present, the cells may be re-cloned and grown to ensure that only a single cell has given rise to the colony producing the desired antibody. After sufficient growth to produce the desired monoclonal antibody, the growth media containing monoclonal antibody (or the ascites fluid) is separated away from the cells and the monoclonal antibody present therein is purified. Purification is typically achieved by gel electrophoresis, dialysis, chromatography using protein A or protein G-Sepharose, or an anti-mouse Ig linked to a solid support such as agarose or Sepharose beads (all described, for example, in the Antibody Purification Handbook, Biosciences, publication No. 18-1037-46, Edition AC, the disclosure of which is hereby incorporated by reference).

Human antibodies may also be produced by using, for immunization, transgenic animals that have been engineered to express a human antibody repertoire (Jakobovitz et Nature 362 (1993) 255), or by selection of antibody repertoires using phage display methods. For example, a XenoMouse (Abgenix, Fremont, Calif.) can be used for immunization. A XenoMouse is a murine host that has had its immunoglobulin genes replaced by functional human immunoglobulin genes. Thus, antibodies produced by this mouse or in hybridomas made from the B cells of this mouse, are already humanized. The XenoMouse is described in U.S. Pat. No. 6,162,963, which is herein incorporated in its entirety by reference.

Antibodies may also be produced by selection of combinatorial libraries of immunoglobulins, as disclosed for instance in (Ward et al. Nature, 341 (1989) p. 544, the entire disclosure of which is herein incorporated by reference). Phage display technology (McCafferty et al (1990) Nature 348:552-553) can be used to produce antibodies from immunoglobulin variable (V) domain gene repertoires from unimmunized donors. See, e.g., Griffith et al (1993) EMBO J. 12:725-734; U.S. Pat. No. 5,565,332; U.S. Pat. No. 5,573,905; U.S. Pat. No. 5,567,610; U.S. Pat. No. 5,229,275). When combinatorial libraries comprise variable (V) domain gene repertoires of human origin, selection from combinatorial libraries will yield human antibodies.

Additionally, a wide range of antibodies are available in the scientific and patent literature, including DNA and/or amino acid sequences, or from commercial suppliers. Examples of antibodies include antibodies that recognize an antigen expressed by a target cell that is to be eliminated, for example a proliferating cell or a cell contributing to a pathology. Examples include antibodies that recognize tumor antigens, microbial (e.g. bacterial) antigens or viral antigens. Other examples include antigens present on immune cells that are contributing to inflammatory or autoimmune disease, including rejection of transplanted tissue (e.g. antigens present on T cells (CD4 or CD8 T cells)).

Antibodies will typically be directed to a pre-determined antigen. As used herein, the term "bacterial antigen" includes, but is not limited to, intact, attenuated or killed bacteria, any structural or functional bacterial protein or carbohydrate, or any peptide portion of a bacterial protein of sufficient length (typically about 8 amino acids or longer) to be antigenic. Examples include gram-positive bacterial antigens and gram-negative bacterial antigens Optionally, the bacterial antigen is derived from a bacterium selected from the group consisting of *Helicobacter* species, in particular *Helicobacter pyloris*; *Borelia* species, in particular *Borelia burgdorferi*; *Legionella* species, in particular *Legionella pneumophilia*; *Mycobacteria* s species, in particular *M. tuberculosis, M. avium, M. intracellulare, M. kansasii, M. gordonae*; *Staphylococcus* species, in particular *Staphylococcus aureus*; *Neisseria* species, in particular *N. gonorrhoeae, N. meningitidis*; *Listeria* species, in particular *Listeria monocytogenes*; *Streptococcus* species, in particular *S. pyogenes, S. agalactiae; S. faecalis; S. bovis, S. pneumonias*; anaerobic *Streptococcus* species; pathogenic *Campylobacter* species; *Enterococcus* species; *Haemophilus* species, in particular *Haemophilus influenzue*; *Bacillus* species, in particular *Bacillus anthracis*; *Corynebacterium* species, in particular *Corynebacterium diphtheriae*; *Erysipelothrix* species, in particular *Erysipelothrix rhusiopathiae*; *Clostridium* species, in particular *C. perfringens, C. tetani*; *Enterobacter* species, in particular *Enterobacter aerogenes*, *Klebsiella* species, in particular *Klebsiella 1S pneumoniae*, *Pasteurella* species, in particular *Pasteurella multocida*, *Bacteroides* species; *Fusobacterium* species, in particular *Fusobacterium nucleatum*; *Streptobacillus* species, in particular *Streptobacillus moniliformis*; *Treponema* species, in particular *Treponema pertenue*; *Leptospira*; pathogenic *Escherichia* species; and *Actinomyces* species, in particular *Actinomyces israeli*.

As used herein, the term "viral antigen" includes, but is not limited to, intact, attenuated or killed whole virus, any structural or functional viral protein, or any peptide portion of a viral protein of sufficient length (typically about 8 amino acids or longer) to be antigenic. Sources of a viral antigen include, but are not limited to viruses from the families: Retroviridae (e.g., human immunodeficiency viruses, such as HIV-1 (also referred to as HTLV-III, LAV or HTLV-III/LAV, or HIV-III; and other isolates, such as HIV-LP); Picornaviridae (e.g., polio viruses, hepatitis A virus; enteroviruses, human Coxsackie viruses, rhinoviruses, echoviruses); Calciviridae (e.g., strains that cause gastroenteritis); Togaviridae (e.g., equine encephalitis viruses, rubella viruses); Flaviviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bunyaviridae (e.g., Hantaan viruses, bunya viruses, phleboviruses and Nairo viruses); Arenaviridae (hemorrhagic fever viruses); Reoviridae (e.g., reoviruses, orbiviruses and rotaviruses); Bornaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and 2), varicella zoster virus, cytomegalovirus (CMV), herpes virus; Poxyiridae (variola viruses, vaccinia viruses, pox viruses); and Iridoviridae (e.g., African swine fever virus); and unclassified viruses (e.g., the agent of delta hepatitis (thought to be a defective satellite of hepatitis B virus)), Hepatitis C; Norwalk and related viruses, and astroviruses). Alternatively, a viral antigen may be produced recombinantly.

As used herein, the terms "cancer antigen" and "tumor antigen" are used interchangeably and refer to antigens (e.g., carbohydrates, polypeptides, or any peptide of sufficient length (typically about 8 amino acids or longer) to be antigenic) that are differentially expressed by cancer cells and can thereby be exploited in order to target cancer cells. Cancer antigens are antigens which can potentially stimulate apparently tumor-specific immune responses. Some of these antigens are encoded, although not necessarily expressed, by normal cells. These antigens can be characterized as those which are normally silent (i.e., not expressed) in normal cells, those that are expressed only at certain stages of differentiation and those that are temporally expressed such as embryonic and fetal antigens. Other cancer antigens are encoded by mutant cellular genes, such as oncogenes (e.g., activated ras oncogene), suppressor genes (e.g., mutant p53), fusion proteins resulting from internal deletions or chromosomal translocations. Still other cancer antigens can be encoded by viral genes such as those carried on RNA and DNA tumor viruses.

The cancer antigens are usually normal cell surface antigens which are either over-expressed or expressed at abnormal times. Ideally the target antigen is expressed only on proliferative cells (preferably tumour cells), however this is rarely observed in practice. As a result, target antigens are usually selected on the basis of differential expression between proliferative and healthy tissue. Antibodies have been raised to target specific tumour related antigens including: Cripto, CD4, CD20, CD30, CD19, CD33, Glycoprotein NMB, CanAg, Her2 (ErbB2/Neu), CD56 (NCAM), CD22 (Siglec2), CD33 (Siglec3), CD79, CD138, CD171, PSCA, PSMA (prostate specific membrane antigen), BCMA, CD52, CD56, CD80, CD70, E-selectin, EphB2, Melanotransferin, Mud 6 and TMEFF2. Examples of cancer antigens also include B7-H3, B7-H4, B7-H6, PD-L1, MAGE, MART-1/Melan-A, gp100, adenosine deaminase-binding protein (ADAbp), cyclophilin b, colorectal associated antigen (CRC)-C017-1A/GA733, carcinoembryonic antigen (CEA) and its immunogenic epitopes CAP-1 and CAP-2, etv6, aml1, prostate specific antigen (PSA), T-cell receptor/CD3-zeta chain, MAGE-family of tumor antigens, GAGE-family of tumor antigens, BAGE, RAGE, LAGE-1, NAG, GnT-V, MUM-1, CDK4, MUC family, VEGF, VEGF receptors, PDGF, TGF-alpha, EGF, EGF receptor, a member of the human EGF-like receptor family such as HER-2/neu, HER-3, HER-4 or a heterodimeric receptor comprised of at least one HER subunit, gastrin releasing peptide receptor antigen, Muc-1, CA125, αvβ3 integrins, α5β1 integrins, αIIbβ3-integrins, PDGF beta receptor, SVE-cadherin, IL-8, hCG, IL-6, IL-6 receptor, IL-15, α-fetoprotein, E-cadherin, α-catenin, ß-catenin and γ-catenin, p120ctn, PRAME, NY-ESO-1, cdc27, adenomatous polyposis coli protein (APC), fodrin, Connexin 37, Ig-idiotype, p15, gp75, GM2 and GD2 gangliosides, viral products such as human papillomavirus proteins, imp-1, P1A, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, and c-erbB-2, although this is not intended to be exhaustive.

DNA encoding an antibody of interest can be placed in an appropriate expression vector for transfection into an appropriate host. The host is then used for the recombinant production of the antibody, or variants thereof, such as a humanized version of that monoclonal antibody, active fragments of the antibody, chimeric antibodies comprising the antigen recognition portion of the antibody, or versions comprising a detectable moiety.

In certain embodiments, the DNA of a hybridoma or other cell producing an antibody can be modified prior to insertion into an expression vector, for example, by substituting the coding sequence for human heavy- and light-chain constant domains in place of the homologous non-human sequences (e.g., Morrison et al., PNAS pp. 6851 (1984)), or by covalently joining to the immunoglobulin coding sequence all or part of the coding sequence for a non-immunoglobulin polypeptide. In that manner, "chimeric" or "hybrid" antibodies are prepared that have the binding specificity of the original antibody. Typically, such non-immunoglobulin polypeptides are substituted for the constant domains of an antibody disclosed herein.

Humanized antibodies can also be prepared. Humanized antibodies are typically specific chimeric immunoglobulins, immunoglobulin chains or fragments thereof (such as Fv, Fab, Fab', F (ab') 2, "dab", or other antigen-binding subsequences of antibodies) which contain minimal sequence derived from the murine immunoglobulin. For the most part, humanized antibodies are human immunoglobulins (recipient antibody) in which residues from a complementary-determining region (CDR) of the recipient are replaced by residues from a CDR of the original antibody (the parent or donor antibody) while maintaining the desired specificity, affinity, and capacity of the original antibody. The CDRs of the parent antibody, some or all of which are encoded by nucleic acids originating in a non-human organism, are grafted in whole or in part into the beta-sheet framework of a human antibody variable region to create an antibody, the specificity of which is determined by the engrafted CDRs. The creation of such antibodies is described in, e.g., WO 92/11018, Jones, 1986, Nature 321:522-525, Verhoeyen et al., 1988, Science 239:1534-1536.

The antibody may or may not further comprise at least a portion of an immunoglobulin constant region (Fc), typically that of a human immunoglobulin. For further details see Jones et al., Nature, 321, pp. 522 (1986); Reichmann et al, Nature, 332, pp. 323 (1988); Presta, Curr. Op. Struct. Biol., 2, pp. 593 (1992); Verhoeyen et Science, 239, pp. 1534; and U.S. Pat. No. 4,816,567, the entire disclosures of which are herein incorporated by reference.

Wild-type full-length IgG antibodies of human isotype will possess a conserved acceptor glutamine at residue 295 (EU numbering as in Kabat) of the heavy chain which when in non-glycosylated form will be accessible to a TGase and therefore reactive with a compound of Formula Ia or Ib in the presence of a TGase, under suitable conditions, to form a conjugate from the antibody (e.g. a composition of antibodies of Formula II, IVa or IVb). The antibody will lack glycosylation at the asparagine at residue 297 of the heavy chain.

Additional or alternative sites reactive with a compound of Formula I in the presence of a TGase can be created by engineering the antibodies. The compounds disclosed herein include glutamine engineered antibodies where one or more amino acids of a wild-type or parent antibody are replaced with (substituted by) a glutamine amino acid, or where a glutamine residue, optionally together with other amino acid residues, is introduced or added to a wild-type or parent antibody (e.g. wherein the glutamine residue is added to an antibody fragment).

It should be noted that a single site mutation that provides a glutamine that is accessible to a TGase may yield more than one engineered glutamine residue that can be conjugated if the antibody comprises more than one engineered chain. For example, a single site mutation will yield two engineered glutamine residues in a tetrameric IgG due to the dimeric nature of the IgG antibody. The engineered glutamine residues will be in addition to any acceptor glutamine already present in an antibody, if any. The glutamine amino acid residues that are reactive, in the presence of a TGase under suitable conditions, with a compound of Formula I may be located in the heavy chain, typically in the constant domain.

In one embodiment, an asparagine at amino acid position 297 (EU Index) is substituted with a glutamine residue. The antibody will have a constant region with a N297Q substitution (a N297Q variant antibody). An antibody having a N297Q substitution and a glutamine at residue 295 (EU Index) will therefore have two acceptor glutamines and thus two conjugation sites per heavy chain. In tetravalent form will therefore have four conjugates per antibody. Such an antibody will be particularly well adapted for use in conjunction with the methods disclosed herein; the antibody can be reacted with a compound of Formula I.

In one embodiment an antibody may have a constant region with a Q295X (e.g., Q295X/N297Q), N297X, S298X and/or T299X substitution (a Q295X, N297X, S298X and/or T299X variant antibody), wherein X is any amino acid (other than a glutamine or the residue Q, N, S or T naturally present at the respective 297, 298 or 299 residue), optionally wherein the substitution is a conservative substitution. An antibody having a Q295X will be understood to have an introduced glutamine at a different position, e.g., the antibody will also have a N297Q substitution. Such an antibody, when comprising a glutamine at position 295 (a glutamine is naturally present in human constant regions at position 295) but no other acceptor glutamine residues, will have two conjugates per antibody when the antibody comprises two heavy chains.

An advantageous approach for preparing conjugated antibodies can comprise providing as starting materials antibodies lacking N297-linked glycosylation (such N-linked glycosylation interferes with TGase coupling onto residue 295), wherein the +2 position relative to an acceptor glutamine is a non-aspartic acid residue. The residue at the +2 position can be any suitable amino acid that permits efficient TGase-mediated conjugation. Optionally, the residue at the +2 position is a non-negatively charged amino acid, e.g. any electrically neutral amino acid, a serine, etc. Optionally, the residue at the +2 position is selected from the group consisting of: amino acids with positively charged side chains, amino acids with polar uncharged side chains, and amino acids with hydrophobic side chains.

One approach for preparing antibodies comprising a functionalized acceptor glutamine residue flanked at position +2 by a non-aspartic acid residue is to prepare antibodies having an asparagine at position 297 but lacking N-linked glycosylation by a suitable method that does not transform the asparagine at residue 297 to an aspartic acid. For example, antibodies can be produced in a host cell (e.g. a prokaryotic cell, E. coli) that does not yield N-glycosylated antibodies. Such antibodies will typically have a glutamine in their heavy chain at position 295 and a non-glycosylated asparagine at position 297, i.e. the residue at the +2 position relative to an acceptor glutamine is an asparagine.

Preparing antibodies comprising a functionalized acceptor glutamine residue flanked at the +2 position by a non-aspartic acid residue can also be achieved by protein engineering. For example, an antibody having a glutamine naturally present at heavy chain residue 295 (EU numbering) can comprise a modification at residue 297 such that the asparagine is deleted or replaced by a different amino acid. Advantageously, the asparagine at amino acid position 297 is substituted with a non-glutamine, non-aspartic acid residue (e.g., a non-negatively charged amino acid, any conservative substitution, an amino acid with a positively charged side chain, an amino acid with a polar uncharged side chain, an amino acid with a hydrophobic side chain, e.g. a serine). The antibody will thus have a constant region with a N297X substitution (a N297X variant antibody), wherein X is any amino acid other than asparagine, glutamine or aspartic acid.

In another example, an antibody having a glutamine naturally present at heavy chain residue 295 and an asparagine at residue 297 (EU numbering) can comprise a modification at residues 295 and 297 such that the glutamine at residue 295 is deleted or replaced by a different amino acid (e.g., a non-negatively charged amino acid and the asparagine at residue 297 is replaced by a glutamine which then serves as the acceptor glutamine). The antibody will thus have a constant region with Q295X and N297Q substitutions (a Q295X N297Q variant antibody), wherein X is any amino acid other than glutamine, optionally wherein the substitution is a non-negatively charged amino acid.

In another example, an antibody having an acceptor glutamine (e.g. a glutamine naturally present at heavy chain residue 295) and an asparagine at residue 297 (EU numbering) comprises a modification at a non-297 residue (a residue that is not at position 297, EU numbering) in an Fc domain (e.g. CH1, CH2 and/or CH3 domain), wherein the modification abrogates N297-linked glycosylation. Such an antibody will have an acceptor glutamine (e.g. at residue 295) together with an aglycosylated asparagine at residue 297. For example, modifications leading to elimination of asparagine-linked glycosylation at N297 include a substitution at residue T299 (or optionally additional substitutions at other residues, e.g. substitutions at both T299 and S298), see, e.g., any of the mutations and combinations of mutations disclosed in Sazinsky et al. 2008 Proc. Nat. Acad. Sci. U.S.A. 105(51):20167-20172. An exemplary antibody can thus have a constant region with a T299X substitution (a T299X variant antibody), wherein X is an amino acid other than threonine, wherein the modification abrogates N297-linked glycosylation.

It will be appreciated that the methods disclosed herein can also be used to couple antibodies with acceptor glutamines in positions other than 295 or 297. An acceptor glutamine can be naturally present in an antibody or can be introduced into an antibody (e.g. a substitution in a CH2 or CH3 domain, a single amino acid substitution or insertion, insertion of a TGase recognition tag comprising an acceptor glutamine). The location of the glutamine residue may be varied according to the size and nature of the antibody required. For example, a variable region domain of an antibody can be covalently attached at a C-terminal amino acid to at least one other antibody domain or a fragment thereof which contains, or is attached to one or more acceptor glutamine residues. Thus, for example where a VH domain is present in the variable region domain this may be linked to an immunoglobulin constant domain or a fragment thereof. In one example the TGase recognition tag is fused to the C-terminus of a heavy chain CH3 domain or to the C-terminus of a light chain Cκ or Cλ domain of a tetrameric (e.g. full-length) antibody or of an antibody fragment. In one example the TGase recognition tag is introduced to (e.g. by modifying one or more amino acid residues of the antibody) a CH2 or CH3 domain of a heavy chain of a tetrameric (e.g. full-length) antibody or of an antibody fragment. In one example the fragment may be a Fab fragment wherein the antigen binding domain contains associated VH and VL domains covalently linked at their C-termini to a CH1 and CK domain respectively. The CH1 domain may be extended with further amino acids, for example to provide a hinge region domain as found in a Fab' fragment, or to provide further domains, such as antibody CH2 and CH3 domains. In one example, a polypeptide "tag" comprising one or a plurality (e.g. 2, 3, 4, 5, 6) non-glutamine residues and a glutamine residue attached directly to a C-terminal amino acid of a full or truncated CH1, CH2 or CH3 domain, or to a C-terminal amino acid of a full or truncated CK domain.

Engineered antibodies can be prepared by a variety of methods which include, but are not limited to, isolation from a natural source (in the case of naturally occurring amino acid sequence variants), preparation by site-directed (or oligonucleotide-mediated) mutagenesis (Carter (1985) et al Nucleic Acids Res. 13:4431-4443; Ho et al (1989) Gene (Amst.) 77:51-59; Kunkel et al (1987) Proc. Natl. Acad. Sci. USA 82:488; Liu et al (1998) J. Biol. Chem. 273:20252-20260), PCR mutagenesis (Ito et al (1991) Gene 102:67-70; and Vallette et al (1989) Nuc. Acids Res. 17:723-733) and cassette mutagenesis (Wells et al (1985) Gene 34:315-323) of an earlier prepared DNA encoding the polypeptide. Mutagenesis protocols, kits, and reagents are commercially available, e.g. QuikChange® Multi Site-Direct Mutagenesis Kit (Stratagene, La Jolla, Calif.). Single mutations are also generated by oligonucleotide directed mutagenesis using double stranded plasmid DNA as template by PCR based mutagenesis (Sambrook and Russel, (2001) Molecular Cloning: A Laboratory Manual, 3rd edition). Variants of recombinant antibodies may be constructed also by restriction fragment manipulation or by overlap extension PCR with synthetic oligonucleotides. Mutagenic primers encode the cysteine codon replacement(s). Standard mutagenesis techniques can be employed to generate DNA encoding such mutant cysteine engineered antibodies (Sambrook et al Molecular Cloning, A Laboratory Manual. Cold Spring Harbor Laboratory Press, Cold Spring Harbor, N.Y., 1989; and Ausubel et al Current Protocols in Molecular Biology, Greene Publishing and Wiley-Interscience, New York. N.Y., 1993).

Antibodies may be chemically synthesized using known oligopeptide synthesis methodology or may be prepared and purified using recombinant technology. In vitro protein synthesis may be performed using manual techniques or by automation.

Fragments and derivatives of antibodies (which are encompassed by the term "antibody" or "antibodies" as used in this application, unless otherwise stated or clearly contradicted by context), can be produced by techniques that are known in the art. "Fragments" comprise a portion of the intact antibody, generally the antigen binding site or variable region. Examples of antibody fragments include Fab, Fab', Fab'-SH, F(ab')2, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv molecules (2) single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multispecific antibodies formed from antibody fragments. Included, inter alia, are a nanobody, domain antibody, single domain antibody or a "dAb".

The DNA of a hybridoma producing an antibody may be modified so as to encode a fragment. The modified DNA is then inserted into an expression vector and used to transform or transfect an appropriate cell, which then expresses the desired fragment.

The full-length antibody or the antibody fragment will comprise a variable region domain that will generally be covalently attached to at least one, two or more glutamine residue covalently linked through a —NH—(C)$_n$—X-L moiety (and optionally further a V and/or Y moiety, optionally further an R or RR' moiety, to a moiety-of-interest Z, e.g. a polymer molecule, a drug, a radioactive moiety. The variable region will comprise hypervariable region or CDR sequences, and FR sequences.

Lysine-Based Linkers

A linking reagent comprising a primary amine that functions as a TGase substrate for conjugation onto an acceptor glutamine of an antibody can be used to conjugate any desired moiety of interest onto the antibody. For example a lysine derivative (Lys), including but not limited to a lysine amino acid residue, or a functional equivalent thereof, can further comprise (e.g. be connected to) a moiety of interest such that upon conjugation, the moiety-of-interest-containing linker is covently bound to the acceptor glutamine of the antibody. In one embodiment, a moiety that improves the pharmacokinetic properties, a therapeutic moiety or a diagnostic moiety, and optionally one or more other groups, are attached to the linking reagent.

In another embodiment, a multi-step conjugation process can be used to link a moiety that improves the pharmacokinetic properties, a therapeutic moiety or a diagnostic moiety to an antibody. In this configuration, a linker may comprise a reactive group (R) or a plurality of reactive groups, preferably non-complementary reactive groups, and the antibody-linker conjugate is formed which is thereafter reacted with a compound comprising a complementary reactive group (R') and a moiety that improves the pharmacokinetic properties, a therapeutic moiety or a diagnostic moiety. The reactive group is preferably a functionality that is insensitive to water but selectively undergoes a very high conversion addition reaction with a complementary reagent. The reactive group may be a group that is large, charged and/or hydrophobic (e.g. cyclic groups, cycloalkynes).

The lysine derivative can be a 2 to 20 alkyl or heteroalkyl chain, or a functional equivalent thereof, with an H$_2$N, H$_2$NOCH$_2$, H$_2$NCH$_2$ (aminomethylene) group or a protected H$_2$N, H$_2$NOCH$_2$, H$_2$NCH$_2$ group positioned at one or more ends of the alkyl or heteroalkyl chain. The heteroalkyl chain can be a chain of 3 to 20 atoms where one or more non-terminal atoms can be other than carbon, for example oxygen, sulfur, nitrogen, or other atoms. The oxygen, sulfur, or nitrogen atom can be of an ether, ester, thioether, thioester, amino, alkylamino, amido or alkylamido functionality within the carbon chain.

The heteroalkyl chain can be an oligo (ethylene oxide) chain. The functionality within the alkyl or heteroalkyl chain can be included to couple the reactive group to the H$_2$N, H$_2$NOCH$_2$, H$_2$NCH$_2$ group or protected H$_2$N, H$_2$NOCH$_2$, H$_2$NCH$_2$ group. The alkyl or heteroalkyl chain can be substituted or unsubstituted. The substituents can be alkyl groups, aryl groups, alkyl aryl groups, carboxylic acid groups, amide groups, hydroxy groups, or any other groups that do not compete with the amino group for, or inhibit, conjugation with a glutamine residue of the protein. Typically, when a substituent is present, its presence is in a convenient starting material, such as the carboxylic acid group of lysine, from which the lysine derivative results. The H$_2$N, H$_2$NOCH$_2$, H$_2$NCH$_2$ end of a alkyl or heteroalkyl chain is necessarily included in the linking reagent.

Exemplary starting materials for the functional equivalent of lysine can be an α,ω-diaminoalkane, for example, 1,2-diaminoethane, 1,3-diaminopropane, 1,4-diaminobutane, 1,5-diaminopentane, 1,6-diaminohexane, 1,7-diaminoheptane, 1,8-diaminooctane, 1,9-diaminononane, 1,10-diaminodecane, 1,11-diaminoundecane, or 1,12-diaminododecane. Other starting materials for the functional equivalent of a lysine derivative can be α,ω-diamino oligo (ethylene oxide), for example, H$_2$N(CH$_2$CH$_2$O)$_x$CH$_2$CH$_2$NH$_2$ where x is 1 to about 6. The α,ω-diamino oligo (ethylene oxide) can be a single oligomer or it can be a mixture of oligomers where x defines an average size. An exemplary protected H$_2$NCH$_2$ is the tert-butylcarbamate protected amine of tert-butyl N-(5-aminopentyl)carbamate (N-Boc-cadaverin).

The linking reagent, a pharmaceutically acceptable salt or solvate thereof, or an antibody-conjugated linking reagent may comprise the general Formula Ia or Ib. Formulae Ia (having an Z group) and Ib (having a R group) are shown as follows:

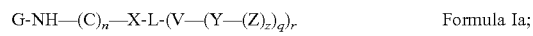
G-NH—(C)$_n$—X-L-(V—(Y—(Z)$_z$)$_q$)$_r$      Formula Ia;

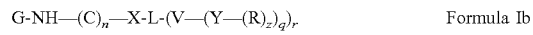
G-NH—(C)$_n$—X-L-(V—(Y—(R)$_z$)$_q$)$_r$      Formula Ib or a pharmaceutically acceptable salt or solvate thereof wherein:

G is an H, amine protecting group, or an immunoglobulin (Ab) attached via an amide bond;

(C)$_n$ is a substituted or unsubstituted alkyl or heteroalkyl chain, optionally where the carbon adjacent to the nitrogen is unsubstituted, optionally wherein any carbon of the chain is substituted alkoxy, hydroxyl, alkylcarbonyloxy, alkyl-S—, thiol, alkyl-C(O)S—, amine, alkylamine, amide, or alkylamide (e.g. with a O, N or S atom of an ether, ester, thioether, thioester, amine, alkylamine, amide, or alkylamide);

n is an integer selected from among the range of 2 to 20, preferably 3 to 6;

X is NH, O, S, or absent;

L is a bond or a carbon comprising framework of 1 to 200 atoms substituted at one or more atoms, optionally wherein the carbon comprising framework is a linear hydrocarbon, a symmetrically or asymmetrically branched hydrocarbon, monosaccharide, disaccharide, linear or branched oligosaccharide (asymmetrically branched or symmetrically branched), an amino acid, a di-, tri-, tetra-, or oligopeptide, other natural linear or branched oligomers (asymmetrically branched or symmetrically branched), or a dimer, trimer, or higher oligomer (linear, asymmetrically branched or symmetrically branched) resulting from any chain-growth or step-growth polymerization process;

r is an integer selected from among 1, 2, 3 or 4;

q is an integer selected from among 1, 2, 3 or 4; and z is an integer selected from among 1, 2, 3 or 4;

V is independently absent, a bond or a continuation of a bond if L is a bond, a non-cleavable moiety or a conditionally-cleavable moiety, optionally following prior conditional transformation, which can be cleaved or transformed by a chemical, photochemical, physical, biological, or enzymatic process (e.g. cleavage of V ultimately leading to release of one or more moieties subsequently or ultimately linked to V, for example a Z moiety). In some embodiments, V is, preferably, a di-, tri-, tetra-, or oligopeptide as described below in the section entitled "The V Moiety";

Y is independently absent, a bond or a continuation of a bond if V is a bond or continuation of a bond, or a spacer system (e.g., a self-eliminating spacer system or a non-self-elimination spacer system) which is comprised of 1 or more spacers;

Z is a moiety that improves the pharmacokinetic properties, a therapeutic moiety or a diagnostic moiety; and R is a reactive moiety, preferably a moiety comprising an unprotected or protected thiol, maleimide, haloacetamide, o-phoshenearomatic ester, azide, fulminate, alkyne, cyanide, anthracene, 1,2,4,5-tetrazine, norbornene, other stained or otherwise electronically activated alkene or, optionally, a protected or unprotected amine when X is absent and L, V, or Y is other than a bond or a continuation of a bond. In an alternative embodiment R is a reactive moiety, preferably a moiety comprising an unprotected or protected thiol, an unprotected or protected amine, maleimide, haloacetamide, o-phoshenearomatic ester, azide, fulminate, alkyne, cyanide, anthracene, 1,2,4,5-tetrazine, norbornene, other stained or otherwise electronically activated alkene, provided that R is not an amine when n=5 and X, L, V and Y are absent.

The $(C)_n$ group may for example be a straight, branched and/or cyclic $C_{2-30}$ alkyl, $C_{2-30}$ alkenyl, $C_{2-30}$ alkynyl, $C_{2-30}$ heteroalkyl, $C_{2-30}$ heteroalkenyl, $C_{2-30}$ heteroalkynyl, optionally wherein one or more homocyclic aromatic compound radical or heterocyclic compound radical may be inserted; notably, any straight or branched $C_{2-5}$ alkyl, $C_{5-10}$ alkyl, $C_{11-20}$ alkyl, $-O-C_{1-5}$ alkyl, $-O-C_{5-10}$ alkyl, $-O-C_{11-20}$ alkyl, $CH_2-(CH_2-O-CH_2)_{1-12}-CH_2$ or $(CH_2-CH_2-O-)_{1-12}$, an amino acid, an oligopeptide, glycan, sulfate, phosphate or carboxylate.

In one example the $(C)_n$ group is a carbon comprising framework substituted with one or more O atoms. In one embodiment, the carbon adjacent to the nitrogen is substituted with an O atom. In one embodiment, the carbon adjacent to the nitrogen is unsubstituted. In one embodiment, the $(C)_n$ group is or comprises an ethylene oxide group, e.g. a $CH_2-(CH_2-O-CH_2)_n-CH_2$ group or an $(CH_2-CH_2-O-)_n$, where n is an integer from 1 to 10.

The L group can be a carbon comprising framework, where L is a linear hydrocarbon, a symmetrically or asymmetrically branched hydrocarbon, monosaccharide, disaccharide, linear or branched oligosaccharide (asymmetrically branched or symmetrically branched), an amino acid, a di-, tri-, tetra-, or oligopeptide, other natural oligomer, dimer, trimer, or higher oligomer (linear asymmetrically branched or symmetrically branched) resulting from any chain-growth or step-growth polymerization process. For example, L may comprise or be a straight, branched and/or cyclic $C_{2-30}$ alkyl, $C_{2-30}$ alkenyl, $C_{2-30}$ alkynyl, $C_{2-30}$ heteroalkyl, $C_{2-30}$ heteroalkenyl, $C_{2-30}$ heteroalkynyl, optionally wherein one or more homocyclic aromatic compound radical or heterocyclic compound radical may be inserted; notably, any straight or branched $C_{2-5}$ alkyl, $C_{5-10}$ alkyl, $C_{11-20}$ alkyl, $-O-C_{1-5}$ alkyl, $-O-C_{5-10}$ alkyl, $-O-C_{11-20}$ alkyl, $CH_2-(CH_2-O-CH_2)_{1-30}-CH_2$ or $(CH_2-CH_2-O-)_{1-30}$, e.g., $(CH_2-CH_2-O-)_{12}$, $(CH_2-CH_2-O-)_{1-24}$, an amino acid, an oligopeptide, glycan, sulfate, phosphate, carboxylate. Optionally, L is absent.

L, V and/or Y have r, q, and/or z sites of attachment for the respective V, Y, and Z or R groups, where r and q represent the degree of branching or polymerization. The sites of attachment can comprise a bond or comprise a functional group selected from an alkene, alkyne, ether, thioether, ester, thioester, amine, amide, alkylamide, or other functional group readily generated by a condensation or addition reaction.

In one example the carbon comprising framework of the L group is optionally substituted with one or more O atoms. In one embodiment, the L group comprises one or more ethylene oxide groups ($CH_2-O-CH_2$). Optionally, the L group comprises a carbon framework comprising a $(CH_2-CH_2-O-)_n$ group, wherein n is an integer selected among the range of 1 to 10 (e.g., 1, 2, 3, 4, 5, 6, 7, 8, 9 or 10).

In Formulae Ia, Ib, II, IVa and IVb, the linking group L links the aminopeptidyl moiety $-NH-(C)_n-X$ to the reactive group R or Z, optionally through one or more V and/or Y moieties where present. L may be a bond connecting V, Y, R or Z directly to the aminopeptidyl moiety. In another aspect, however, L is a linking group that functionally links or spaces the one or more moieties V and/or Y reactive moiety R or moiety of interest (Z). In Formulae Ib, Ic, II and IVb, spacing improves efficiency and completion of BTGase coupling, make additionally the reactive moiety R more accessible to the reaction partner, for example when the reactive moiety is present on a lysine-based linker and coupled to the antibody and then brought into contact with a reaction partner. In Formulae Ia and IVa, the linking group L links the aminopeptidyl moiety $-NH-(C)_n-X$ to the moiety-of-interest (Z), optionally through one or more V and/or Y moieties where present. L may be a bond connecting V, Y or Z directly to the aminopeptidyl moiety. In another aspect, however, L is a linking group that functionally links or spaces the one or more moieties V and/or Y reactive moiety Z. In Formulae Ia and IVa, spacing improves efficiency and completion of BTGase coupling, providing for highly homogenous compounds. In antibodies comprising a functionalized acceptor glutamine of Formula IVa or IVb spacing may also provide for a better accessibility of V, which in the case of enzymatic cleavage or transformation of V, may improve the rate at which V is transformed and/or cleaved.

L and $(C)_n$ groups can be configured based on the overall structure of the linker that is to be used. Particularly when a multi-step method is used and the linker (e.g. the linker of Formula Ia or Ib is free of or does not comprise a large, charged or hydrophobic moiety (e.g. a cyclic, polycyclic or macrocyclic moiety), the L group may be a bond or a shorter carbon framework. For example, L may represent or comprise a carbon framework of 1, 2, 3, 4, 5, or 6 linear carbon atoms, unsubstituted or optionally substituted at one or more atoms. Preferably, where L additionally comprises other groups, the 5-20 linear carbon atoms will be adjacent to the $(C)_n$ group, or where present, the X group.

When a linker (e.g. the linker of Formula Ia or Ib or an antibody of Formula II, IVa or IVb) comprises a large, charged or hydrophobic moiety (e.g. a cyclic, polycyclic or macrocyclic moiety), for example, wherein V, Y and/or Z comprises a large, charged or hydrophobic moiety (e.g. a cyclic, polycyclic or macrocyclic moiety), the L group may be longer carbon framework. For example, L may represent or comprise a carbon framework of:

a) 2-30 linear carbon atoms optionally substituted at one or more atoms;

b) 2-15 linear carbon atoms optionally substituted at one or more atoms;

c) 5-20 linear carbon atoms optionally substituted at one or more atoms;

d) 5-30 linear carbon atoms optionally substituted at one or more atoms;

e) 5-15 linear carbon atoms optionally substituted at one or more atoms; or f) 4, 5 or 6 linear carbon atoms optionally substituted at one or more atoms.

Preferably, the 5-20 linear carbon atoms will be adjacent to (the continuation of) the $(C)_n$ group, or where present, the X group.

In some embodiments, L is a —(C=O)—$C_{1-6}$ alkyl group. In some embodiments, L is a $C_{1-6}$ alkoxy-$C_{1-6}$ alkyl group. In some embodiments, L is a —(C=O)—$C_{1-6}$ alkoxy-$C_{1-6}$ alkyl group. In some embodiments, L is a —(C=O)—$C_{10-20}$ alkyl group. In some embodiments, L is a $C_{1-6}$ alkyl group. In some embodiments, L is a $C_{10-20}$ alkyl group. In some embodiments, L is a —(C=O)—O—$C_{1-6}$ alkyl group. In some embodiments, L is a —(C=O)—O—$C_{2-20}$ alkyl group. In some embodiments, L is a —(C=O)— group. In some embodiments, L is selected from among —(C=O)—$CH_2$—S—

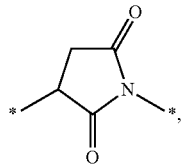

—(C=O)—$CH_5$—S—

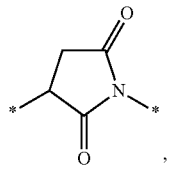 [SMILES: *C1CC(=O)N(*)C1=O]

and —$CH_2$—($CH_2$—O—$CH_2$)$_4$—$CH_2$—S—

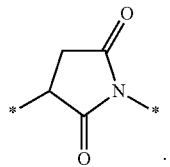 [SMILES: *C1CC(=O)N(*)C1=O]

In some embodiments, L is or comprises an amino acid or a di-, tri- tetra- or oligopeptide. In some embodiments, L is selected from among alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, and citrulline.

In any of the compounds (e.g. in any of Formula I, II and/or IV), linking element (L) can optionally be characterized as having a chain length of at least 2.8 Angstroms, 3, Angstroms, 4 Angstroms, 5 Angstroms, 10 Angstroms, 15 Angstroms, 18 Angstroms, 30 Angstroms, 40 Angstroms or 60 Angstroms. Optionally L has a length of no more than 100 Angstroms, optionally no more than 60 Angstroms Optionally, L is characterized as having a length of between 2.8, 3, 4, 5, 10, 20 or 30 Angstroms and 60 Angstroms. Optionally, L is characterized as having a length of between 2.8 and 19 Angstroms, or between 4 and 19 Angstroms.

Examples of compounds of Formula Ia include but are not limited to compound having the $(C)_n$, X, L, V, Y and Z groups shows in Table 2 herein. Examples of compounds of Formula Ib include but are not limited to compound having the $(C)_n$, X, L, V, Y and R groups shows in Table 3 herein. R groups in Table 3 indicated as (S) can also be S(C=O)$CH_3$ when present as a protected reactive group. The symbol (-) in the tables indicates that the particular X, L, V or Y moiety is absent. V and Y groups, for example, can comprise any structural features in the sections titled "The V Moiety" and "The Y Moiety" herein. The L, V and/or Y groups of Formulae Ia and Ib represented in each of Tables 2 and 3 can have r, q, and/or z sites of attachment for the respective V, Y, and R or Z groups, where r and q represent the degree of branching or polymerization; r, q, and/or z can be selected from 1, 2, 3 or 4.

A compound may contain more than one L moiety. Any L' moiety can be defined in the same way as a L moiety. The L moieties may or may not be the same. The linking group L may be a water-soluble moiety or contain one or more water-soluble moieties, such that L contributes to the water solubility of a compound of Formula (I)-(VI). An L may also be a moiety or contain one or more moieties that reduce(s) aggregation, which may or may not be a moiety/moieties that also increase(s) the water solubility.

L may be for example a linear linker or a branched linker. In one aspect, the L moiety is branched, optionally further a dendritic structure, so that it can be connected to at least two, three, four or more V, Y or R moieties (or Z where applicable). Each V—Y moiety is however only attached once to an L moiety. Branching can occur at one or more branching atoms that may for example be carbon, nitrogen, silicon, or phosphorus.

Any one of the L moieties disclosed herein can be utilized in Formula Ia, Ib, II, IVa, and IVb. Any one of the L moieties described herein can be used in combination with any of the $(C)_n$, X, V, Y, Z, R, M, z, q, and r groups described herein. Any one of the L' moieties disclosed herein can be utilized in Formula III. Any one of the L' moieties described herein can be used in combination with any of the R', V', Y', Z, z', q', and r' groups described herein.

Exemplary linkers of Formula Ia include but are not limited to:

Compound Ia-1

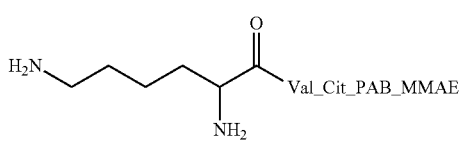

-continued
Compound Ia-2
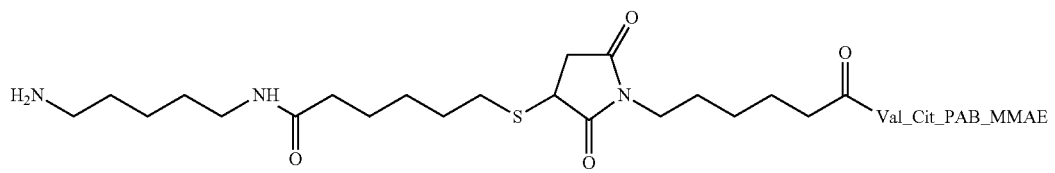
Compound Ia-3
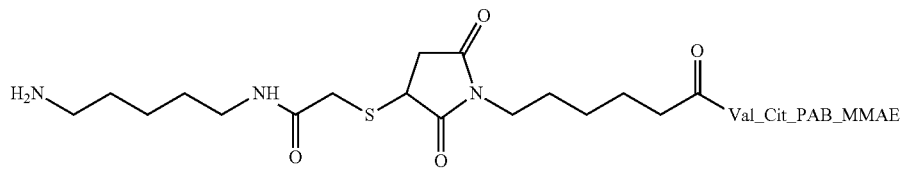
Compound Ia-4
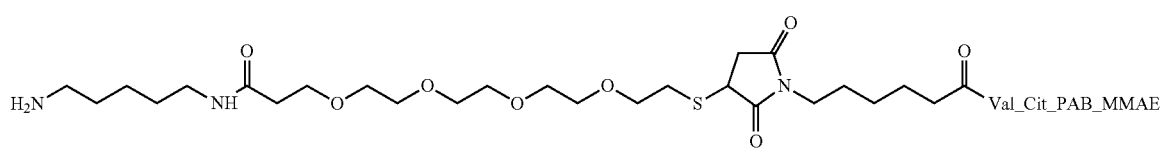
Compound Ia-5
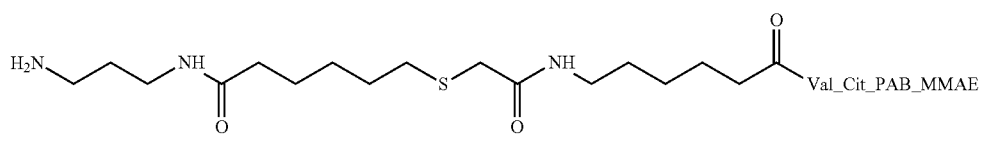
Compound Ia-6
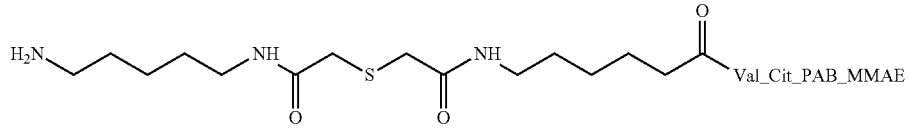
Compound Ia-7
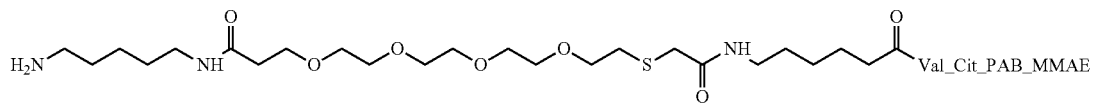
Compound Ia-8
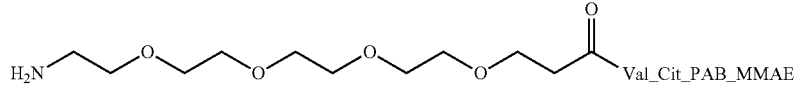
Compound Ia-9
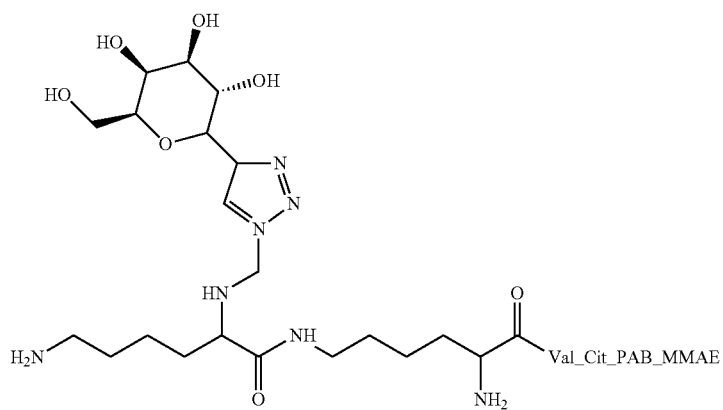

Compound Ia-10
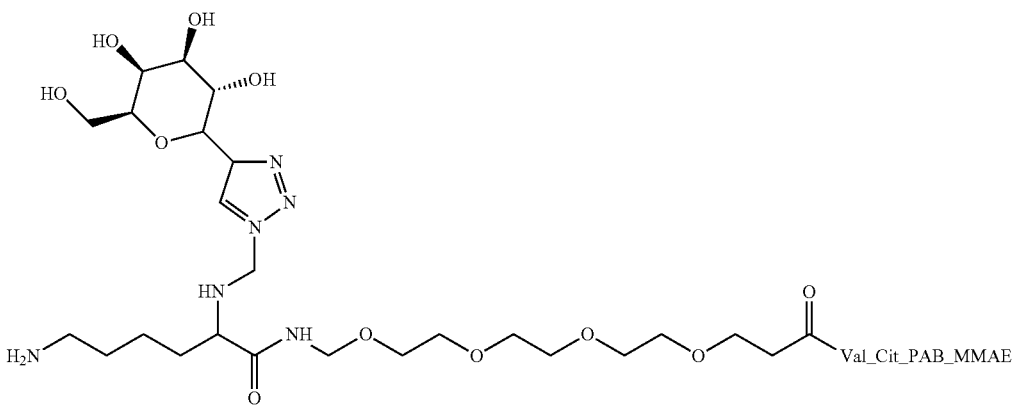
Compound Ia11
Compound Ia-12
Compound Ia-13
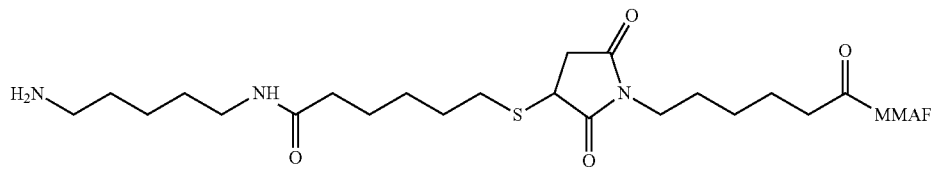
Compound Ia-14
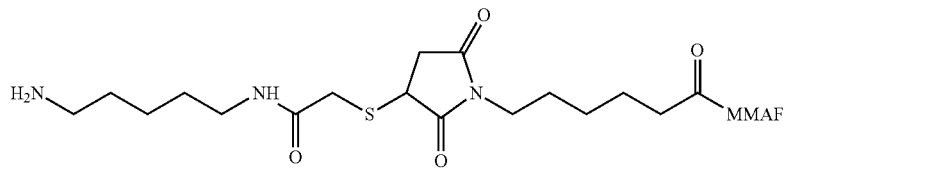
Compound Ia-15
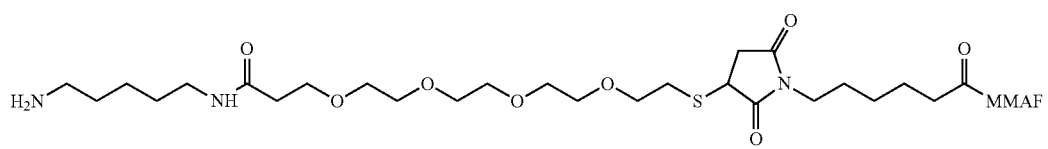
Compound Ia-16
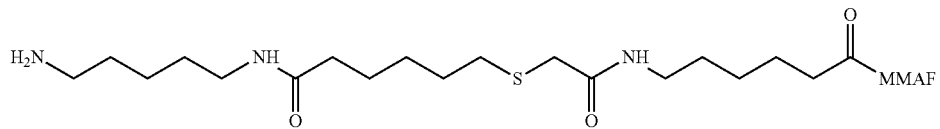
Compound Ia-17
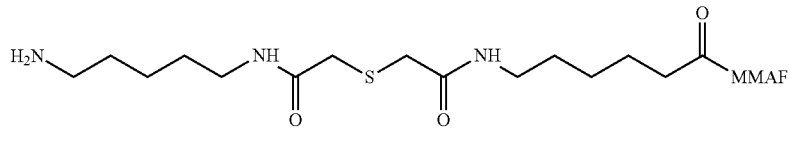
Compound Ia-18
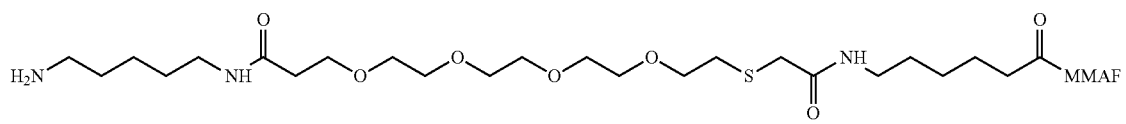
Compound Ia-19
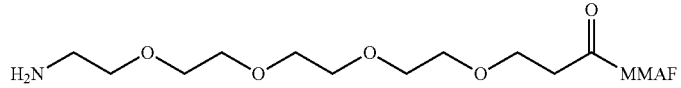

-continued
Compound Ia-20
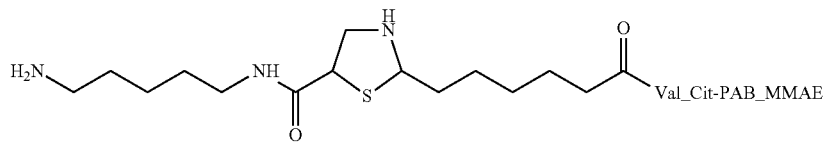
Compound Ia-21
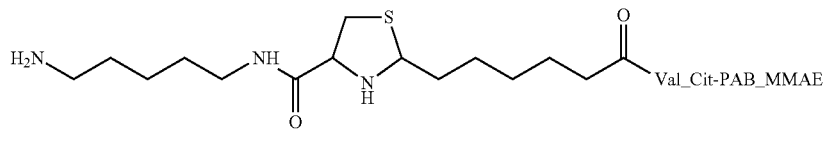
Compound Ia-22
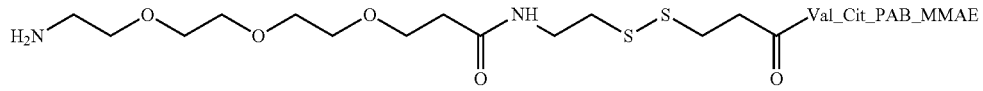
Compound Ia-23
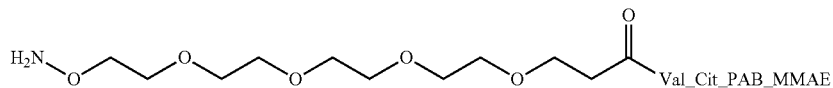
Exemplary linkers of Formula Ib include but are not limited to:
Compound Ib-1
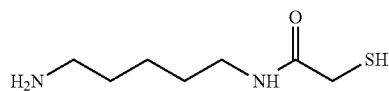
Compound Ib-2
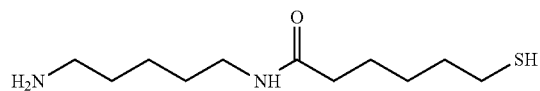
Compound Ib-3
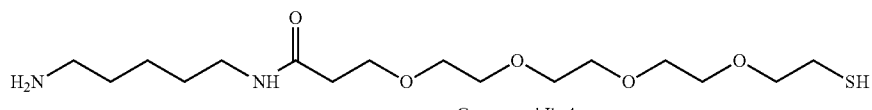
Compound Ib-4
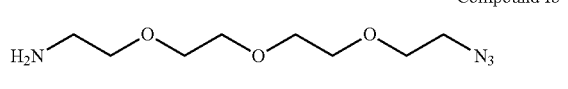
Compound Ib-5
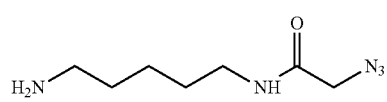
Compound Ib-6
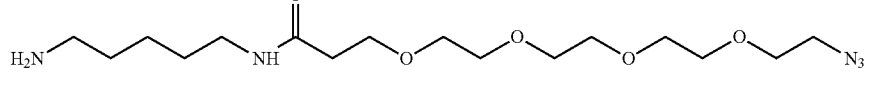
Compound Ib-7
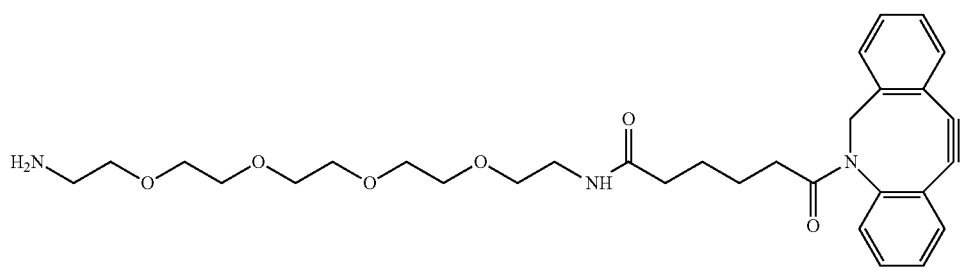
Compound Ib-8
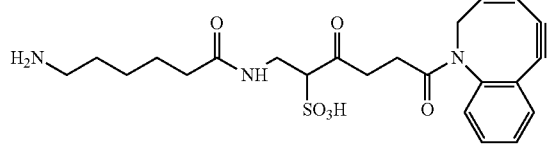
Compound Ib-9
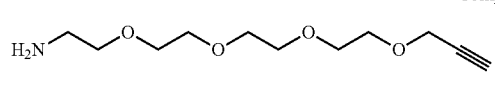

Compound Ib-10

Compound Ib-11

Compound Ib-12

Compound Ib-13

Compound Ib-14

Compound Ib-15

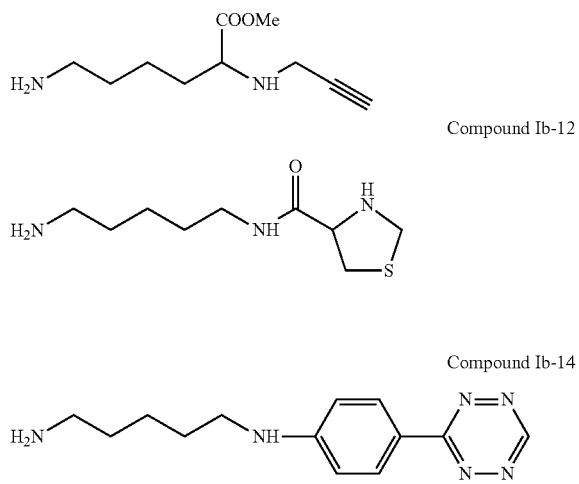
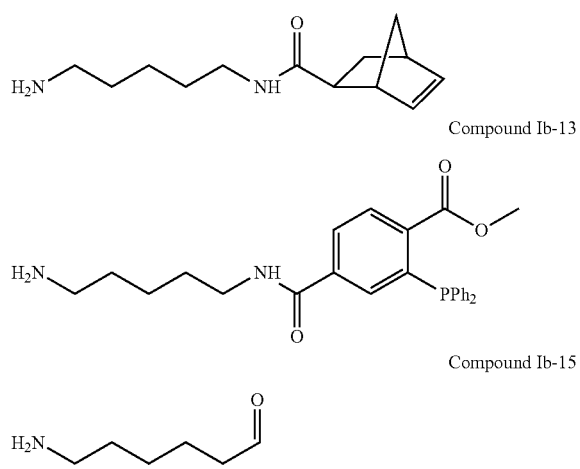

The V Moiety

The V moiety may be incorporated in the lysine-based linker (e.g. connected to L, optionally through Y). However, the V moiety may instead or in addition be incorporated in a compound comprising a moiety-of-interest Z (e.g. a compound R'—V—Y—Z of formula III) that will be reacted with an antibody conjugated with a lysine-based linker to form an antibody conjugated to the moiety-of-interest Z. Any V' moiety can be defined in the same way as a V moiety.

The V moiety is a group that is either non-cleavable or conditionally cleavable, optionally after prior conditional transformation. In the latter case, it is designed to be transformed and/or cleaved from Y, or Z when Y is absent, by a chemical, photochemical, physical, biological, or enzymatic process, e.g. in certain conditions. This condition may for example comprise bringing a compound into an aqueous environment, which leads to hydrolysis of V, or bringing a compound of the disclosure into an environment that contains an enzyme that recognizes and cleaves V, or bringing a compound under reducing conditions, which leads to reduction of V, or bringing a compound into contact with radiation, e.g., UV light, which leads to transformation and/or cleavage, or bringing a compound into contact with heat, which leads to transformation and/or cleavage, or bringing a compound under reduced pressure or bringing a compound under elevated or high pressure, which leads to transformation and/or cleavage. This condition may further be met after administrating a compound to an animal, e.g., a mammal: the condition may be met when the compound localizes to for example a specific organ, tissue, cell, subcellular target, or microbial target, for example by the presence of internal factors (e.g., target-specific enzymes or hypoxia) or application of external factors (e g., radiation, magnetic fields) or the condition may already be met directly upon administration (e.g., enzymes). In general, transformation of V will directly or indirectly lead to cleavage of V from Y, or Z when Y is absent. It may occur that two or more separate transformations and/or cleavages, requiring the same or different conditions, are required in order to cleave V completely from Y or Z. In this way, increased selectivity may be obtained. A compound may contain more than one V moiety. These V moieties may or may not be the same and may or may not require the same conditions for transformation and/or cleavage.

V may comprise for example a carbon comprising framework of 1 to 200 atoms, optionally a carbon comprising framework of at least 10 atoms, e.g. 10 to 100 atoms or 20 to 100 atoms, substituted at one or more atoms, optionally wherein the carbon comprising framework is a linear hydrocarbon or comprises a cyclic group, a symmetrically or asymmetrically branched hydrocarbon, monosaccharide, disaccharide, linear or branched oligosaccharide (asymmetrically branched or symmetrically branched), other natural linear or branched oligomers (asymmetrically branched or symmetrically branched), an amino acid, a di-, tri-, tetra-, or oligopeptide, or more generally any dimer, trimer, or higher oligomer (linear, asymmetrically branched or symmetrically branched) resulting from any chain-growth or step-growth polymerization process.

Generally, V may be any straight, branched and/or cyclic $C_{2-30}$ alkyl, $C_{2-30}$ alkenyl, $C_{2-30}$ alkynyl, $C_{2-30}$ heteroalkyl, $C_{2-30}$ heteroalkenyl, $C_{2-30}$ heteroalkynyl, optionally wherein one or more homocyclic aromatic compound radical or heterocyclic compound radical may be inserted; notably, any straight or branched $C_{2-5}$ alkyl, $C_{5-10}$ alkyl, $C_{11-20}$ alkyl, —O—$C_{1-5}$ alkyl, —O—$C_{5-10}$ alkyl, —O—$C_{11-20}$ alkyl, or ($CH_2$—$CH_2$—O—)$_{1-24}$ or ($CH_2$)$_{x1}$—($CH_2$—O—$CH_2$)$_{1-24}$—($CH_2$)$_{x2}$— group, wherein x1 and x2 are independently an integer selected among the range of 0 to 20, an amino acid, an oligopeptide, glycan, sulfate, phosphate, or carboxylate. Optionally, V may be or absent. In some embodiments, V is a $C_{2-6}$ alkyl group.

In one aspect, a compound is used to target one or more therapeutic and/or diagnostic moieties Z to target cells. In this instance, V may for example contain a substrate molecule that is cleaved by an enzyme present in the vicinity of the target cells or inside the target cells, for example tumor cells. V can for example contain a substrate that is cleaved by an enzyme present at elevated levels in the vicinity of or inside the target cells as compared to other parts of the body, or by an enzyme that is present only in the vicinity of or inside the target cells.

If target cell specificity is achieved solely based upon the selective transformation and/or cleavage of V at the target site, the condition (eventually) causing the cleavage should preferably, at least to a certain degree, be target cell-specific, whereas the presence of another target-specific moiety in the compound, for instance when the antibody recognizes an antigen present on a target cell with a degree of specificity, reduces or takes away this requirement. For example, when an antibody causes specific internalization into a target cell, an enzyme also present in other cells may transform and/or cleave V. In one embodiment, transformation and/or cleavage of V occurs intracellularly. In another embodiment, transformation and/or cleavage of V occurs extracellularly.

In one embodiment, the V moiety is a conditionally cleavable moiety.

In one embodiment, V contains a di-, tri-, tetra-, or oligopeptide which consists of an amino acid sequence recognized by a protease, for example plasmin, a cathepsin, cathepsin B, prostate-specific antigen (PSA), urokinase-type plasminogen activator (u-PA), or a member of the family of matrix metalloproteinases, present in the vicinity of or inside the target cells, for example tumor cells. In one embodiment V may be a dipeptide, tripeptide, tetrapeptide, or oligopeptide moiety comprised of natural L amino acids, unnatural D amino acids, or synthetic amino acids, or a peptidomimetic, or any combination thereof. In one embodiment, V is a peptide. In another embodiment, V is a dipeptide. In another embodiment, V is a tripeptide. In another embodiment, V is a tetrapeptide. In yet another embodiment, V is a peptidomimetic.

In one embodiment, V contains a substrate for an enzyme.

In another embodiment, V contains a beta-glucuronide that is recognized by beta-glucuronidase present in the vicinity of or inside tumor cells.

In one embodiment, V contains a substrate for an extracellular enzyme. In another embodiment, V contains a substrate for an intracellular enzyme.

In yet another embodiment, V contains a substrate for a lysosomal enzyme.

In yet another embodiment, V contains a substrate for the serine protease plasmin.

In yet another embodiment, V contains a substrate for one or more of the cathepsins, for example cathepsin B. When V is cleaved extracellularly, the one or more Z moieties may be released extracellularly. This may provide the advantage that these Z moieties are not only able to affect or detect the cell(s) directly surrounding the site of activation, but also cells somewhat further away from the site of activation due to diffusion (bystander effect).

In one embodiment V comprises a tripeptide. The tripeptide may be linked via its C-terminus to Y. In one embodiment, the C-terminal amino acid residue of the tripeptide is selected from arginine, citrulline, and lysine, the middle amino acid residue of the tripeptide is selected from alanine, valine, leucine, isoleucine, methionine, phenylalanine, cyclohexylglycine, tryptophan and proline, and the N-terminal ammo acid residue of the tripeptide is selected from any natural or unnatural amino acid.

In another embodiment V comprises a dipeptide. The dipeptide may be linked via its C-terminus to Y. In one embodiment, the C-terminal amino acid residue of the dipeptide is selected from alanine, arginine, citrulline, and lysine, and the N-terminal amino acid residue of the dipeptide is selected from any natural or unnatural amino acid. In one embodiment, V is selected from phenylalanine-lysine and valine-citrulline.

An example of a linker comprising a lysine residue as $(C)_n$ moiety and a valine-citrulline as the (V) moiety is shown below:

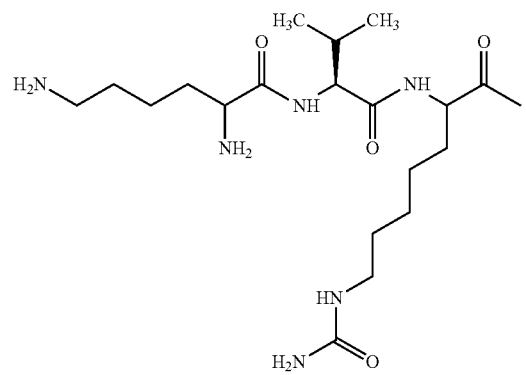 [SMILES: CC(=O)C(CCCCCNC(N)=O)NC(=O)[C@@H](NC(=O)C(N)CCCCN)C(C)C]

Optionally, the di-, tri-, tetra, or oligopeptide(s) comprise or consist or amino acids with non-negatively charged side chains (amino acids other than aspartic acid or glutamic acid). Optionally, the di-, tri-, tetra, or oligopeptide(s) comprise or consist or amino acids selected from: amino acids with positively charged side chains, amino acids with polar uncharged side chains, and amino acids with hydrophobic side chains.

In another aspect, a compound is used to improve the pharmacokinetic properties of Z. V may in this case for example be or contain a group that is cleaved by ubiquitous enzymes, e.g., esterases that are present in the circulation, by pH-controlled intramolecular cyclization, or by acid-catalyzed, base-catalyzed, or non-catalyzed hydrolysis, or V may for example be or contain a disulfide. V may therefore, optionally together with the connecting atom of L and/or Y (or Z if Y is absent), for example form a carbonate, carbamate, urea, ester, amide, imine, hydrazone, oxime, disulfide, acetal, or ketal group. It is understood that V can also be or contain such a moiety and/or be transformed and/or cleaved in the same or a similar way when a compound is used for other purposes than solely improving the pharmacokinetic properties of Z.

When the compounds are used for other purposes, e.g., an ex vivo diagnostic assay, V may be or contain any of the moieties mentioned above and transformation and/or cleavage of V may occur by any one of the processes mentioned above or by any other functional transformation or cleavage process known to a person skilled in the art. For example, in a diagnostic assay, V may be cleaved or transformed by an enzyme, by reduction, or below, above, or at a certain pH.

When V is conditionally cleavable, the compounds are designed to eventually release at least one Z after cleavage and optional prior transformation of V. Release of Z via another mechanism is however not excluded.

In any embodiment, V may contain a blocking group to prevent premature transformation and/or cleavage of V before the condition is met under which V is designed to be transformed and/or cleaved.

In another aspect, V is a moiety that is non-cleavable. This means that V cannot be cleaved from Y, or Z when Y is absent, under the conditions the compound containing such a V moiety is designed to be applied, meaning that Z cannot be released in this way.

Release of Z via another mechanism is however not excluded. When V is a non-cleavable moiety, Y may optionally be absent. A non-cleavable V moiety may be any moiety that cannot be cleaved, or that can be cleaved only very slowly, under the conditions the compound containing such a V moiety is designed to be applied, e.g. in vivo or in vitro.

For example, when applied in vivo, V will not or only very slowly be cleaved by enzymes present in the in vivo model used or by hydrolysis or as a consequence of other biological processes that may occur in said model. Such V may therefore, optionally together with the connecting atom of L and/or Z, for example, be a carbonyl group, an amide group, an urea group, an ester group, a carbonate group, a carbamate group, or an optionally substituted methyleneoxy or methyleneamino group V may be preferred to be non-cleavable when it is not required that the one or more moieties Z are released. This may for example be the case when Z does not require to become released before it can exert its therapeutic or diagnostic properties.

In one embodiment V is connected to L via a functional group in the side chain of one of the natural or unnatural amino acids. In another embodiment, the N-terminal amino acid of V is connected via its alpha amino group to L.

Any one of the V moieties disclosed herein can be utilized in Formula Ia, Ib, Ic, II, IVa and IVb. Any one of the V moieties described herein can be used in combination with any of the $(C)_n$, X, L, R, Y, Z, M, z, q, and r groups described herein. Any one of the V' moieties disclosed herein can be utilized in Formula III. Any one of the V' moieties described herein can be used in combination with any of the R', V', Y', Z, z', q', and r' groups described herein.

The Spacer System Y

The spacer system Y, when present, links V and optionally L to one or more moieties R, and following reaction with a compound of Formula III, a moiety-of-interest Z. In one embodiment, Y is absent. In another embodiment, Y is a self-elimination spacer system. A spacer system Y may be incorporated in a compound for example to improve the properties of Z or the compound in general, to provide suitable coupling chemistries, or to create space between V and Z. Any Y' moiety can be defined in the same way as a Y moiety.

Spacer system Y may comprise for example a carbon comprising framework of 1 to 200 atoms, optionally a carbon comprising framework of at least 10 atoms, e.g. 10 to 100 atoms or 20 to 100 atoms, substituted at one or more atoms, optionally wherein the carbon comprising framework is a linear hydrocarbon or comprises a cyclic group, a symmetrically or asymmetrically branched hydrocarbon, monosaccharide, disaccharide, linear or branched oligosaccharide (asymmetrically branched or symmetrically branched), other natural linear or branched oligomers (asymmetrically branched or symmetrically branched), an amino acid, a di-, tri-, tetra-, or oligopeptide, or more generally any dimer, trimer, or higher oligomer (linear, asymmetrically branched or symmetrically branched) resulting from any chain-growth or step-growth polymerization process.

Y may be any straight, branched and/or cyclic $C_{2-30}$ alkyl, $C_{2-30}$ alkenyl, $C_{2-30}$ alkynyl, $C_{2-30}$ heteroalkyl, $C_{2-30}$ heteroalkenyl, $C_{2-30}$ heteroalkynyl, optionally wherein one or more homocyclic aromatic compound radical or heterocyclic compound radical may be inserted; notably, any straight or branched $C_{2-5}$ alkyl, $C_{5-10}$ alkyl, $C_{11-20}$ alkyl, —O—$C_{1-5}$ alkyl, —O—$C_{5-10}$ alkyl, —O—$C_{11-20}$ alkyl, or $(CH_2—CH_2—O—)_{1-24}$ or $(CH_2)_{x1}—(CH_2—O—CH_2)_{1-24}—(CH_2)_{x2}—$ group, wherein x1 and x2 are independently an integer selected among the range of 0 to 20, an amino acid, an oligopeptide, glycan, sulfate, phosphate, or carboxylate. Optionally, Y is absent. In some embodiments, Y is a $C_{2-6}$ alkyl group.

A compound may contain more than one spacer system Y. These moieties Y may or may not be the same. In some embodiments the spacer system Y is a self-elimination spacer that is connected to one or more other self-elimination spacers via a direct bond. Herein, a single self-elimination spacer may also be referred to as a spacer system. A spacer system may be branched or unbranched and contain one or more attachment sites for Z as well as V. Self-elimination spacers that are able to release only a single moiety are called 'single release spacers'. Self-elimination spacers that are able to release two or more moieties are called 'multiple release spacers'. Spacers, may be either branched or unbranched and self-eliminating through a 1,2+2n-elimination (n>/=1), referred to as "electronic cascade spacers". Spacers may eliminate through a cyclization process under formation of a cyclic urea derivative, referred to as "ω-amino aminocarbonyl cyclization spacers".

The spacer system Y may self-eliminating or non-self-eliminating. A "self-eliminating" spacer unit allows for release of the drug moiety without a separate hydrolysis step. When a self-eliminating spacer is used, after cleavage or transformation of V, the side of Y linked to V becomes unblocked, which results in eventual release of one or more moieties Z. The self-elimination spacer systems may for example be those described in WO 02/083180 and WO 2004/043493, which are incorporated herein by reference in their entirety, as well as other self-elimination spacers known to a person skilled in the art. In certain embodiments, a spacer unit of a linker comprises a p-aminobenzyl unit. In one such embodiment, a p-aminobenzyl alcohol is attached to an amino acid unit via an amide bond, and a carbamate, methylcarbamate, or carbonate is made between the benzyl alcohol and a cytotoxic agent. In one embodiment, the spacer unit is p-aminobenzyloxycarbonyl (PAB). Examples of self-eliminating spacer units further include, but are not limited to, aromatic compounds that are electronically similar to p-aminobenzyl alcohol (see, e.g. US 2005/0256030 A1), such as 2-aminoimidazol-5-methanoi derivatives (Hay et al. (1999) Bioorg. Med. Chem. Lett. 9:2237) and ortho- or para-aminobenzylacetals. Spacers can be used mat undergo cyclization upon amide bond hydrolysis, such as substituted and unsubstituted 4-aminobutyric acid amides (Rodrigues et al. Chemistry Biology, 1995, 2, 223) and 2-aminophenyl-propionic acid amides (Amsberry, et al., J. Org. Chem., 1990, 55. 5867). Elimination of amine-containing drugs that are substituted at the a-position of glycine (Kingsbury, et al., J. Med. Chem., 1984, 27, 1447) are also examples of self-immolative spacers.

A "non-self-eliminating" spacer unit is one in which part or all of the spacer unit remains bound to the moiety Z upon enzymatic (e.g., proteolytic) cleavage of the antibody-moiety-of-interest conjugate. Examples of non-self-eliminating spacer units include, but are not limited to, a glycine spacer unit and a glycine-glycine spacer unit. Other combinations of peptidic spacers susceptible to sequence-specific enzymatic cleavage are also contemplated. For example, enzymatic cleavage of an antibody-moiety-of-interest conjugate containing a glycine-glycine spacer unit by a tumor-cell associated protease would result in release of a glycine-glycine-drug moiety from the remainder of the antibody-moiety-of-interest conjugate. In one such embodiment, the glycine-glycine-drug moiety is then subjected to a separate hydrolysis step in the tumor cell, thus cleaving the glycine-glycine spacer unit from the drug moiety.

A spacer system Y may be connected to more than one V moiety. In this case, transformation and/or cleavage of one of these V moieties may trigger the release of one or more Z moieties. When V moieties that are transformed or cleaved under different conditions are connected to the same Y, release of one or more Z moieties may occur when a compound is brought under one of several different conditions.

Any one of the Y moieties disclosed herein can be utilized in Formula Ia, Ib, II, IVa and IVb. Any one of the Y moieties described herein can be used in combination with any of the $(C)_n$, X, L, V, Y, R, Z, M, z, q, and r groups described herein. Any one of the Y' moieties disclosed herein can be utilized in Formula III. Any one of the Y' moieties described herein can be used in combination with any of the R', L', V', Z, z', q', and r' groups described herein.

In any of the compounds and formulae, the order of V and Y (or V' and Y') can be reversed. The —(V)—(Y)— unit in any of the formulae herein may alternatively be expressed in the reversed arrangement as —(Y)—(V)—.

The Moiety Z

The moieties Z can be connected to Y or Y' or, when absent, to V or V', or, when absent, to L or, when absent to X, or when absent to $(C)_n$. Connections to Y, V or L may optionally be via R or RR'. Connection may be via any suitable atoms. In one embodiment, Z is coupled via oxygen (from for example a hydroxyl group or carboxyl group), carbon (from for example a carbonyl group), nitrogen (from for example a primary or secondary amino group), or sulfur (from for example a sulfhydryl group). In one embodiment, Z is coupled in the compounds via a group such that its therapeutic abilities or diagnostic characteristics are, at least partly, blocked or masked. In case a compound is to be used for treating or preventing disease in an animal, e.g., a mammal, the Z moieties are generally therapeutic moieties. In case a compound is used to make a diagnosis or used in an ex vivo or in vivo diagnostic assay, the Z moieties are generally diagnostic moieties, for example chromogenic, fluorogenic, phosphorogenic, chemiluminescent, or bio luminescent compounds.

In one embodiment, the Z moiety is compound, preferably an organic compound, having a molecular weight of at least 300 g/mol, 400 g/mol, 500 g/mol, 600 g/mol, 700 g/mol, 800 g/mol, 900 g/mol, 1000 g/mol or 2000 g/mol.

In one embodiment, the Z moiety is a chemical compound displaying hydrophobic properties, optionally additionally having a molecular weight of at least 300 g/mol, 400 g/mol, 500 g/mol, 600 g/mol, 700 g/mol, 800 g/mol, 900 g/mol. 1000 g/mol or 2000 g/mol. Hydrophobic character may be determined, for example, by decreased water solubility, decreased polarity, decreased potential for hydrogen bonding, and/or an increased oil/water partition coefficient. The presently disclosed methods can be used to produce antibody conjugates where moiety of interest (Z) comprises a hydrophobic drug. As used herein, the term "hydrophobic" is a physical property of a molecule that is repelled from a mass of water. Hydrophobic compounds can be solubilized in nonpolar solvents, including but not limited to, organic solvents. Hydrophobicity can be conferred by the inclusion of apolar or nonpolar chemical groups that include, but are not limited to, saturated and unsaturated aliphatic hydrocarbon groups and such groups substituted by one or more aromatic, cycloaliphatic or heterocyclic group(s). Conversely, "hydrophilic" molecules are capable of hydrogen bonding with a water molecule and are therefore soluble in water and other polar solvents. The terms "hydrophilic" and "polar" can be used interchangeably. Hydrophilic characteristics derive from the presence of polar or charged groups, such as carbohydrates, phosphate, carboxylic, sulfato, amino, sulfhydryl, nitro, hydroxy and other like groups.

Hydrophobic molecules are poorly water soluble, for example, having a solubility of less than about 10 mg/ml. In some embodiments, the hydrophobic compound can have a solubility of less than about 1 mg/ml in water. In other embodiments, the hydrophobic compound has solubility in water of less than about 50, µg/ml, 10 µg/ml, and in particular embodiments, about 1 µg/ml or 2.5 µg/ml. In other embodiments, the hydrophobic compound can have a solubility of about 0.001 µg/ml to about 10 mg/ml, including but not limited to 0.001 µg/ml, 0.01 µg/ml, 0.1 µg/ml, 1 µg/ml, 2 µg/ml, 5 µg/ml, 10 µg/ml, 50 µg/ml, 100 µg/ml, 500 µg/ml, 1 mg/ml, 5 mg/ml, and 10 mg/ml, and any other concentration between 0.001 µg/ml and 10 mg/ml.

Representative, non-limiting examples of hydrophobic drugs that can be formulated using the presently disclosed methods include taxanes, e.g. paclitaxel (PTX), and camptothecin (CPT), maytansanoids, duocarmycins, dolastatins and auristatins. Such drugs are poorly soluble in water, e.g. PTX has a solubility in water of less than about 1 µg/ml, CPT has a water solubility of about 2.5 µg/ml. Linkers and modified antibodies can advantageously link hydrophobic drugs to antibodies.

In other embodiments, in view of hydrophobic drugs being poor substrates for TGase (in the absence of improved linkers or modified antibodies), the Z moiety may advantageously be a hydrophilic drug. Examples of hydrophilic drugs include amatoxins.

Amatoxins are cyclic peptides composed of 8 amino acids as isolated from the genus *Amanita*. Amatoxins also include a range of chemical derivatives, semisynthetic analogs and synthetic analogs built from building blocks according to the master structure of the −5 natural compounds (cyclic, 8 aminoacids), synthetic or semisynthetic analogs containing non-hydroxylated amino acids instead of the hydroxylated amino acids, synthetic or semisynthetic analogs, in which the thioether sulfoxide moiety is replaced by a sulfide, sulfone, or by atoms different from sulfur, e.g. a carbon atom as in a carbaanalog of amanitin. Functionally, amatoxins are defined as peptides or depsipeptides that inhibit mammalian RNA polymerase II. Preferred amatoxins are those with a functional group (e.g. a carboxylic group, an amino group, a hydroxy group, a thiol or a thiol-capturing group) that can be reacted with linker molecules or proteins. Amatoxins are described for example in European Patent publication no. 1859811, PCT publication nos. WO2010/115630 and WO2012/041504.

In one embodiment, the Z moiety is a large compound (e.g., molecular weight of at least 300 g/mol, 400 g/mol, 500 g/mol, 600 g/mol or 700 g/mol) comprising a polycyclic group, tricycle or one or more macrocycles. Such groups are often typical of hydrophobic and/or rigid structures. Examples of cytotoxic drugs that comprise a macrocycle (e.g. a ring of nine or more atoms) include maytansinoids, amatoxins, epothilones and taxanes. In one embodiment, the Z moiety comprises a ring of 9, 10, 11, 12, 13, 14, 15, 16, 17 or 18 atoms, or between 9 and 200 atoms. In one embodiment, the Z moiety is a chemical compound having a negative charge, optionally additionally displaying hydrophobic properties and/or having a molecular weight of at least 300 g/mol, 400 g/mol, 500 g/mol, 600 g/mol, 700 g/mol, 800 g/mol, 900 g/mol, 1000 g/mol or 2000 g/mol.

When more than one Z moiety is connected to a self-elimination spacer system Y or Y', at least one Z should be released upon self-elimination of Y or Y'. The moiety Z initially released may be a moiety that is not a fully active moiety itself. In other words, Z may be a moiety that has limited diagnostic or therapeutic abilities, e.g. a moiety that acts as a prodrug. Such a Z moiety may require further processing or metabolism, e.g., hydrolysis, enzymatic cleavage, or enzymatic modification (for example phosphorylation, reduction, or oxidation) in order to become fully active. In one embodiment, such further processing is intentionally designed for Z to for example allow Z to reach its final target or cross a biological barrier, e.g., a cell membrane or a nuclear membrane, before it is fully activated. Z may for example contain a hydrophobic moiety that enables Z to cross a cell membrane. This hydrophobic moiety may then be hydrolyzed or removed in any other way intracellularly.

In one aspect, a Z moiety may be a backbone (e.g. polymer) to which a plurality of drugs or diagnostic moieties are linked. For example, Z may be a polyacetal- or polyacetal derivative-based polymer comprising a plurality of drug molecules, see, e.g., Yurkovetskiy et al. (2004) Mol. Pharm. 1(5): 375-382 and WO 2011/120053, the disclosures of which are incorporated herein by reference; for example Z may be a polymer compound of Formula I of WO 2011/120053 comprising a plurality of cytotoxic anti-cancer agents.

In one aspect, one or more moieties Z are each selected from a therapeutic or diagnostic agent.

In another embodiment, one or more moieties Z are each a therapeutic agent. In another embodiment, all moieties Z are each a therapeutic agent.

In yet another embodiment, the moieties Z each are the same therapeutic moiety.

In yet another embodiment, the moieties Z comprise at least two different therapeutic moieties.

The moiety Z includes, for example, antineoplastic agents, drugs, toxins (such as enzymatically active toxins of bacterial or plant origin and fragments thereof e.g. ricin and fragments thereof) biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy.

In one embodiment, the one or more moieties Z are each independently chosen from an antibiotic, an anti-bacterial agent, an antimicrobial agent, an anti-inflammatory agent, an anti-infectious disease agent, an anti-autoimmune disease agent, an anti-viral agent, or an anticancer agent, preferably a cytotoxic anti-cancer agent.

In another embodiment, the one or more moieties Z are each an anticancer agent. In a further embodiment, the one or more moieties Z are each a hydroxyl-containing anticancer agent.

In one embodiment, Z is an alkylating agent, preferably a DNA alkylating agent. An alkylation agent is a compound that can replace a hydrogen atom with an alkyl group under physiological conditions (e.g. pH 7.4, 37 C, aqueous solution). Alkylation reactions are typically described in terms of substitution reactions by N, O and S heteroatomic nucleophiles with the electrophilic alkylating agent, although Michael addition reactions are also important. Examples of alkylating agents include nitrogen and sulfur mustards, ethylenimines, methanosulfonates, CC-1065 and duocarmycins, nitrosoureas, platinum-containing agents, agents that effectuate Topoisomerase II-mediated site dependent alkylation of DNA (e.g. psorospermin and related bisfuranoxanthones), ecteinascidin and other or related DNA minor groove alkylation agents.

In one embodiment, Z is a DNA minor groove binding and/or alkylating agent, e.g, a pyrrolobenzodiazepine, a duocarmycin, or derivatives thereof.

In a further embodiment, the one or more moieties Z are each independently selected from the group consisting of taxanes, anthracyclines, camptothecins, epothilones, mytomycins, combretastatins, vinca alkaloids, nitrogen mustards, maytansinoids, calicheamycins, duocarmycins, tubulysins, dolastatins and auristatins, enediynes, amatoxins, pyrrolobenzodiazepines, ethylenimines, radioisotopes, therapeutic proteins and peptides, and toxins or fragments thereof.

In a further embodiment, the one or more moieties Z are each independently selected from cyclophosphamide, ifosfamide, chlorambucil, 4-(bis(2-chloroethyl)amino)phenol, 4-(bis(2-fluoroethyl)ammo)phenol, N,N-bis(2-chloroethyl)-p-phenylenediamine, N,N-bis(2-fluoro-ethyl)-p-phenylenediamine, carmustine, lomustine, treosulfan, dacarbazine, cisplatin, carboplatin, vincristine, vinblastine, vindesine, vinorelbine, paclitaxel, docetaxel, etoposide, teniposide, topotecan, inirotecan, 9-aminocamptothecin, 9-nitrocamptothecin, 10-hydroxycamptothecin, lurtotecan, camptothecin, crisnatol, mitomycin C, mitomycin A, methotrexate, trimetrexate, mycophenolic acid, tiazofurin, ribavirin, hydroxyurea, deferoxamine, 5-fluorouracil, floxuridine, doxifluridine, raltitrexed, cytarabine, cytosine arabinoside, fludarabine, 6-mercaptopurine, thioguanine, raloxifen, megestrol, goserelin, leuprolide acetate, flutamide, bicalutamide, vertoporfin, phthalocyanine, photosensitizer Pc4, demethoxy-hypocrellin A, interferon-alpha, interferon-gamma, tumor necrosis factor, lovastatin, staurosporine, actinomycin D, bleomycin A2, bleomycin B2, peplomycin, daunorubicin, doxorubicin, N-(5,5-diacetoxypentyl)doxorubicin, morpholino doxorubicin, idarubicin, epirubicin, pirarubicin, zorubicin, mitoxantrone, thapsigargin, $N^8$-acetyl-spermidine, tallysomycin, esperamycin, butyric acid, retinoic acid, I,8-dihydroxybicyclo[7.3.1]trideca-4-ene-2,6-diyne-13-one, anguidine, podophyllotoxin, combretastatin A-4, pancratistatin, tubulysin A, tubulysin D, carminomycin, streptonigrin, elliptmium acetate, maytansine, maytansinol, calicheamycin, mertansine (DM1), N-acetyl-$\gamma_1^I$-calicheamycin, calicheamycin-$\gamma_1^I$, calicheamycin-$\alpha_2^I$, calicheamycin-$\alpha_3^I$, duocarmycin SA, duocarmycin A, CC-1065, CBI-TMI, duocarmycin C2, duocarmycin B2, centanamycin, dolastatin, auristatin E, monomethylauristatin E (MMAE), monomethylauristatin F (MMAF), α-amanitin, β-amanitin, γ-amanitin, ε-amanitin, amanin, amaninamide, amanullin, and amanullinic acid and derivatives thereof.

Exemplary auristatin embodiments include the N-terminus linked monomethylauristatin drug moieties comprising a structure of any of Formulas V and VI below:

Formula V

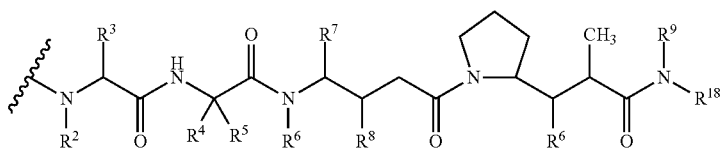

Formula VI

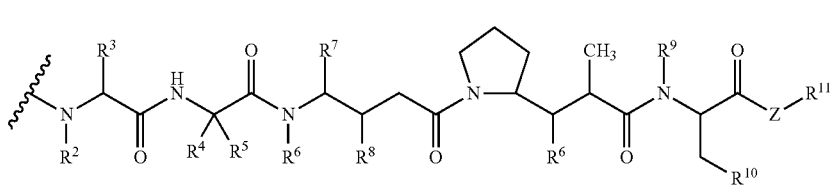

wherein the wavy line of V and VI indicates the covalent attachment site to a L, L', V, V', Y, Y', (RR'), R' or (C)$_n$ group of a linker (e.g. a compound of Formula I, II or IV), and independently at each location:

$R^2$ is selected from H and $C_1$-$C_8$ alkyl;

$R^3$ is selected from H, $C_1$-$C_8$ alkyl, $C_1$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^4$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^5$ is selected from H and methyl;

or $R^4$ and $R^5$ jointly form a carbocyclic ring and have the formula —$(CR^aR^b)_n$— wherein $R^a$ and $R^b$ are independently selected from H, $C_1$-$C_8$ alkyl and $C_3$-$C_8$ carbocycle and n is selected from 2, 3, 4, 5 and 6;

$R^6$ is selected from H and $C_1$-$C_8$ alkyl;

$R^7$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

each $R^8$ is independently selected from H, OH, $C_1$-$C_8$ alkyl, $C_3$-$C_8$ carbocycle and O—($C_1$-$C_8$ alkyl);

$R^9$ is selected from H and $C_1$-$C_8$ alkyl;

$R^{10}$ is selected from aryl or $C_3$-$C_8$ heterocycle;

Z is O, S, NH, or $NR^{12}$ wherein $R^{12}$ is $C_1$-$C_8$ alkyl;

$R^{11}$ is selected from H, $C_1$-$C_{20}$ alkyl, aryl, C3-C8 heterocycle, —$(R^{13}O)_m$—$R^{14}$, or —$(R^{13}O)_m$—$CH(R^{15})_2$; m is an integer ranging from 1-1000;

$R^{13}$ is $C_2$-$C_8$ alkyl;

$R^{14}$ is H or $C_1$-$C_8$ alkyl;

each occurrence of $R^{15}$ is independently H, COOH, —$(CH_2)_n$—$N(R^{16})_2$, —$(OH_2)_n$—$SO_3$—$C_1$-$C_8$ alkyl;

each occurrence of $R^{16}$ is independently H, $C_1$-$C_8$ alkyl, or —$(CH_2)_n$—COOH;

$R^{18}$ is selected from —$C(R^8)_2$—$C(R^8)_2$-aryl, —$C(R^8)_2$—$C(R^8)_2$—($C_3$-$C_8$ heterocycle), and —$C(R^8)_2$—$C(R^8)_2$—($C_3$-$C_8$ carbocycle); and n is an integer ranging from 0 to 6.

In one embodiment, $R^3$, $R^4$ and $R^7$ are independently isopropyl or sec-butyl and $R^5$ is —H or methyl. In an exemplary embodiment $R^3$ and $R^4$ are each isopropyl, $R^5$ is —H, and $R^7$ is sec-butyl.

In yet another embodiment, $R^2$ and $R^6$ are each methyl, and $R^9$ is —H.

In still another embodiment, each occurrence of $R^8$ is —$OCH_3$.

In an exemplary embodiment, $R^3$ and $R^4$ are each isopropyl, $R^2$ and $R^6$ are each methyl, $R^5$ is —H, $R^7$ is sec-butyl, each occurrence of $R^8$ is —$OCH_3$, and $R^9$ is —H.

In one embodiment, Z is —O— or —NH—.

In one embodiment, $R^{10}$ is aryl.

In an exemplary embodiment, $R^{10}$ is -phenyl.

In an exemplary embodiment, when Z is —O—, $R^{11}$ is —H, methyl or t-butyl.

In one embodiment, when Z is —NH, $R^{11}$ is —$CH(R^{15})_2$, wherein $R^{15}$ is —$(CH_2)_n$—$N(R^{16})_2$, and $R^{16}$ is —$C_1$-$C_8$ alkyl or —$(CH_2)_n$—COOH.

In another embodiment, when Z is —NH, $R^{11}$ is —CH$(R^{15})_2$, wherein $R^{15}$ is —$(CH_2)_n$—$SO_3$H.

One exemplary auristatin embodiment of formula V is MMAE, wherein the wavy line indicates the covalent attachment to a L, L', V, V', Y, Y', (RR'), R' or (C)$_n$ group (e.g. of a compound of Formula I, II or IV):

MMAE

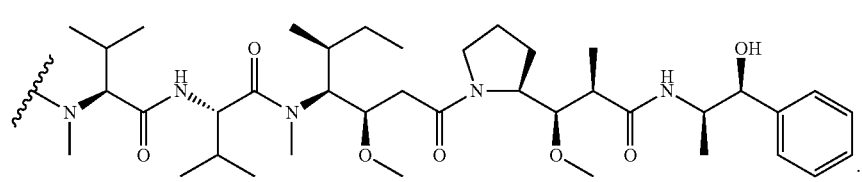

An exemplary auristatin embodiment of formula VI is MMAF, wherein the wavy line indicates the covalent attachment to a linker (L) of an antibody-drug conjugate (see US 2005/0238649 and Doronina et al. (2006) Bioconjugate Cfiem. 17: 1 14-124):

MMAF

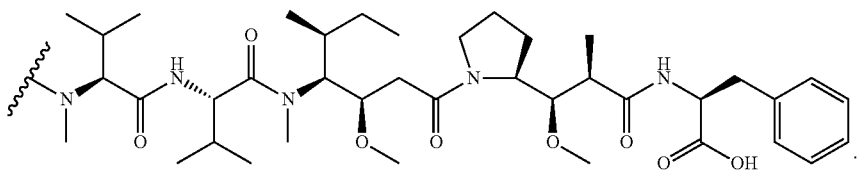

Other exemplary Z embodiments include monomethylvaline compounds having phenylalanine carboxy modifications at the C-terminus of the pentapeptide auristatin drug moiety (WO 2007/008848) and monomethylvaline compounds having phenylalanine sidechain modifications at the C-terminus of the pentapeptide auristatin drug moiety (WO 2007/008603).

Other drug moieties include the following MMAF derivatives, wherein the wavy line indicates the covalent attachment to a L, L', V, V', Y, Y', (RR'), R' or (C)$_n$ group (e.g. of a compound of Formula I, II or IV):

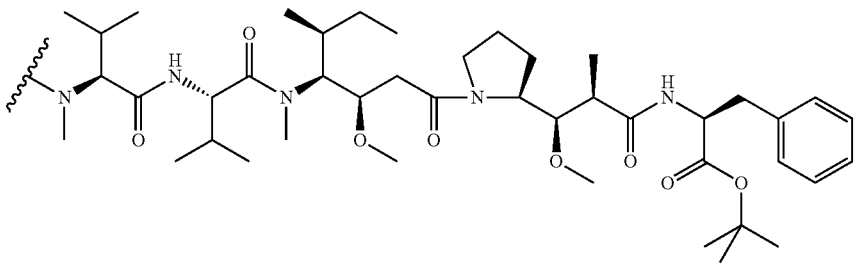

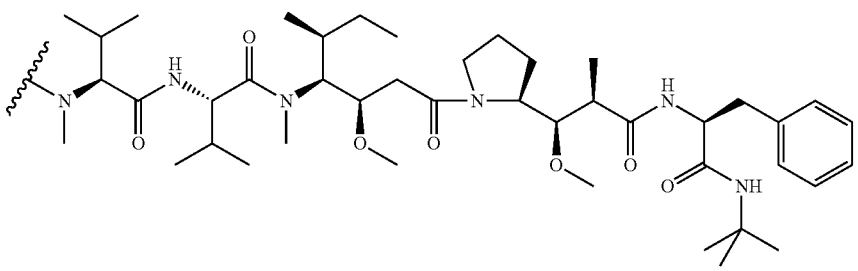

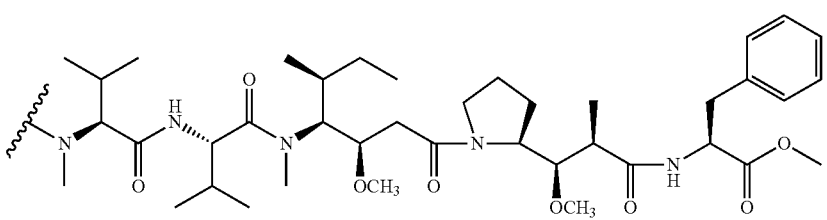

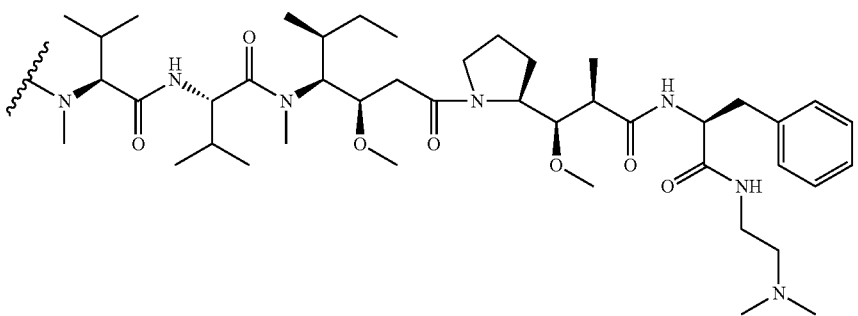

-continued
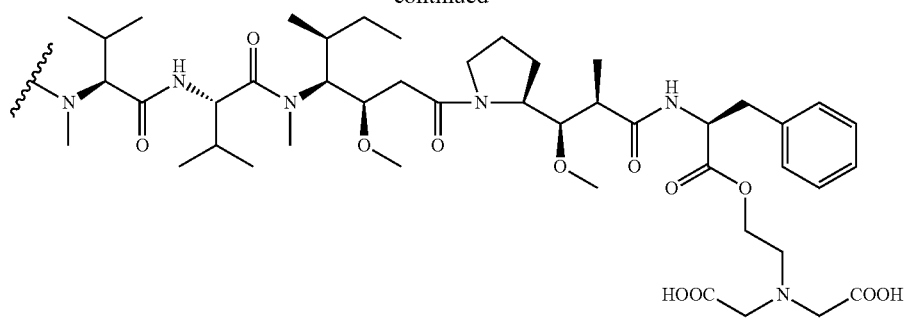
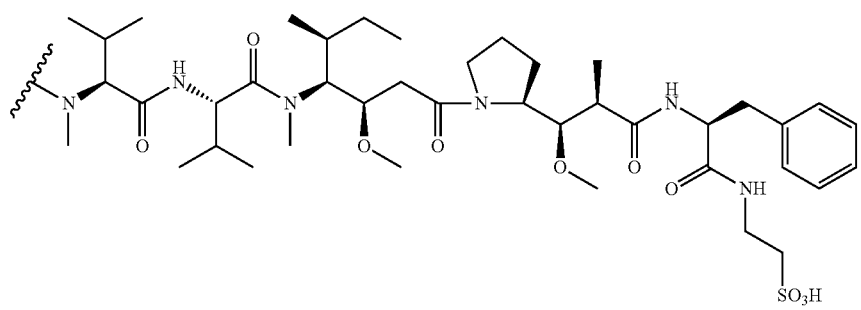
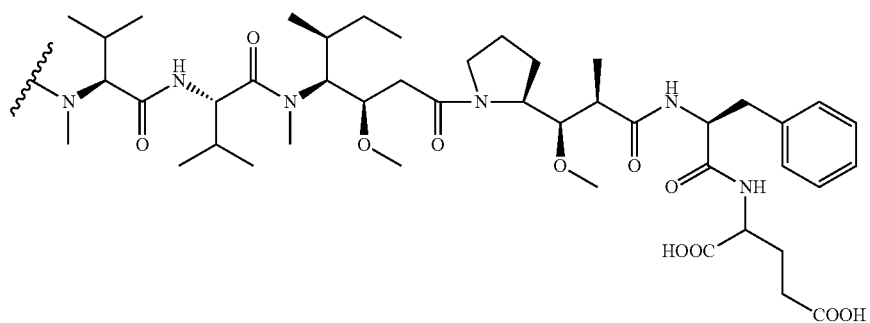
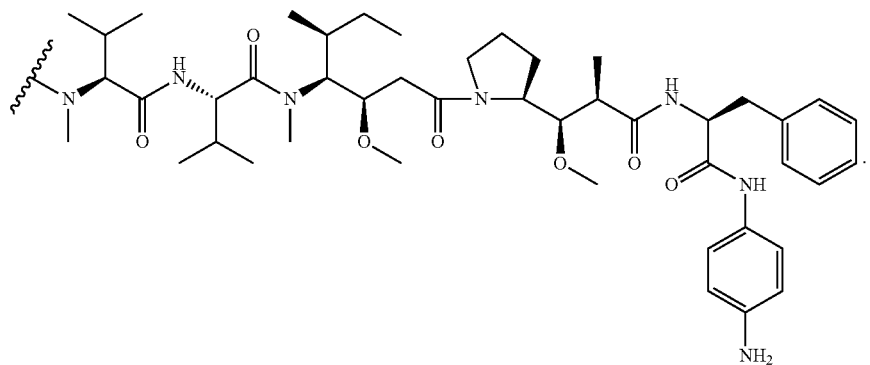

An example of a linker comprising a lysine residue as $(C)_n$ moiety, a valine-citrulline as the (V) moiety, a PAB as the (Y) moiety together with a MMAF as the (Z) moiety is shown below (corresponding to compound Ia-1):

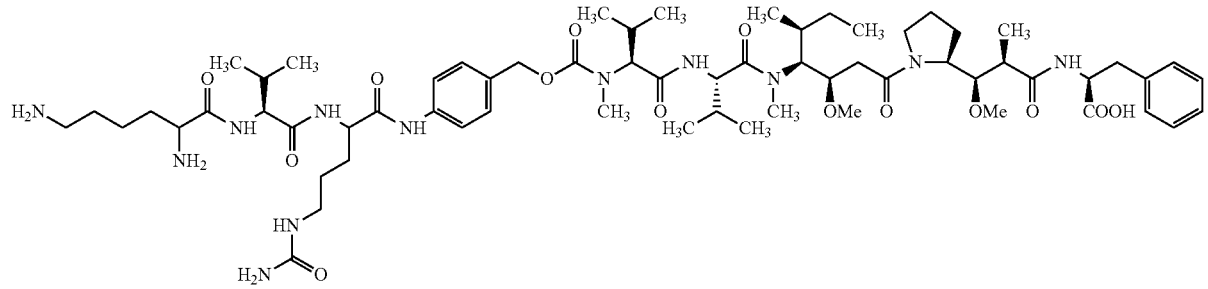 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)C(=O)OCc1ccc(NC(=O)C(CCCNC(N)=O)NC(=O)[C@@H](NC(=O)C(N)CCCCN)C(C)C)cc1)C(C)C]

In one embodiment, the Z moiety is an epothilone or epothilone derivative. An epothilone is a cyclic molecule with a 16-membered ring and variable substituents and pharmaceutical activity as a cytostatic agent that binds to tubulin. Various epothilone derivatives are known, including variants with 14-, 15- or 18-membered rings have also been developed (e.g. WO2011085523; WO2009105969). Examples of epothilones or epothilone analogs or derivatives include epothilone A, epothilone B, epothilone C, 13-alkyl-epothilone C derivatives, epothilone D, trans-epothilone D, epothilone E, epothilone F, an effector conjugate of epothilone, Sagopilone, or any of the epothilones referred to in the literature as ixabepilone (BMS-247550), BMS-310705, EPO-906, Patupilone, Kos-862, Kos-1584, Kos-1803 and ABJ 879, and pharmaceutically active salts thereof. The production of epothilones, their precursors and derivatives is generally carried out according to the methods known to one skilled in the art. Suitable methods are, for example, described in DE 19907588, WO 98/25929, WO 99/58534, WO 99/2514, WO 99/67252, WO 99/67253, WO 99/7692, EP 99/4915, WO 00/485, WO 00/1333, WO 00/66589, WO 00/49019, WO 00/49020, WO 00/49021, WO 00/71521, WO 00/37473, WO 00/57874, WO 01/92255, WO 01/81342, WO 01/73103, WO 01/64650, WO 01/70716, U.S. Pat. No. 6,204,388, U.S. Pat. No. 6,387,927, U.S. Pat. No. 6,380,394, US 02/52028, US 02/58286, US 02/62030, WO 02/32844, WO 02/30356, WO 02/32844, WO 02/14323, and WO 02/8440. Further epothilones are described in WO 93/10102, WO 98/25929, WO 99/02514, WO 99/07692, WO 99/02514, WO 99/67252, WO 00/49021, WO 00/66589, WO 00/71521, WO 01/027308, WO 02/080846, WO 03/074053, and WO 2004/014919.

Other useful therapeutics are set forth in the Physician's Desk Reference and in the Orange Book maintained by the US Food and Drug Administration (FDA). New drugs are continually being discovered and developed, and these new drugs may also be incorporated into a compound.

Chelated metals include chelates of di- or tripositive metals having a coordination number from 2 to 8 inclusive. Particular examples of such metals include technetium (Tc), rhenium (Re), cobalt (Co), copper (Cu), gold (Au), silver (Ag), lead (Pb), bismuth (Bi), indium (In), gallium (Ga), yttrium (Y), terbium (Tb), gadolinium (Gd), and scandium (Sc). In general the metal is preferably a radionuclide. Particular radionuclides include $^{99m}$Tc, $^{186}$Re, $^{188}$Re, $^{58}$Co, $^{60}$Co, $^{67}$Cu, $^{195}$Au, $^{199}$Au, $^{110}$Ag, $^{203}$Pb, $^{206}$Bi, $^{207}$Bi, $^{111}$In, $^{67}$Ga, $^{68}$Ga, $^{88}$Y, $^{90}$Y, $^{160}$Tb, $^{153}$Gd and $^{47}$Sc.

The chelated metal may be for example one of the above types of metal chelated with any suitable polydentate chelating agent, for example acyclic or cyclic polyamines, polyethers, (e.g. crown ethers and derivatives thereof); polyamides; porphyrins; and carbocyclic derivatives.

In general, the type of chelating agent will depend on the metal in use. One particularly useful group of chelating agents in conjugates, however, are acyclic and cyclic polyamines, especially polyaminocarboxylic acids, for example diethylenetriaminepentaacetic acid and derivatives thereof, and macrocyclic amines, e.g. cyclic tri-aza and tetra-aza derivatives (for example as described in PCT publication no. WO 92/22583); and polyamides, especially desferriox-amine and derivatives thereof.

Other effector molecules may include detectable substances useful for example in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerytbrin; suitable luminescent materials include luminol; suitable bioluminescent materials include luciferase, luciferin, and aequorin; and suitable radioactive nuclides include $^{125}$I, $^{131}$I, $^{111}$In and $^{99}$Tc.

Synthetic or naturally occurring polymers for use as effector molecules include, for example optionally substituted straight or branched chain polyalkylene, polyalkenylene, or polyoxyalkylene polymers or branched or unbranched polysaccharides, e.g. a homo- or hetero-polysaccharide such as lactose, amylose, dextran or glycogen.

Particular optional substituents which may be present on the above-mentioned synthetic polymers include one or more hydroxy, methyl or methoxy groups. Particular examples of synthetic polymers include optionally substituted straight or branched chain poly(ethyleneglycol), poly(propyleneglycol), poly(vinylalcohol) or derivatives thereof, especially optionally substituted poly(ethyleneglycol) such as methoxypoly(ethyleneglycol) or derivatives thereof. Such compounds, when used as a moiety Z can be employed as a moiety that improves the pharmacokinetic properties of the antibody.

The size of the polymer may be varied as desired, but will generally be in an average molecular weight range from 500

Da to 50,000 Da, preferably from 5,000 to 40,000 Da and more preferably from 10,000 to 40,000 Da and 20,000 to 40,000 Da. The polymer size may in particular be selected on the basis of the intended use of the product for example ability to localize to certain tissues such as tumors or extend circulating half-life (for review see Chapman, 2002, Advanced Drug Delivery Reviews, 54, 531-545). Thus, for example, where the product is intended to leave the circulation and penetrate tissue, for example for use in the treatment of a tumor, it may be advantageous to use a small molecular weight polymer, for example with a molecular weight of around 5,000 Da. For applications where the product remains in the circulation, it may be advantageous to use a higher molecular weight polymer, for example having a molecular weight in the range from 20,000 Da to 40,000 Da.

Particularly preferred polymers include a polyalkylene polymer, such as a poly(ethyleneglycol) or, especially, a methoxypoly(ethyleneglycol) or a derivative thereof, and especially with a molecular weight in the range from about 10,000 Da to about 40,000 Da.

In another embodiment, z' equals 1, each V, Y or V—Y (including whether any V and Y is a V' or Y') moiety contains a single attachment site for a functional group of Z.

In another embodiment, a V (or V'), Y, (or Y') or V—Y (or V'—Y', V—Y', V'—Y) moiety is attached to more than one Z moiety via multiple functional groups R on the said V, Y or V—Y moiety. Optionally, the one or more V (or V') moieties comprise a polymer, optionally an oligoethylene glycol or a polyethylene glycol or a derivative thereof.

Any one of the Z moieties disclosed herein can be utilized in Formula Ia, IIII, and IVa. Any one of the Z moieties described herein can be used in combination with any of the $(C)_n$, X, L, V, R, Y, Z, M, z, q, and r groups described herein. Any one of the Z moieties described herein can be used in combination with any of the R', L', V', Y', z', q', and r' groups described herein.

The Reactive Moiety R

A linker comprising a reactive moiety (R) can be used so as to create an antibody having a glutamine functionalized with a reactive compound. The antibody conjugate can then subsequently be reacted with a reaction partner to create a desired end-product (e.g., having a moiety-of-interest (Z)).

R can be, for example a moiety comprising an unprotected or protected bioorthogonal-reaction compatible reactive group, for example an unprotected or protected thiol, epoxide, maleimide, haloacetamide, o-phoshenearomatic ester, azide, fulminate, sulfonate ester, alkyne, cyanide, aminothiol, carbonyl, aldehyde, generally any group capable of oxime and hydrazine formation, 1,2,4,5-tetrazine, norbornene, other stained or otherwise electronically activated alkene, a substituted or unsubstituted cycloalkyne, generally any reactive groups which form via bioorthogonal cycloaddition reaction a 1,3- or 1,5-disubstituted triazole, any diene or strained alkene dienophile that can react via inverse electron demand Diels-Alder reaction, a protected or unprotected amine, a carboxylic acid, an aldehyde, or an oxyamine.

When more than one R group is present in a compound of the formula, the R groups will preferably be compatible such that no R group is a complementary reagent to any other R group. The L, V and/or Y groups of formulae I-IV can have r, q, and/or z sites of attachment for the respective V, Y, and R groups, where r and q represent the degree of branching or polymerization. The sites of attachment can comprise a bond or comprise a functional group selected from an alkene, alkyne, ether, thioether, ester, thioester, amine, amide, alkylamide, or other functional group readily generated by a condensation or addition reaction.

The reactive group of the linking reagent can for example chosen to undergo thio-maleimide (or haloacetamide) addition, Staudinger ligation, Huisgen 1,3-cycloaddition (click reaction), or Diels-Alder cycloaddition with a complementary reactive group attached to an agent comprising a therapeutic moiety, a diagnostic moiety, or any other moiety for a desired function.

Optionally, two or more compatible reactive groups can be attached to the linking reagent.

In one embodiment, the reactive group is a haloacetamide, (e.g. bromo-acetamide, iodo-acetamide, cloro-acetamide). Such reactive groups will be more stable in vivo (and in serum) compared with maleimide groups.

In one embodiment, the reactive group is a reagent capable of undergoing a "click" reaction. For example a 1,3-dipole-functional compound can react with an alkyne in a cyclization reaction to form a heterocyclic compound, preferably in the substantial absence of added catalyst (e.g., Cu(I)). A variety compounds having at least one 1,3-dipole group attached thereto (having a three-atom pi-electron system containing 4 electrons delocalized over the three atoms) can be used to react with the alkynes disclosed herein. Exemplary 1,3-dipole groups include, but are not limited to, azides, nitrile oxides, nitrones, azoxy groups, and acyl diazo groups.

Examples include o-phosphenearomatic ester, an azide, a fulminate, an alkyne (including any strained cycloalkyne), a cyanide, an anthracene, a 1,2,4,5-tetrazine, or a norbornene (or other strained cycloalkene).

In one embodiment, R is a moiety having a terminal alkyne or azide; such moieties are described for example in U.S. Pat. No. 7,763,736, the disclosure of which is incorporated herein by reference. Suitable reaction conditions for use of copper (and other metal salt) as catalysts of click-reactions between terminal alkynes and azides are provided in U.S. Pat. No. 7,763,736.

In one embodiment, R is a substituted or unsubstituted cycloalkyne. Cycloalkynes, including heterocyclic compounds, will preferably be used in linking reagents in which an L group is present, preferably wherein L is an alkyl or heteroalkyl chain of 3-30, optionally 5-30 or 5-15 linear carbon atoms, optionally substituted at one or more atoms. Optionally, L is a $(CH_2—CH_2—O)_{1-24}$ group or a $(CH_2)_{x1}—(CH_2—O—CH_2)_{1-24}—(CH_2)_{x2}—$, wherein x1 and x2 are independently an integer selected among the range of 0 to 20. As shown herein, presence of an L group enables high TGase-mediated coupling when cycloalkynes are used.

Cycloalkynes, including specific compounds, are described for example in U.S. Pat. No. 7,807,619, the disclosure of which is incorporated herein by reference.

In some embodiments, a cycloalkyne may be a compound of Formula A:

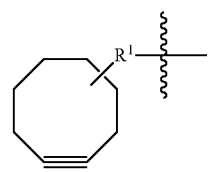

Formula A where:

R[1] is selected from a carbonyl, an alkyl ester, an aryl ester, a substituted aryl ester, an aldehyde, an amide, an aryl amide, an alkyl halide, a thioester, a sulfonyl ester, an alkyl ketone, an aryl ketone, a substituted aryl ketone, and a halosulfonyl;

R[1] can be at any position on the cyclooctyne group other than at the two carbons joined by the triple bond.

In some embodiments, the modified cycloalkyne is of Formula A, wherein one or more of the carbon atoms in the cyclooctyne ring, other than the two carbon atoms joined by a triple bond, is substituted with one or more electron-withdrawing groups, e.g., a halo (bromo, chloro, fluoro, iodo), a nitro group, a cyano group, a sulfone group, or a sulfonic acid group. Thus, e.g., in some embodiments, a subject modified cycloalkyne is of Formula B:

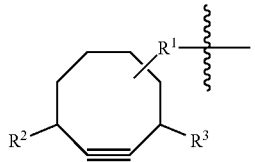

Formula B where:

each of R[2] and R[3] is independently: (a) H; (b) a halogen atom (e.g., bromo, chloro, fluoro, iodo); (c) —W—(CH$_2$)$_n$—Z (where: n is an integer from 1-4 (e.g., n=1, 2, 3, or 4); W, if present, is O, N, or S; and Z is nitro, cyano, sulfonic acid, or a halogen); (d) —(CH$_2$)$_n$—W—(CH$_2$)$_m$—R[4] (where: n and m are each independently 1 or 2; W is O, N, S, or sulfonyl; if W is O, N, or S, then R[4] is nitro, cyano, or halogen; and if W is sulfonyl, then R[4] is H); or (e) —CH$_2$)$_n$—R[4] (where: n is an integer from 1-4 (e.g., n=1, 2, 3, or 4); and R[4] is nitro, cyano, sulfonic acid, or a halogen); and R[1] is selected from a carbonyl, an alkyl ester, an aryl ester, a substituted aryl ester, an aldehyde, an amide, an aryl amide, an alkyl halide, a thioester, a sulfonyl ester, an alkyl ketone, an aryl ketone, a substituted aryl ketone and a halosulfonyl. R[1] can be at any position on the cyclooctyne group other than at the two carbons linked by the triple bond.

In one embodiment, R is a substituted or unsubstituted heterocyclic strained alkyne. Cycloalkynes, including specific compounds, are described for example in U.S. Pat. No. 8,133,515, the disclosure of which is incorporated herein by reference. In one embodiment, the alkyne is of the Formula C:

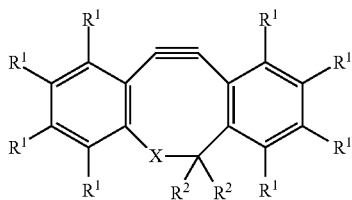

Formula C wherein:

each R[1] is independently selected from the group consisting of hydrogen, halogen, hydroxy, alkoxy, nitrate, nitrite, sulfate, and a C$_1$-C$_{10}$ alkyl or heteroalkyl;

each R[2] is independently selected from the group consisting of hydrogen, halogen, hydroxy, alkoxy, nitrate, nitrite, sulfate, and a C$_1$-C$_{10}$ organic group; X represents N—R[3]R[4], NH—R[4], CH—N—OR[4], C—N—NR[3]R[4], CHOR[4], or CHNHR[4]; and each R[3] represents hydrogen or an organic group and R[4] represents linking moiety C (or (C)$_n$) of a linker. In one embodiment, R or R' is a DBCO (dibenzycyclooctyl) group below:

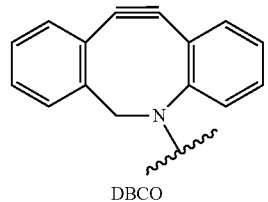

DBCO

Alkynes such as those described herein above can be reacted with at least one 1,3-dipole-functional compound (e.g., embodied as an R' moiety in a compound of Formula III) in a cyclization reaction to form a heterocyclic compound, preferably in the substantial absence of added catalyst (e.g., Cu(I)). A wide variety compounds having at least one 1,3-dipole group attached thereto (having a three-atom pi-electron system containing 4 electrons delocalized over the three atoms) can be used to react with the alkynes disclosed herein. Exemplary 1,3-dipole groups include, but are not limited to, azides, nitrile oxides, nitrones, azoxy groups, and acyl diazo groups.

The reactive moiety R is connected to L, or when present, V or Y, and is able to react with a suitable functional group (R') on a reaction partner, e.g. a complementary reagent of Formula III which undergoes a high conversion addition reaction when brought into contact with a reactive moiety R. When reactive moiety R is present in an antibody of Formula II, the reaction results in formation of an antibody of Formula IV. In this reaction, the moieties R and R' are transformed into the moiety (RR'). Any R' moiety can be defined in the same way as a R moiety, so long as R and R' are complementary when used in moieties that are to be reacted together.

A compound may contain more than one reactive moiety R. The R moieties may or may not be the same. Any one of the R moieties disclosed herein can be utilized in Formula Ib and II. Any one of the R moieties described herein can be used in combination with any of the (C)$_n$, X, L, V, Y, z, q, and r groups described herein. Any one of the R' moieties disclosed herein can be utilized in Formula III. Any one of the R' moieties described herein can be used in combination with any of the L', V', Y', Z, z', q', and r' groups described herein.

The selective and very high conversion addition reactions that can be carried out with the linking reagents can be uncatalyzed or catalyzed reactions. For example, the 2+4 Diels-Alder cycloadditions, thio-maleimide (or haloacetamide) additions, and Staudinger ligations can be carried out without a catalyst. Other very high conversion addition reactions, for example any of the click reactions, can be catalyzed with metal salts, such as Cu, Ru, Ni, Pd, and Pt salts.

The linking group (RR') in M of compounds of Formula IV represents the remainder of R when the reactive moiety R of Formula II has reacted with a reactive moiety R' in a compound of Formula III. This group (RR') then links the moiety Z (e.g. comprised in the compound of formula IV) with L, V or Y. The group that remains may be a bond.

BTG Conjugation Reaction Conditions

Enzymes of the TG-family catalyze covalent protein crosslinking by forming proteinase resistant isopeptide bonds between a lysine donor residue of one protein and an acceptor glutamine residue of another protein, and is accompanied by the release of ammonia. The antibodies that are to be conjugated to the lysine-based linker may or may not be free of N-linked glycosylation (e.g. an antibody which does not comprise glycosylation sites or a modified full-length antibody). For conjugation onto the acceptor glutamines within the CH2 domain, and particularly at residue Q295, antibodies will be free of N-linked glycosylation. Full-length wild-type IgG antibodies naturally comprise N-linked glycosylation at residue 297 of the heavy chain which interferes with TGase-mediated conjugation onto glutamine residues in the CH2 domain. Deglycosylation can be carried out according to any suitable method. For example, antibody in PBS buffer (PBS (10×): Weight 2.1 g $KH_2PO_4$, 90 g NaCl, 4.8 g $Na_2HPO_4 \times 2$ $H_2O$ is transferred to a 1 L glass bottle, to which is added water to a volume of 1 L. To get PBS 1×, use 100 mL PBS (10×) and add water to a volume of 900 mL. pH is adjusted to 7.2 and filled to 1 L with water), and incubated with 6 Units/mg protein of N-glycosidase F (PNGase F) from *Flavobacterium meningosepticum* (Roche, Switzerland) overnight at 37° C. The enzyme is then removed by centrifugation-dialysis (Vivaspin MWCO 50 kDa, Vivascience, Winkel, Switzerland). The product can be analyzed by LC/MS. Alternatively, an antibody will be naturally free of N-linked glycosylation, for example as a result of an amino acid modification, e.g. at residues 297, 298 and/or 299 (EU numbering). For conjugation onto the acceptor glutamines within the CH3 domain (including on a TGase recognition tag fused to a CH3 domain) antibodies need not be free of (may comprise) N-linked glycosylation.

Once antibody and lysine-based linker substrates are prepared they can be reacted by bringing them into contact with one another in a reaction vessel in the presence of a bacterial transglutaminase (BTG) (see, e.g. EC 2.3.2.13, protein-glutamine-γ-glutamyltransferase). The BTG will capable of causing, under suitable conditions, the formation of a covalent bond between the acceptor glutamine residue of the antibody and the linking reagent (at the primary amine of the linking reagent) In one embodiment, the TGase is from *S. mobaraense*. In another embodiment, the TGase is a mutant TGase having 1, 2, 3, 4, 5, 10 or more amino acid modifications (e.g. substitutions, insertions, deletions), optionally the TGase has at least 80% sequence homology with native TGase, e.g. a TGase from *S. mobaraense*. A preferred example is recombinant bacterial transglutaminase derived from *streptomyces mobaraensis* (available from Zedira, Darmstadt, Germany).

Any suitable reaction vessel can be used. A "reaction vessel" is any area or container allowing the interaction of the antibodies, linkers and TGase enzyme described herein. Examples of suitable reaction vessels are sample storage vessels, reaction and collection vessels and plates, multi-well plates, micro titer plate wells or microwells, tubes, microtubes, solid supports (e.g. agarose or Sepharose beads, protein A or protein G-Sepharose), strips and wall less vessels such as array samples comprising hydrophilic and hydrophobic zones.

The TGase will be provided in an amount suitable to provide, in the reaction vessel, TGase activity no more than (or less than) 0.075 enzyme units (U), as determined by a hydroxamate activity assay, per nanomole (nmole) of acceptor glutamine In one embodiment, TGase is present in an amount providing less than 0.2, optionally no more than (or less than) about 0.15 U/nmole of antibody, wherein the antibody has two acceptor glutamines (e.g., one acceptor glutamine on each heavy chain).

In one embodiment, the TGase is present in an amount providing no more than (or less than) about 0.07, optionally less than about 0.06, optionally less than about 0.05, optionally less than about 0.04, or optionally about about 0.0375 or no more than (or less than) about 0.0375 U/nmole of acceptor glutamine.

In one embodiment, TGase is present in an amount providing about 0.075 or no more than (or less than) about 0.075 U/nmole antibody, wherein the antibody has two acceptor glutamines. In one embodiment, TGase is present in an amount providing about 0.15 or no more than (or less than) about 0.15 U/nmole of antibody, wherein the antibody has four acceptor glutamines (e.g., two acceptor glutamines on each heavy chain).

In one embodiment, TGase is present in an amount providing less than about 0.03, 0.02, or 0.01, optionally less than about 0.0075 U/nmole of acceptor glutamine.

In one embodiment, TGase is present in an amount providing less than about 0.06, 0.04, or 0.02, optionally less than about 0.015 U/nmole per nanomole of antibody, wherein the antibody has two acceptor glutamines. In one embodiment, TGase is present in an amount providing less than about 0.075 U/nmole of antibody, wherein the antibody has four acceptor glutamines. In one embodiment, TGase is present in an amount providing less than about 0.12, 0.08, 0.04, or 0.03 U/nmole of antibody, optionally less than about 0.015 U/nmole of antibody, wherein the antibody has four acceptor glutamines.

In one embodiment, TGase is present in an amount providing at least about 0.0004 U/nmole of acceptor glutamine, at least about 0.001 U/nmole of acceptor glutamine, at least about 0.002 U/nmole of acceptor glutamine, at least about 0.005 U/nmole of acceptor glutamine, at least about 0.01 U/nmole of acceptor glutamine, or at least about 0.015 U/nmole of acceptor glutamine. Optionally, in any embodiment herein, TGase is present in an amount providing at least about 0.0004 U/nmole of antibody, at least about 0.0008 U/nmole of antibody, at least about 0.0016 U/nmole of antibody, at least about 0.004 U/nmole of antibody, or at least about 0.01 U/nmole of antibody.

Optionally, in any embodiment herein, TGase is present in an amount providing between about 0.0002 and about 0.075 U/nmole of acceptor glutamine, between about 0.0004 and about 0.075 U/nmole of acceptor glutamine, between about 0.001 and about 0.075 U/nmole of acceptor glutamine, between 0.002 and 0.075 U/nmole of acceptor glutamine, between about 0.005 and about 0.075 U/nmole of acceptor glutamine, or between about 0.01 and about 0.075 U/nmole of acceptor glutamine.

Optionally, in any embodiment herein, TGase is present in an amount providing between about 0.0002 and about 0.04 U/nmole of acceptor glutamine, between about 0.0004 and about 0.04 U/nmole of acceptor glutamine, between about 0.001 and about 0.04 U/nmole of acceptor glutamine, between about 0.002 and about 0.04 U/nmole of acceptor glutamine, between about 0.005 and about 0.04 U/nmole of acceptor glutamine, or between about 0.01 and about 0.04 U/nmole of acceptor glutamine.

Optionally, in any embodiment herein, TGase is present in an amount providing between about 0.0002 and about 0.02 U/nmole of acceptor glutamine, between about 0.0004 and about 0.025 U/nmole of acceptor glutamine, between about 0.001 and about 0.02 U/nmole of acceptor glutamine, between about 0.002 and about 0.02 U/nmole of acceptor glutamine, between about 0.005 and about 0.02 U/nmole of acceptor glutamine, or between about 0.01 and about 0.02 U/nmole of acceptor glutamine.

Optionally, in any embodiment herein, TGase is present in an amount providing between about 0.01 and about 0.06 U/nmole of acceptor glutamine, between 0.01 and 0.05 U/nmole of acceptor glutamine, between about 0.01 and about 0.04 U/nmole of acceptor glutamine, or between about 0.01 and about 0.03 U/nmole of acceptor glutamine.

Optionally, the expression "mole of acceptor glutamine" can be replaced by the expression "mole of antibody", and the amount of TGase enzyme units specified is multiplied by the number of acceptor glutamines available on the antibody.

Such low levels of TGase activity (as a function of the amount of antibody substrate) will avoid deamidation at acceptor glutamines, particularly constant-region bound glutamines such as those in the CH2 domain. The antibody reaction intermediate composition (e.g. prior to conjugation of the lysine-based linker substrate) will therefore be substantially free of deamidated acceptor glutamines (that are consequently no longer available for TGase-mediated conjugation. Optionally, no more than 10%, optionally no more than 5%, optionally no more than 2%, optionally no more than 1%, of the antibodies comprise a deamidated acceptor acceptor glutamine residue. Optionally, the antibody reaction intermediate composition will be characterized by having at least 90%, 95%, 98% or 99% of acceptor glutamines in non-deamidated state (e.g. when TGase in present in the reaction medium).

It will be appreciated that the amount of TGase enzyme to be used in conjugation reactions will depend on the specific activity of the particular TGase used. TGase activity may vary among different manufacturers, lots and enzyme variants, and commercially available TGase will typically be accompanied by specifications of activity. Activity can be expressed as Units (U) of activity, as determined using standard hydroxamate activity assay.

A standard activity assay used in the art is described in Folk and Cole, (1966) Biochim. Biophys. Acta 122:244-264, the disclosure of which is incorporated herein by reference. Kits for carrying out the hydroxamate activity assay are available from suppliers, for example the Microbial Transglutaminase Assay Kit, ref. Z009, from Zedira GmbH, Darmstadt, Germany. Briefly, Microbial Transglutaminase Assay Kit uses Z-Gln-Gly (also available from Sigma Aldrich Corp., N-Benzyloxycarbonyl-L-Glutaminylglycine, CAS Number 6610-42-0) as the amine acceptor substrate and hydroxylamine as amine donor. In the presence of MTG hydoxylamine is incorporated to form Z-glutamylhxdroxamate-glycine which develops a colored complex with iron (III) detectable at 525 nm.

Reagents are prepared by dissolving one vial of Activity Reagent 1 (lyophilized TRIS buffer pH 6.0 containing Z-Gln-Gly, hydroxylamine and reduced glutathione) in 5 ml of deionised water, and dissolving one vial of Activity Reagent 2 (Hydroxylamine) in 1 ml of deionised water. Dissolved Activity Reagent 2 is added to the vial of Activity Reagent 1 and mixed thoroughly. 6 ml of Stop Reagent (Hydrochloric acid, 4% v/v) is transferred into one vial of Stop Reagent 2 (Iron (III) chloride) and mixed thoroughly.

Each sample 500 µL of Activity Reagent is pre-warmed for 10 minutes in suitable reaction tubes (1.5 mL) to 37° C. before testing. The reaction is started by adding 50 µl of sample into 500 µl of Activity Reagent and stopped after exactly 10 minutes by adding 500 µL of Stop Reagent 2. A centrifuge is used to separate precipitations for 5 minutes, 10,000×g at ambient temperature. The reaction mixture (1 mL) can be transferred to a suitable cuvette and measured at 525 nm. Water or buffer is used to generate a blank. A microbial transglutaminase sample can be used as positive control, dissolved in 200 µL of deionised water, for purposes of validating the efficacy and quality of the kit device. 50 µL of microbial transglutaminase (positive control) can be used to maintain a volumetric activity of >0.8 U/mL (ΔE525 nm>0.33). For reliable results ΔE525 nm of the samples should be in the range from 0.1 to 0.9.

One unit (U) of microbial transglutaminase activity is the amount of enzyme, which causes the formation of 1.0 µmole of hydroxamate per minute by catalysing the reaction between Z-Gln-Gly and hydroxylamine at pH 6.0 at 37° C. (Folk and Cole, 1966).

The results can be evaluated using following equation.

$$\text{Activity}\left[\frac{U}{mL}\right] = \left[\frac{\Delta E \times V}{\epsilon \times d \times v \times t}\right] = \Delta E \times 2.64 \left[\frac{\mu mol}{min \times mL}\right]$$

With: ΔE=extinction (525 nm), V=total volume (1.050 mL), d=cuvette (1 cm), t=time 10 min), v=sample volume (50 µL), e=0.795 mL×µmol−1×cm−1 (note: molar extinction coefficient of hydroxyl glutamate in the stopped assay solution differs from the value obtained using the protocol of Folk and Cole (1966).

The TGase-catalyzed reaction can be carried out under mild conditions, generally over several hours. Exemplary conditions at antibody concentrations that provide excellent coupling results (about 5 mg/mL) include use of recombinant bacterial transglutaminase from *streptomyces mobaraensis* (Zedira, Darmstadt, Germany) at a concentration of between 0.5 U/mL and 2 U/mL. However, if higher or lower antibody concentrations are used (e.g. between 0.1 ml/mL and 10 mg/mL) it will be appreciated that Tgase can be varied, e.g. at a concentration of between 0.1 and 10 U/ml. The TGase can for example be provided in an amount suitable to provide, in the reaction vessel, TGase activity which is about 0.03, 0.04, 0.05, or 0.06 U TGase per nmole of antibody.

The lysine-based linker substrates can be reacted with antibody at ligand concentrations providing for example about a 10 or 20-fold excess over the number of acceptor glutamines available on the antibody. However lower excess of lysine-based linker substrates per acceptor glutamine available on the antibody, e.g. 1- or 2- to 10-fold, or 2-5 fold excess substrates can also be used. With lower excesses of lysine-based linker and a full-length antibody having an acceptor glutamine in the CH2 domain (e.g. Q295 and/or N297Q), lower amounts of TGase activity can provide improved coupling (compared to amounts used with higher excesses of substrate).

Use of higher excess of lysine-based linker substrates (e.g. more than 10-fold excess per acceptor glutamines) will favor the TGase-mediated conjugation reaction, permitting a lower ratio of antibody to TGase activity to be used whilst still avoiding deamidation. Thus with higher excesses of lysine-based linker and a full-length antibody having an acceptor glutamine in the CH2 domain (e.g. Q295 and/or N297Q), the TGase can for example be provided in somewhat higher amounts (within the parameters and ranges provided here) than when lower excesses of linker substrate are used.

The reactions can be performed in potassium-free phosphate buffered saline (PBS; pH 7.4) at 37° C. After several hours (depending on the antibody and the ligand), substantially full conjugation is achieved. Reactions can be monitored by LC/MS.

Reaction Partners Comprising a Moiety-of-Interest Z and Reactive Group R'

In one optional embodiment a multi-step process is used starting from a lysine-based linker (e.g., compound of Formula Ib) comprising a reactive moiety R is conjugated to an antibody by TGase. The result is a composition of antibodies or antibody fragments comprising a functionalized acceptor glutamine residue having Formula II:

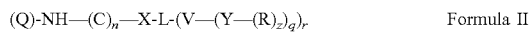  Formula II

No more than 10%, optionally no more than 5%, optionally no more than 2%, optionally no more than 1%, of the antibodies in the composition will comprise a deamidated acceptor acceptor glutamine residue. The antibody composition can then be reacted with a compound comprising a moiety Z and a reactive group R', thereby forming an antibody-moiety-of-interest conjugate.

Optionally, the conjugated antibody (e.g. the antibody of Formula II) is subjected to a deprotection step to provide an unprotected reactive group (R) and the antibody is then reacted with a compound comprising a reaction partner R'.

R' is a reactive moiety, for example a moiety comprising an unprotected or protected bioorthogonal-reaction compatible reactive group, for example an unprotected or protected thiol, epoxide, maleimide, haloacetamide, o-phoshenearomatic ester, azide, fulminate, sulfonate ester, alkyne, cyanide, amino-thiol, carbonyl, aldehyde, generally any group capable of oxime and hydrazine formation, 1,2,4,5-tetrazine, norbornene, other stained or otherwise electronically activated alkene, a substituted or unsubstituted cycloalkyne, generally any reactive groups which form via bioorthogonal cycloaddition reaction a 1,3- or 1,5-disubstituted triazole, any diene or strained alkene dienophile that can react via inverse electron demand Diels-Alder reaction, a protected or unprotected amine, a carboxylic acid, an aldehyde, an oxyamine, so long as such group when unprotected is reactive with R (when R' is unprotected).

Alkynes such as those described herein can be reacted with at least one 1,3-dipole-functional compound (e.g., embodied in reactive group R of Formula Ia or Ib in a cyclization reaction to form a heterocyclic compound, preferably in the substantial absence of added catalyst (e.g., Cu(I)).

Examples or R' include the compounds of Formulae A, B and C disclosed herein in the context of reactive group (R). In one embodiment, when R' is a cycloalkyne, including a heterocyclic compound, the linking reagent of Formula Ia or Ib may comprise a non-cyclic R group, optionally furthermore wherein L is a bond or a shorter carbon framework as L group. For example, R may be a non-cyclic group and L may comprise a carbon framework of 1-5 linear carbon atoms, optionally substituted at one or more atoms.

Any one of the R' moieties disclosed herein can be utilized in Formula III. Any one of the R' moieties described herein can be used in combination with any of the L', V', Y', Z, z', q', and r' groups described herein.

The compounds (e.g. Formula III) to be used in reaction with an antibody can be reacted with antibody (e.g., 1 mg/mL) at ligand concentrations between 2 and 20 (or between 4 and 20) molar equivalents to the antibody, optionally between 2 and 10 (or between 4 and 10) molar equivalents to the antibody, optionally at less than, or about, 20, 10, 5, 4 or 2 molar equivalents to the antibody. However it will be appreciated that higher excesses (equivalents of reaction partner (e.g. Formula III) to antibody (40 to 80 fold, 60 to 90-fold) can also be used).

The compounds of Formula III to be used in reaction with an antibody conjugated to a lysine-based linker (but without a moiety-of-interest), e.g., an antibody of Formula II, as well as the resulting antibody conjugates therefore comprise one or more moieties-of-interest Z. The compounds of Formula III may additionally comprise a moiety V and/or Y, typically depending on which elements are included in the lysine-based linker.

The compounds of Formula III to be used in reaction with an antibody conjugated to a lysine-based linker (e.g. an antibody of Formula II) will comprise moieties Z connected to linker L' when Y' and V' are absent, connected to the spacer system Y' or, when Y' is absent, connected to V'. Consequently, a compound of Formula III may comprise a moiety Z connected to or comprising a reactive group R', optionally the moiety Z connected to a reactive group R' via a spacer system Y' or, when Y' is absent, to a reactive group R' via V', or to a reactive group R' via a V'—Y', wherein Z is preferably connected to Y' and V' is connected to R' and Y'.

A compound of Formula III may contain one, two or more Z moieties that are the same or that differ from one another, e.g. different therapeutic moieties, and/or diagnostic moieties.

In one embodiment, the antibody of Formula II is reacted with a compound of Formula III comprising a moiety of interest Z comprising and a reactive group R' capable of forming a bond with reactive group R of Formula Ib or II, optionally wherein the compound further comprises a V' and/or Y' group. The compound comprising a moiety of interest Z comprising and a reactive group R' preferably comprises a structure of Formula III, below,

  Formula III where:

R' is a reactive group, e.g. a reactive group complementary for forming at least one bond with reactive group R of Formula Ib, Ic or II; and L', V', Y', q', r' and z' can be defined the same way as L, V, Y, q, r and z (independently of L, V, Y, q, r and z).

Examples of compounds of Formula III include but are not limited to compound having the R', L', V', Y' and Z groups shows in Table 4 herein. The symbol (-) in the tables indicates that the particular R', L', V', Y' or Z is absent. V and Y groups, for example, can comprise any structural features in the sections titled "The V Moiety" and "The Y Moiety" herein. The L, V and/or Y groups of Formula III represented in Table 4 can have r', q', and/or z' sites of attachment for the respective V, Y, and R or Z groups, where r and q represent the degree of branching or polymerization; r', q', and/or z' can be selected from 1, 2, 3 or 4.

Non-limiting examples of compounds of Formula Ia and reaction partners of Formula III are shown in Table 5.

Antibody Conjugate Compositions

As discussed, linking reagent can be directly conjugated to an antibody or antibody fragment, either directly or in a multi-step process with a further step of reacting involving reactive groups R and R'. The composition of antibodies or antibody fragments resulting from methods disclosed herein will have low or no deamidation of acceptor glutamines, and following incubation with linker substrates will have high percentages of acceptor glutamines functionalized with lysine-based linkers.

The resulting composition can be characterized as comprising a plurality of antibodies (e.g. having the same amino acid sequences) comprising a functionalized acceptor glutamine residue linked (covalently) to a linking reagent (e.g. a functionalized glutamine residue of Formula IVa or IVb, below) wherein no more than 10%, optionally no more than 5%, optionally no more than 2%, optionally no more than 1%, of the antibodies comprise a deamidated acceptor acceptor glutamine residue. The composition can also be characterised by at least 90%, 95%, 98% or 99% of the antibodies in said composition obtained having (m) functionalized acceptor glutamine residues (Q) per antibody, wherein m is an integer selected from 1, 2 (e.g. for antibodies having one acceptor glutamine in each heavy chain constant region) or 4 (e.g. for antibodies having two acceptor glutamines in each heavy chain constant region).

In one aspect, an antibody or antibody fragment in the compositions provided herein comprises a functionalized glutamine residue of Formula IVa, below,

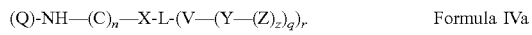
    (Q)-NH—(C)$_n$—X-L-(V—(Y—(Z)$_z$)$_q$)$_r$    Formula IVa or a pharmaceutically acceptable salt thereof;
wherein:

Q is a glutamine residue present in an antibody or antibody fragment;

(C)$_n$ is a substituted or unsubstituted alkyl or heteroalkyl chain, wherein any carbon of the chain is optionally substituted with an alkoxy, hydroxyl, alkylcarbonyloxy, alkyl-S—, thiol, alkyl-C(O)S—, amine, alkylamine, amide, or alkylamide (e.g. a O, N or S atom of an ether, ester, thioether, thioester, amine, alkylamine, amide, or alkylamide);

n is an integer selected from among the range of 2 to 20;

X is NH, O, S, or absent;

L is a bond or a carbon comprising framework, preferably of 1 to 200 atoms substituted at one or more atoms, optionally wherein the carbon comprising framework is a linear hydrocarbon, a symmetrically or asymmetrically branched hydrocarbon monosaccharide, disaccharide, linear or branched oligosaccharide (asymmetrically branched or symmetrically branched), other natural linear or branched oligomers (asymmetrically branched or symmetrically branched), or a dimer, trimer, or higher oligomer (linear, asymmetrically branched or symmetrically branched) resulting from any chain-growth or step-growth polymerization process;

r is an integer selected among 1, 2, 3 or 4;
q is an integer selected among 1, 2, 3 or 4;
z is an integer selected among 1, 2, 3 or 4; and V is independently absent, a non-cleavable moiety or a conditionally-cleavable moiety that can optionally be cleaved or transformed by a chemical, photochemical, physical, biological, or enzymatic process (e.g. cleavage of V ultimately leading to release of one or more moieties subsequently or ultimately linked to V, for example a Z moiety). In some embodiments, V is, preferably, a di-, tri-, tetra-, or oligopeptide as described below in the section entitled "The V Moiety";

Y is independently absent or a spacer (e.g., a self-eliminating spacer system or a non-self-elimination spacer system) which is comprised of 1 or more spacers; and Z is a moiety-of-interest, optionally a moiety that improves the pharmacokinetic properties, or a therapeutic moiety or a diagnostic moiety. Preferably, Z is a cytotoxic anti-cancer agent, e.g. a compound selected from the group consisting of taxanes, anthracyclines, camptothecins, epothilones, mytomycins, combretastatins, vinca alkaloids, nitrogen mustards, maytansinoids, calicheamycins, duocarmycins, tubulysins, amatoxins, dolastatins and auristatins, enediynes, radioisotopes, therapeutic proteins and peptides, and toxins or fragments thereof.

Generally, each Z is directly coupled to either Y or V when Y is absent, or L when both Y and V are absent. Optionally, a compound of Formula IVa can be characterized as not comprising an RR' group, or not comprising a particular RR' group described herein. It will be appreciated that Formula IVa can for convenience also be expressed as (Ab)-NH—(C)$_n$—X-L-(V—(Y—(Z)$_z$)$_q$)$_r$ (Formula IVa), where (Ab) is an immunoglobulin (Ab) is conjugated via a glutamine (Q) residue to an NH of the linking reagent (e.g the compound of Formula Ia).

Examples of antibodies or antibody fragments of Formula IVa include but are not limited to antibodies and fragments attached via an amide bond (e.g. through an acceptor glutamine residue in the primary sequence of the antibody or antibody fragment) to a compound selected from the group consisting of compounds Ia-1 to Ia-23 (wherein the terminal NH$_2$— of each of said compound Ia-1 to Ia-23 is replaced by a moiety ((Q)-NH—) when attached to the antibody or fragment, wherein Q is a glutamine residue present in an antibody or antibody fragment.

The antibody conjugates resulting from the reaction of the compounds of Formula Ib or III with an antibody conjugated to a lysine-based linker will yield an antibody conjugate in which a moiety Z is connected to linker L (or L') when Y (or Y') and V (or V') are absent, to the spacer system Y (or Y') or, when Y (or Y') is absent, to V (or V').

In one embodiment, a multi-step process is used and a reactive group or product of a reaction (RR') remain present in a conjugated antibody or antibody fragment. Such an antibody or antibody fragment in the compositions provided herein comprises a functionalized glutamine residue of Formula IVb, below,

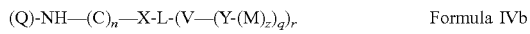
    (Q)-NH—(C)$_n$—X-L-(V—(Y-(M)$_z$)$_q$)$_r$    Formula IVb or a pharmaceutically acceptable salt or solvate thereof;
wherein:

Q is a glutamine residue present in an antibody or antibody fragment;

(C)$_n$ is a substituted or unsubstituted alkyl or heteroalkyl chain, wherein any carbon of the chain is optionally substituted with an alkoxy, hydroxyl, alkylcarbonyloxy, alkyl-S—, thiol, alkyl-C(O)S—, amine, alkylamine, amide, or alkylamide;

n is an integer selected from among the range of 2 to 20;

X is NH, O, S, or absent;

L is a bond or a carbon comprising framework, preferably of 1 to 200 atoms substituted at one or more atoms, optionally wherein the carbon comprising framework is a linear hydrocarbon, a symmetrically or asymmetrically branched hydrocarbon monosaccharide, disaccharide, linear or branched oligosaccharide (asymmetrically branched or symmetrically branched), other natural linear or branched oligomers (asymmetrically branched or symmetrically branched), or a dimer, trimer, or higher oligomer (linear, asymmetrically branched or symmetrically branched) resulting from any chain-growth or step-growth polymerization process;

r is an integer selected among 1, 2, 3 or 4;
q is an integer selected among 1, 2, 3 or 4;
z is an integer selected among 1, 2, 3 or 4; and V is independently absent, a non-cleavable moiety or a conditionally-cleavable moiety that can optionally be cleaved or transformed by a chemical, photochemical, physical, biological, or enzymatic process (e.g. cleavage of V ultimately leading to release of one or more moieties subsequently or ultimately linked to V, for example a Z moiety). In some embodiments, V is, preferably, a di-, tri-, tetra-, or oligopeptide as described below in the section entitled "The V Moiety";

Y is independently absent or a spacer (e.g., a self-eliminating spacer system or a non-self-elimination spacer system) which is comprised of 1 or more spacers; and M is independently: R or (RR')-L'-(V'—(Y'—(Z)$_{z'}$)$_{q'}$)$_{r'}$, wherein each of L', V', Y', z', q', and r' are as defined in Formula III (or are defined as L, V, Y, z, q and r, respectively), Z is a moiety-of-interest, optionally a moiety that improves the pharmacokinetic properties, or a therapeutic moiety or a diagnostic moiety, R is as defined in Formula I and wherein each (RR') is an addition product between an R of Formula I and its complementary R' of Formula III.

Thus, RR' can be for example an addition product of a thio-maleimide (or haloacetamide) addition, for example, a N,S-disubstituted-3-thio-pyrrolidine-2,5-dione; Staudinger ligation, for example, a N,3- or N,4-substituted-5-dipenyl-phosphinoxide-benzoic amide; Huisgen 1,3-cycloaddition (click reaction), for example, a N,S-disubstituted-3-thio-pyrrolidine-2,5-dione, 1,4-disubstituted-1,2,3-triazole, 3,5-disubstituted-isooxazole, or 3,5-disubstituted-tetrazole; Diels-Alder cycloaddition adduct, for example the 2,4-cycloaddition product between an O or N-substituted-5-norbornene-2-carboxylic ester or amide, N-substituted-5-norbornene-2,3-dicarboxylic imide, O or N-substituted-7-oxonorbornene-5-carboxylic ester or amide, or N-substituted-7-oxonorbornene-5,6-dicarboxylic imide and a 9-substituted anthracene or 3-substituted 1,2,4,5-tetrazine; or any high yield selective amidation or imidization reaction.

Examples of RR' include:

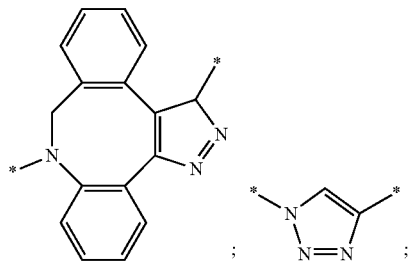

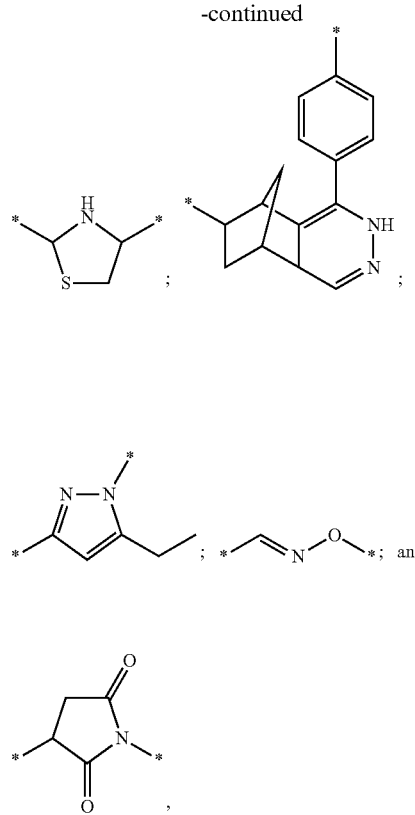

wherein (*) indicates the site of attachment of —(C)$_n$, X, L, L', V, V', Y, Y' or Z. RR' can be in either orientation with respect to their attachment to —(C)$_n$, X, L, L', V, V', Y, Y' or Z.

Optionally, the antibody conjugate comprises a group (RR') representing the remainder of a reactive moiety R when R has reacted with a reactive moiety R', wherein the group (RR') connects (a) an L to a Z, a V or a Y, (b) a V to a Z or a Y, or (c) a Y to a Z. For example, any V, Y and/or Z may be characterized as comprising a (RR') group. Any L, V, Y may be an L', V' or Y', respectively.

Examples of antibodies or antibody fragments of Formula IVb include but are not limited to:

Compound IVb-1

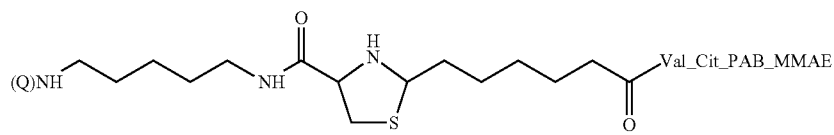

Compound IVb-2

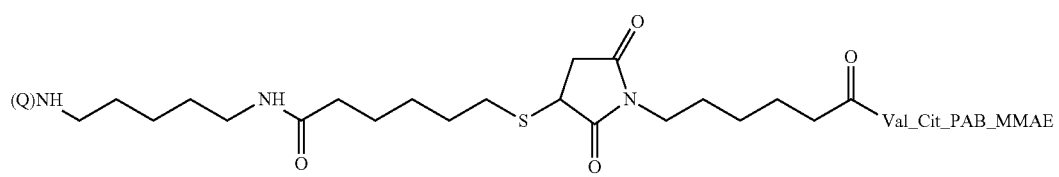

Compound IVb-3
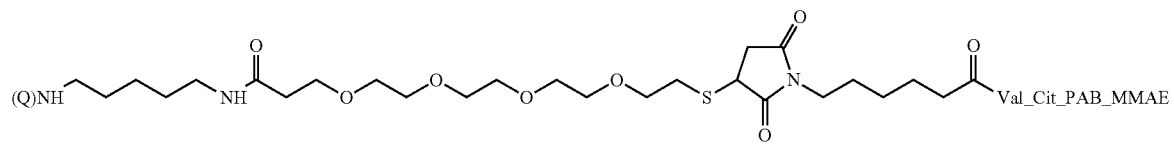
Compound IVb-4
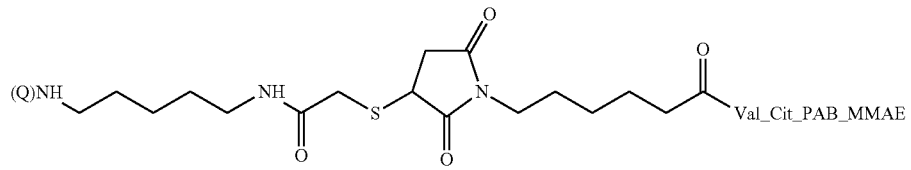
Compound IVb-5
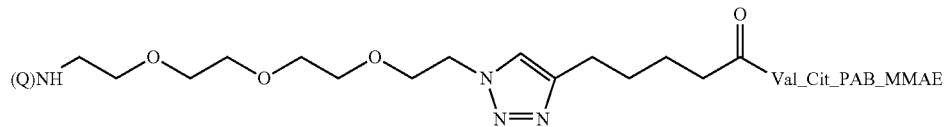
Compound IVb-6
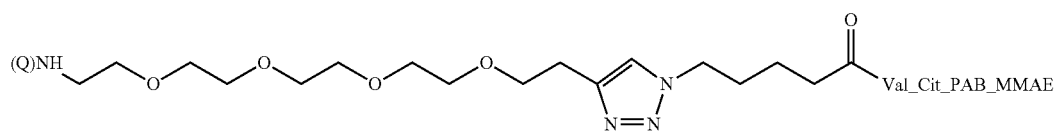
Compound IVb-7
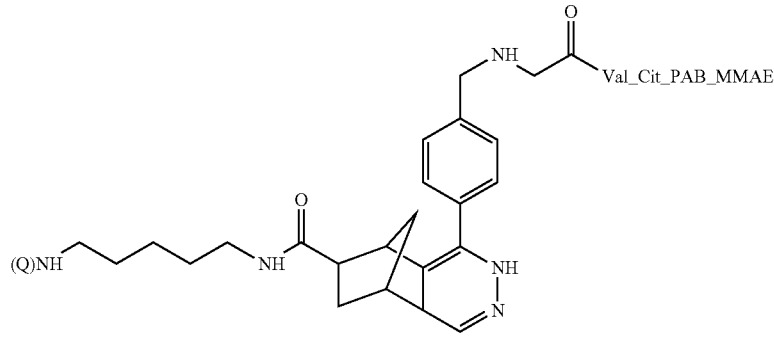
Compound IVb-8
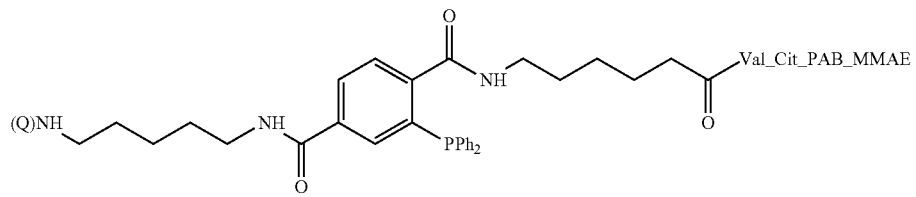
Compound IVb-8
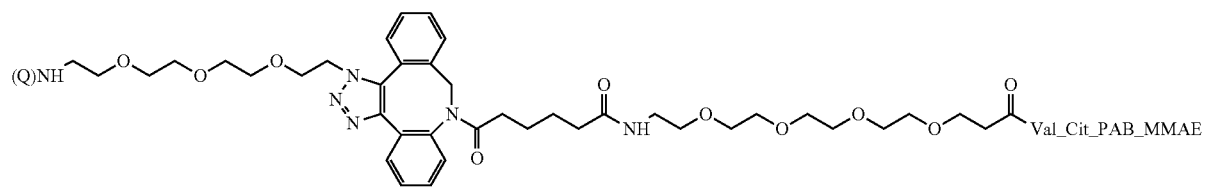
Compound IVb-9
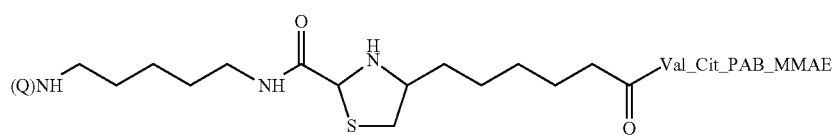

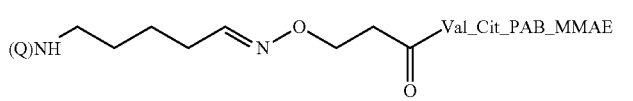

Compound IVb-9

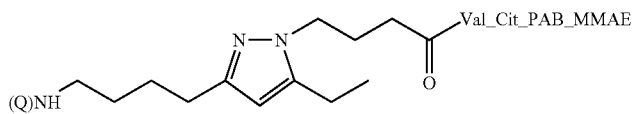

Compound IVb-9

Uses of Compositions

In one aspect, the disclosure relates to the use of any of the compositions (e.g. antibody compositions, reaction vessels or containers) provided herein for the manufacture of a diagnostic product, a kit and/or a pharmaceutical preparation for the treatment or diagnosis of a mammal in need thereof. In one embodiment, the disclosure relates to the use of any of the compositions (e.g. antibody compositions, reaction vessels or containers) for the manufacture of a pharmaceutical composition for the treatment of a tumor or infectious disease in a mammal.

Also the disclosure relates to any of the antibody compositions as a medicament or an active component or active substance in a medicament. In a further aspect the disclosure relates to a method for preparing a pharmaceutical composition containing a composition to provide a solid or a liquid formulation for administration orally, topically, or by injection. Such a method or process at least comprises the step of mixing the compound with a pharmaceutically acceptable carrier.

In one aspect, the disclosure relates to a method to affect or prevent a predefined condition by exerting a certain effect, or detect a certain condition using a composition disclosed herein, or a (pharmaceutical) composition comprising a composition disclosed herein.

In one embodiment, the disclosure relates to a method of detecting the presence of a certain condition, e.g., the presence of an enzyme, the presence of a certain pH, the presence of a (bio)molecule, the presence of a substrate, or the presence of a certain oxygen concentration, with a composition disclosed herein, either in vivo or ex vivo.

In one embodiment, the disclosure relates to a method of determining an enzyme ex vivo, e.g., in a diagnostic assay, using a composition disclosed herein by incubating a sample (possibly) containing said enzyme with a composition of this invention containing one or more diagnostic moieties Z and a substrate for said (proteolytic) enzyme, and observing release of said Z moieties. The phrase "determining an enzyme" means both qualitative analysis, i.e., detecting the presence of the enzyme, determining whether it is present, and quantitative analysis, i.e., quantifying the enzyme, determining the enzyme activity present in the sample. An enzyme can also be indirectly determined via its pro-enzyme containing a recognition site, e.g., an activation site, cleavable by said enzyme to be determined. Cleavage of the pro-enzyme can in such case be detected by observing the resulting activity using a suitable compound disclosed herein.

In one embodiment the disclosure relates to a diagnostic assay method (in vivo or ex vivo) in which a composition according to the disclosure is used.

In a further embodiment the disclosure relates to a method in which the presence or amount of an enzyme is determined by using a composition according to the disclosure.

In one embodiment, the disclosure relates to a method to affect or prevent a predefined condition, e.g., a disease such as an autoimmune disease, a microbial disease, or cancer, by exerting an effect using a composition disclosed herein.

In a further embodiment, the disclosure relates to a method of treating a mammal being in need thereof, whereby the method comprises the administration of a pharmaceutical composition to the mammal in a therapeutically effective dose.

In a further embodiment, the disclosure relates to a method of treating a mammal having an illness characterized by undesired (cell) proliferation with a composition disclosed herein. In another embodiment disclosed is a method of treating a mammal carrying a tumor with a composition disclosed herein. In yet another embodiment disclosed is a method of treating a mammal having an inflammatory disease with a composition disclosed herein. In yet another embodiment disclosed is a method of treating a mammal having an autoimmune disease with a composition disclosed herein. In yet another embodiment disclosed is a method of treating a mammal having a bacterial or microbial infection with a composition disclosed herein.

In one embodiment, the disclosure relates to a method of treating cancer in a mammal, whereby the method comprises the administration of a pharmaceutical composition to the mammal in a therapeutically effective dose.

In one embodiment, a composition of the disclosure is used to treat an illness characterized by undesired proliferation. In another embodiment, a composition provided herein is used to treat an illness characterized by undesired (cell) proliferation. In another embodiment, a compound of the disclosure is used to treat a tumor. In yet another embodiment, a composition provided herein is used to treat an inflammatory disease. In yet another embodiment a composition provided herein is used to treat an autoimmune disease. In yet another embodiment a composition provided herein is used to treat a bacterial or microbial infection.

In one embodiment, the composition provided herein is capable of being internalized into cells that express an antigen to which the antibody binds (e.g. a tumor or viral antigen) and/or induces internalization of the antigen on said antigen-expressing cells. In one embodiment, the compound provided herein is toxic to a cell upon internalization (i.e. the compound comprises a moiety Z that is toxic to a cell). Preferably such compositions can be used in methods of killing or eliminating cells, preferably wherein said cells are tumor cells.

The disclosure also relates to pharmaceutical compositions comprising the composition provided herein as defined above. A composition provided herein may be administered in purified form together with a pharmaceutical carrier or excipient as a pharmaceutical composition. The preferred form depends on the intended mode of administration and therapeutic or diagnostic application. The pharmaceutical carrier can be any compatible, nontoxic substance suitable to deliver the compounds provided herein to the patient. Pharmaceutically acceptable carriers are well known in the art and include, for example, aqueous solutions such as (sterile) water or physiologically buffered saline or other solvents or vehicles such as glycols, glycerol, oils such as olive oil or injectable organic esters, alcohol, fats, waxes, and inert solids. A pharmaceutically acceptable carrier may further contain physiologically acceptable compounds that act for example to stabilize or to increase the absorption of the composition provided herein. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the composition. Pharmaceutically acceptable adjuvants, buffering agents, dispersing agents, and the like, may also be incorporated into the pharmaceutical compositions.

For oral administration, the active ingredient can be administered in solid dosage forms, such as capsules, tablets, and powders, or liquid dosage forms, such as elixirs, syrups, and suspensions. Active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that may be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar-coated or film-coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

The compositions provided herein are however preferably administered parenterally. Preparations of the compositions provided herein for parenteral administration must be sterile. Sterilization is readily accomplished by filtration through sterile filtration membranes, optionally prior to or following lyophilization and reconstitution. The parenteral route for administration of compositions provided herein is in accord with known methods, e.g. injection or infusion by intravenous, intraperitoneal, intramuscular, intraarterial, or intralesional routes. The compositions provided herein may be administered continuously by infusion or by bolus injection. Methods for preparing parenterally administrable compositions are well known in the art.

EXAMPLES

Materials and Methods
Antibodies

ADC1 (or chADC1) is an antibody specific for a human tumor antigen, generated in mice and converted to human IgG1 isotype. SGN-35 is specific for human CD30 and is described in Maeda et al. 2010 Cancer Sci. 101(1):224-230 and U.S. Pat. No. 7,090,843. ADC1 and SGN-35 are full length tetrameric antibodies with one acceptor glutamine per heavy chain at amino acid residue 295 (Kabat EU), i.e. a total of two acceptor glutamines. Unless otherwise indicated, ADC1 and SGN-35 antibodies without the Fc mutations used in BTG coupling reaction were deglycosylated with PNGase F.

Variants of antibodies ADC1 and SGN-35 were constructed that contained a N297S mutation; this antibody thus had one acceptor glutamine per heavy chain at amino acid residues 295 (Kabat EU), i.e. a total of two acceptor glutamines per tetrameric antibody, and were aglycosylated.

Variants of antibodies ADC1 and SGN-35 were also constructed that contained a N297Q mutation; these antibodies thus had two acceptor glutamine per heavy chain at amino acid residues 295 and 297 (Kabat EU), i.e. a total of four acceptor glutamines, and were aglycosylated.

For ADC1 and SGN-35, two different sequences having the N297S or N297Q mutations in the human constant region of γ1 antibodies were synthesized by MWG-Biotech. These two mutated sequences were designed respectively N297S and N297Q.

The nucleic acid and amino acid sequences synthesized for the N297S construct (the mutation is underlined) is shown below:

(SEQ ID NO: 1)
GGGCCCAAGCGTGTTCCCCCTGGCCCCCAGCAGCAAGAGCACCAGCGG

CGGCACAGCCGCCCTGGGCTGCCTGGTGAAGGACTACTTCCCCGAGCC

CGTGACCGTGTCCTGGAACAGCGGAGCCCTGACCTCCGGCGTGCACAC

CTTCCCCGCCGTGCTGCAGAGCAGCGGCCTGTACAGCCTGAGCAGCGT

GGTGACCGTGCCCAGCAGCAGCCTGGGCACCCAGACCTACATCTGTAA

CGTGAACCACAAGCCCAGCAACACCAAGGTGGACAAGAGAGTGGAGCC

CAAGAGCTGTGACAAGACCCACACCTGCCCCCCCTGCCCAGCCCCCGA

GCTGCTGGGCGGACCCAGCGTGTTCCTGTTCCCCCCCAAGCCCAAGGA

CACCCTGATGATCAGCAGAACCCCCGAGGTGACCTGTGTGGTGGTGGA

CGTGTCCCACGAGGACCCAGAGGTGAAGTTCAACTGGTACGTGGACGG

CGTGGAGGTGCACAACGCCAAGACCAAGCCCAGAGAGGAGCAGTACAG

CAGCACCTACAGGGTGGTGTCCGTGCTGACCGTGCTGCACCAGGACTG

GCTGAACGGCAAGGAGTACAAGTGTAAGGTGTCCAACAAGGCCCTGCC

AGCCCCAATCGAAAAGACCATCAGCAAGGCCAAGGGCCAGCCAAGAGA

GCCCCAGGTGTACACCCTGCCACCCAGCAGGGAGGAGATGACCAAGAA

CCAGGTGTCCCTGACCTGTCTGGTGAAGGGCTTCTACCCAAGCGACAT

CGCCGTGGAGTGGGAGAGCAACGGCCAGCCCGAGAACAACTACAAGAC

CACCCCCCCAGTGCTGGACAGCGACGGCAGCTTCTTCCTGTACAGCAA

GCTGACCGTGGACAAGAGCAGATGGCAGCAGGGCAACGTGTTCAGCTG

CTCCGTGATGCACGAGGCCCTGCACAACCACTACACCCAGAAGAGCCT

GAGCCTGTCCCCAGGCAAGTGATGAATTC (SEQ ID NO: 2)
G P S V F P L A P S S K S T S G G T A A L G C L

V K D Y F P E P V T V S W N S G A L T S G V H T

F P A V L Q S S G L Y S L S S V V T V P S S S L

-continued
G T Q T Y I C N V N H K P S N T K V D K R V E P

K S C D K T H T C P P C P A P E L L G G P S V F

L F P P K P K D T L M I S R T P E V T C V V V D

V S H E D P E V K F N W Y V D G V E V H N A K T

K P R E E Q Y S S T Y R V V S V L T V L H Q D W

L N G K E Y K C K V S N K A L P A P I E K T I S

K A K G Q P R E P Q V Y T L P P S R E E M T K N

Q V S L T C L V K G F Y P S D I A V E W E S N G

Q P E N N Y K T T P P V L D S D G S F F L Y S K

L T V D K S R W Q Q G N V F S C S V M H E A L H

N H Y T Q K S L S L S P G K

The nucleic acid and amino acid sequences synthesized for the N297Q construct (the mutation is underlined) is shown below:

(SEQ ID NO: 3)
GGGCCCAAGCGTGTTCCCCCTGGCCCCAGCAGCAAGAGCACCAGCG

GCGGCACAGCCGCCCTGGGCTGCCTGGTGAAGGACTACTTCCCCGAG

CCCGTGACCGTGTCCTGGAACAGCGGAGCCCTGACCTCCGGCGTGCA

CACCTTCCCCGCCGTGCTGCAGAGCAGCGGCCTGTACAGCCTGAGCA

GCGTGGTGACCGTGCCCAGCAGCAGCCTGGGCACCCAGACCTACATC

TGTAACGTGAACCACAAGCCCAGCAACACCAAGGTGGACAAGAGAGT

GGAGCCCAAGAGCTGTGACAAGACCCACACCTGCCCCCCCTGCCCAG

CCCCCGAGCTGCTGGGCGGACCCAGCGTGTTCCTGTTCCCCCCCAAG

CCCAAGGACACCCTGATGATCAGCAGAACCCCCGAGGTGACCTGTGT

GGTGGTGGACGTGTCCCACGAGGACCCAGAGGTGAAGTTCAACTGGT

ACGTGGACGGCGTGGAGGTGCACAACGCCAAGACCAAGCCCAGAGAG

GAGCAGTACCAAAGCACCTACAGGGTGGTGTCCGTGCTGACCGTGCT

GCACCAGGACTGGCTGAACGGCAAGGAGTACAAGTGTAAGGTGTCCA

ACAAGGCCCTGCCAGCCCCAATCGAAAAGACCATCAGCAAGGCCAAG

GGCCAGCCAAGAGAGCCCCAGGTGTACACCCTGCCACCCAGCAGGGA

GGAGATGACCAAGAACCAGGTGTCCCTGACCTGTCTGGTGAAGGGCT

TCTACCCAAGCGACATCGCCGTGGAGTGGGAGAGCAACGGCCAGCCC

GAGAACAACTACAAGACCACCCCCCCAGTGCTGGACAGCGACGGCAG

CTTCTTCCTGTACAGCAAGCTGACCGTGGACAAGAGCAGATGGCAGC

AGGGCAACGTGTTCAGCTGCTCCGTGATGCACGAGGCCCTGCACAAC

CACTACACCCAGAAGAGCCTGAGCCTGTCCCCAGGCAAGTGATGAAT

TC (SEQ ID NO: 4)
G P S V F P L A P S S K S T S G G T A A L G C L

V K D Y F P E P V T V S W N S G A L T S G V H T

F P A V L Q S S G L Y S L S S V V T V P S S S L

G T Q T Y I C N V N H K P S N T K V D K R V E P

K S C D K T H T C P P C P A P E L L G G P S V F

L F P P K P K D T L M I S R T P E V T C V V V D

V S H E D P E V K F N W Y V D G V E V H N A K T

K P R E E Q Y Q S T Y R V V S V L T V L H Q D W

L N G K E Y K C K V S N K A L P A P I E K T I S

K A K G Q P R E P Q V Y T L P P S R E E M T K N

Q V S L T C L V K G F Y P S D I A V E W E S N G

Q P E N N Y K T T P P V L D S D G S F F L Y S K

L T V D K S R W Q Q G N V F S C S V M H E A L H

N H Y T Q K S L S L S P G K

These sequences were then digested from the MWG-Biotech cloning vector with the ApaI and EcoRI restriction enzymes and cloned into the vector B digested with the same restriction enzymes (B N297S and B N297Q). Light chain and heavy chain of the variable domains of the chADC1 antibody were amplified by PCR and the purified products of the PCR were cloned together into the vectors B N297S and N297Q using the InFusion cloning system (Ozyme) to create bicistronic vectors. The bicistronic vectors generated were then sequenced and validated prior to cell transfection. CHO cells were transfected with the vectors encoding ADC1 or SGN-30 N297S and N297Q and cells were grown in rolling bottle to produce large quantities of antibodies that were purified from the harvested supernatant.

Enzymatic Modification of Antibodies

Cadaverin-dansyl was purchased from Zedira (Darmstadt, Germany). NH2-PEG-MMAE was synthesized. PEGN3 was purchased from Click Chemistry Tools, LLC. (AZ). Antibody in PBS was incubated with the indicated number equivalents of ligand (expressed as equivalents of the number of acceptor glutamines) and the indicated number of activity units (U) per mL bacterial transglutaminase (BT-Gase, Zedira, Darmstadt, Germany) overnight at 37° C., unless otherwise indicated. Excess of ligand and the BTGase were removed by centrifugation-dialysis (Vivaspin MWCO 50 kDa, Vivascience, Winkel, Switzerland).

LC-MS Analysis

LC-MS analysis were performed on MicroTOF Q II BRUKER mass spectrometer. Two methods were used to analyzed reduced antibodies or full-length antibodies. For reduced antibodies, 10 µg of antibody were mixed with DTT (final concentration 10 mM) and incubated 30 min at 37° C. Samples (10 µl) were chromatographed on Aeris WIDE-PORE 3.6 U XB-C18 (250×2.1 mm) heated to 80° C. at a flow-rate of 0.35 ml/min. Initial condition: 10% B, followed by a gradient: 20% B at 1 min; 46.2% B at 20 min; 10% B at 21 min; Total run time: 31 min(solvent A: H20+0.1% AF+1/50000 TFA; solvent B: 50% ACN+50% IPA+0.1AF+1/50000 TFA). For full-length antibodies, samples (10 µL) were chromatographed on PLRPS 4000A (50×2.1 mm) column heated to 70° C. at a flow-rate of 0.35 ml/min. Initial conditions: 5% B, followed by a gradient: 5% B at 2 min; 50% B at 5 min; 50% B at 7 min; 5% B at 8 min; Total run time: 15 min (solvent A: H20+0.1% AF; solvent B: ACN+0.1AF). The eluent was ionized using an electrospray source. Data were collected with Data Analysis and deconvolution was performed using MaxEnt.

HIC Analysis

Hydrophobic interaction chromatography (HIC) analysis was conducted on Agilent Technologies 1200 series UPLC system using a TSKgel Butyl-NPR column, 4.6×35 mm, 2.5 mm particle size (Tosoh Bioscience) with a linear gradient of 100% mobile phase A (1.5 M $(NH_4)_2SO_4$ in 25 mM potassium phosphate) to 70% mobile phase B (25 mM potassium phosphate, pH 7.0, 25% isopropanol) in 14 min. The flow rate was set at 1 mL/min and the column temperature was maintained at 30° C. HIC analysis of ADC1dgl coupled to a Dansyl cadaverine substrate (Example 1) was performed using double detection by UV (280 nm) and fluorescence (λ excitation at 250 nm, λ emission at 535 nm). The overall mean drug loading or DAR (Drug Antibody Ratio) is calculated as the weighted average using the integrated areas of the constituent peaks and the drug loading of each peak as the weighting factor.

Example 1

Coupling Plateau for Large, Hydrophobic and/or Charged Payloads

BTG generally is unable to achieve high levels of coupling (high DARs) at the acceptor glutamine at residue 295 of linkers with large and/or hydrophobic organic molecules representative of cytotoxic drugs. To explore the possibility that optimized reactions might permit quantitative coupling reaction, parameters were explored, including effect of pH, temperature, linker stoichiometry. All reactions were monitored by HIC analysis or LC-MS. Samples for HIC analysis were taken after time periods and directly injected in HIC. Samples for MS analysis were frozen to stop the reaction.

FIG. 1 depicts the labeling of enzymatically deglycosylated ADC1 with dansyl-cadaverin substrate at different concentrations of BTGase, showing that higher labeling yields were achieved with increasing enzyme concentrations for BTGase, with optimized reaction conditions at 6 U/ml BTG, 1 mg/ml mAb, 20 equivalents of linker substrate, 18 h duration, pH 7.4 and temperature of 37° C. When the small dansyl-cadaverin substrate was used, high levels of conjugation were generally achieved.

However, using a NH2-PEG-vc-PAB-MMAE linker comprising a large and hydrophobic auristatin moiety (see structure below), high DARs could not be reached.

In order to improve coupling, N297S or N297Q mutations in the CH2 domain were developed to avoid PNGaseF-mediated generation of a negatively charged aspartic acid at the +2 position relative to the acceptor glutamine Q295, and to additionally provide a second acceptor glutamine per heavy chain. These aglycosylated antibody variants significantly improved coupling compared to enzymatically deglycosylated antibody, however when using the NH2-PEG-vc-PAB-MMAE linker a plateau reached was at a DAR of 1.6 to ADC1-N297S antibody (2 acceptor glutamines per antibody) and a DAR of 3.5 for an ADC1-N297Q antibody (4 acceptor glutamines per antibody). The aglycosylated antibody variants were thus used for subsequent experiments.

Example 2

BTG Deamidates Acceptor Glutamine in the CH2 Domain

In order to explain the observation that BTG-mediated coupling of certain substrates onto antibodies does not reach completion despite optimized reaction conditions and Q297 variants, the effect of BTG on antibodies in the absence of amino (linker) substrate was investigated.

Antibody ADC1 having either a N297S mutation (one acceptor glutamine per heavy chain) or a N297Q mutation (two acceptor glutamines per heavy chain) was incubated with BTG, with a small, non-hydrophobic linker substrate having the structure below, with the linker being added either at the outset, after 2 hours of incubation or after 17 hours of incubation (overnight, ON), with reaction conditions of 6 U/ml BTG, 5 mg/ml mAb, 20 equivalents of linker substrate per acceptor glutamine, pH 7.4 and temperature of 37° C.

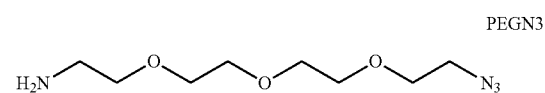

PEGN3

The coupling reaction was run overnight, with samples analyzed at 20 and 22 hours following the start of the reaction. Coupling was monitored using LC/MS (reduced mAb). The three different experimental settings are summarized as follows:

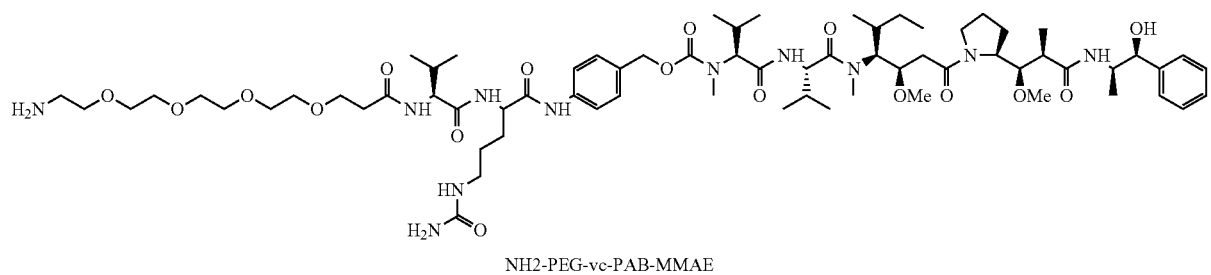 [SMILES: CCC(C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)C(CCCNC(N)=O)NC(=O)[C@@H](NC(=O)CCOCCOCCOCCOCCN)C(C)C)cc1)C(C)C]

NH2-PEG-vc-PAB-MMAE

|  | Setting A:<br>ADC1 (N297S or N297Q) + linker | Setting B:<br>ADC1 (N297S or N297Q)/BTG 2H | Setting C:<br>ADC1 (N297S or N297Q) + linker/BTG ON |
|---|---|---|---|
| Coupling | T = 0: mAb + linker + BTG/37° C. | T = 0: mAb + BTG/37° C.<br>+2 hrs: + linker | T = 0: mAb + BTG/37° C.<br>+17 hrs: + linker |
| Analysis | +20 hrs: sample t1<br>+22 hrs: sample t2 | +20 hrs: sample t1<br>+22 hrs: sample t2 | +20 hrs: sample t1<br>+22 hrs: sample t2 |

Figure 2A:
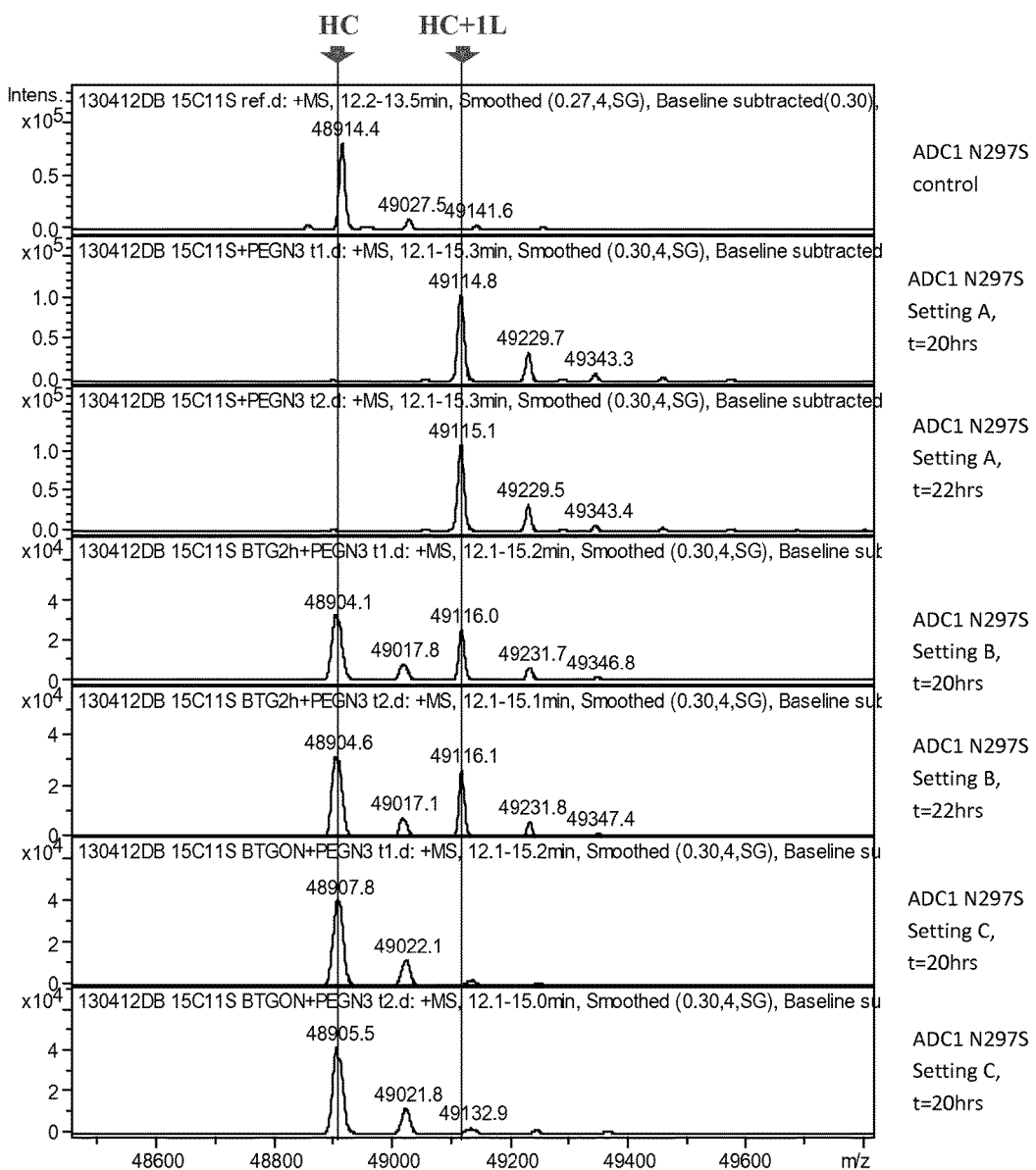
FIGS. 2A and 2B show the MS/MS spectrum showing increased deamidation and decreased coupling with increasing BTG:antibody ratio using a linker substrate comprising a larger hydrophobic auristatin drug.

FIG. 2A shows coupling for antibody ADC1, N297S variant. The control antibody ADC1-Q297S was not conjugated to linker, however Settings A, B and C differed significantly in the completion of the reaction. Despite allowing overnight for completion of reactions (where a plateau is reached), figures show that Setting B permitted less coupling than Setting A (fewer heavy chains with one Coupling reactions were conducted using antibody SGN35, variant N297S was tested at concentrations of 1-5 mg/mL. A large hydrophobic linker (NH2-PEG-vc-PAB-MMAE, see structure below) was provided at either 10 or 20 equivalents per acceptor glutamine, BTG was tested at 0.5-2 U/mL, in PBS1× at temperature of 37° C.

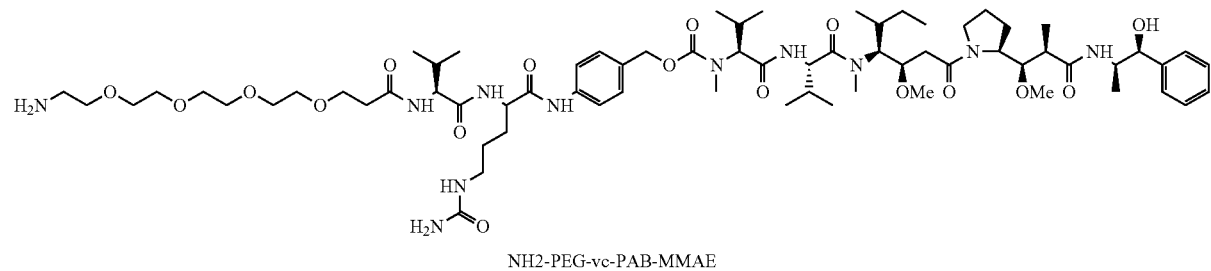 [SMILES: CCC(C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)C(CCCNC(N)=O)NC(=O)[C@@H](NC(=O)CCOCCOCCOCCOCCN)C(C)C)cc1)C(C)C]

Figure 2B:
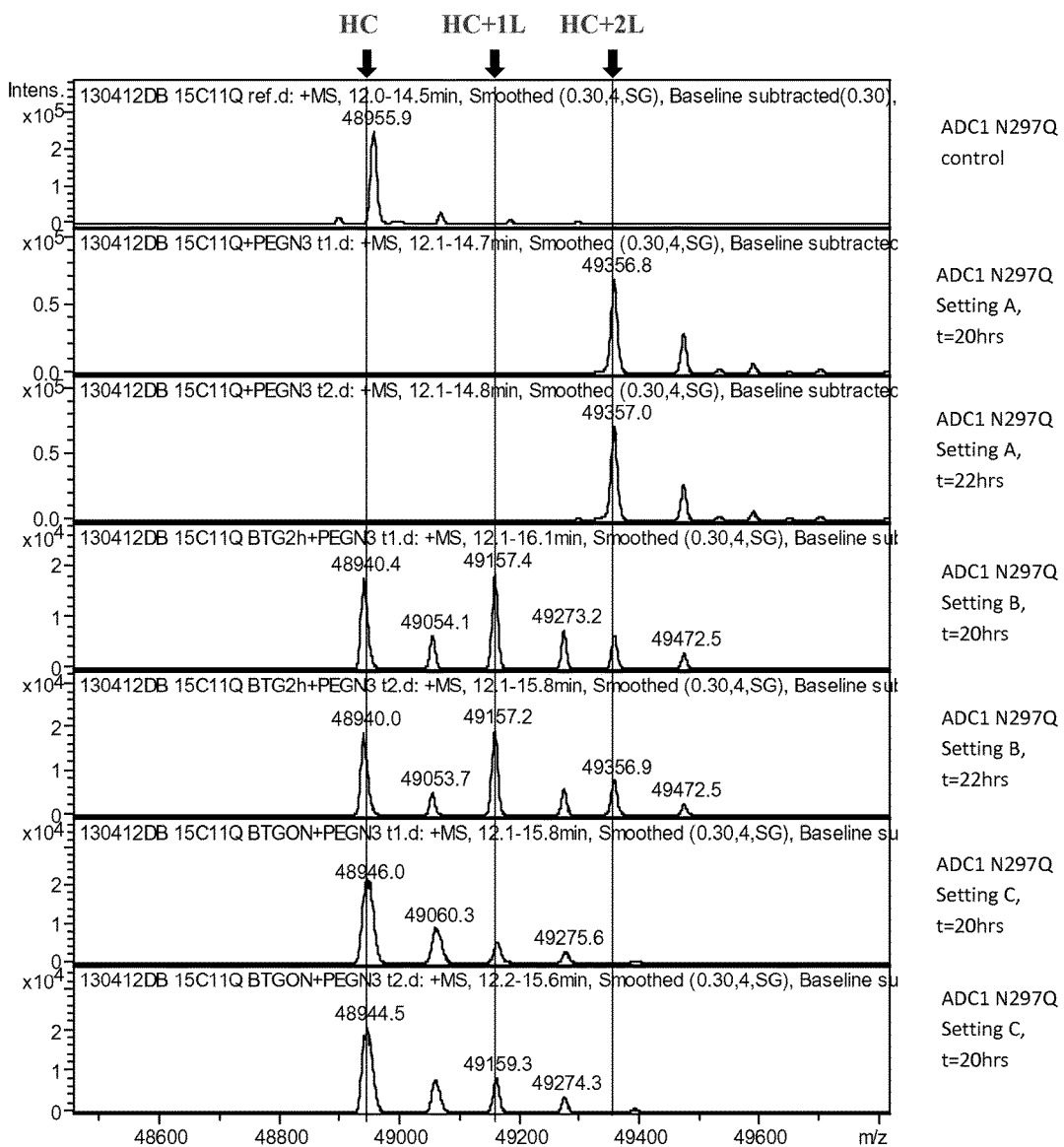

NH2-PEG-vc-PAB-MMAE linker (HC+1L), and Setting C coupled less completely than Setting B. Similar results were observed using the ADC1 N297Q variant having two acceptor glutamines per heavy chain. FIG. 2B shows coupling for antibody ADC1, N297Q variant. The control antibody ADC1-Q297Q was not conjugated to linker, however Setting B permitted less coupling than Setting A (fewer heavy chains with two linkers (HC+2L), and Setting C coupled less than Setting B. Setting C additionally had fewer heavy chains with one linker (HC+1L) than Setting B and was made up mostly of uncoupled heavy chains.

It is believed that BTG is capable of causing a deamidation of acceptor glutamines on heavy chains which then are no longer available for coupling by BTG. Interestingly, the deamidation occurred rapidly upon incubation and at similar kinetics as are observed for coupling of linkers, suggesting that the deamidation is influencing the reaction as of the outset, possibly by accepting water as substrate in competition with linker substrate.

Example 3

Design of an Improved Production Process

While the small cadavarin-dansyl substrate used in Example 1 couples well in optimized reaction conditions, we observe that difficult BTG substrates (e.g. large, charged and/or hydrophobic linker substrates) do not go to completion, reaching a coupling plateau at a DAR of about 1.6 (one acceptor glutamine per heavy chain) and about 3.5 (two acceptor glutamines per heavy chain). We hypothesized that in challenging coupling settings, water may compete with linker as a substrate for BTG coupling, leading to deamidation of acceptor glutamines. To investigate whether decreasing the BTG activity in a reaction vessel relative to the amount of antibody substrate available could decrease the amount of deamidated acceptor glutamines we evaluated different "low activity" BTG reaction conditions.

Figure 3:
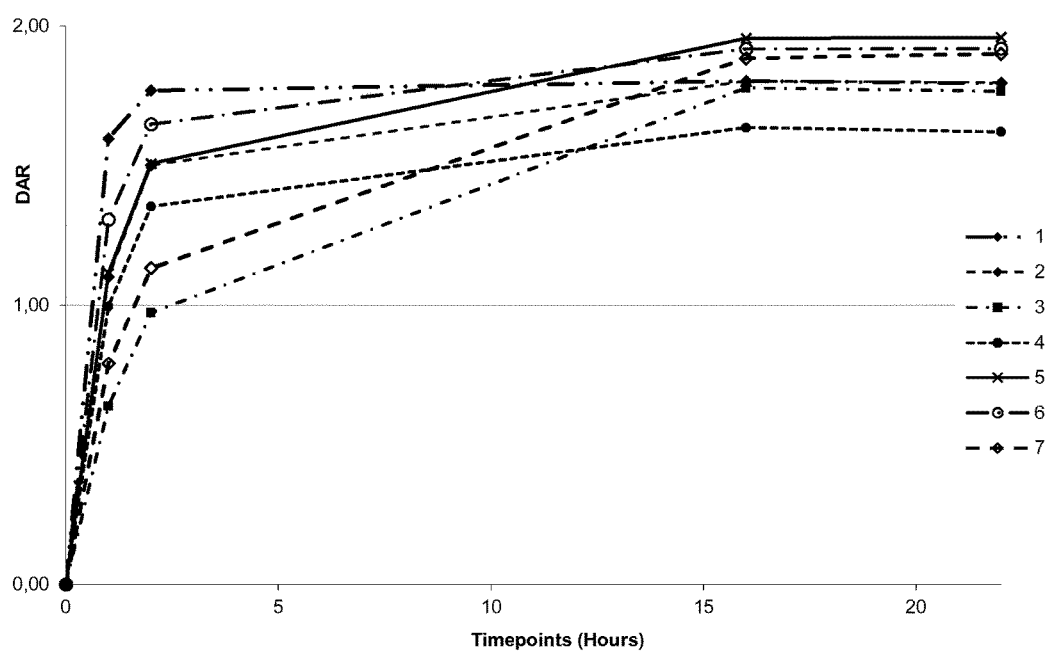
FIG. 3 shows improved enzymatic modification of N297S antibody heavy chains with a large hydrophobic linker (auristatin toxin) payload using different low levels of BTG activity, to obtain a DAR of 1.98.

The results are shown in FIG. 3, showing drug-antibody ratio (DAR) for seven conditions tested. The conditions 1-7 are shown below in Table 1. It can be seen that at higher ratios of BTG activity:antibody (or acceptor glutamines), a coupling plateau is reached at a DAR of about 1.6 (e.g. condition #4). However, when the ratio of BTG activity:antibody (or acceptor glutamines) is lowered, e.g. conditions 5-7, high DARs are achieved, including a DAR of above 1.90 (e.g. 1.96).

Concentration of linker substrate additionally influenced the reaction. However, reaction conditions 6 and 7 which used lower amounts of linker substrate (10 equivalents of linker substrate per acceptor glutamine) reached high levels of completion, further providing improved processes that use lower amounts of starting material.

TABLE 1

| ID | mAb (mg/mL) | linker | BTG (U/mL) | U BTG per nmole acceptor glutamine | DAR achieved |
|---|---|---|---|---|---|
| #1 | 1 | 20 eq/site | 2 | 0.15 | 1.79 |
| #2 | 1 | 20 eq/site | 1 | 0.075 | 1.80 |
| #3 | 1 | 20 eq/site | 0.5 | 0.0375 | 1.76 |
| #4 | 1 | 10 eq/site | 1 | 0.075 | 1.62 |
| #5 | 5 | 20 eq/site | 2 | 0.03 | 1.96 |
| #6 | 5 | 10 eq/site | 2 | 0.03 | 1.92 |
| #7 | 5 | 10 eq/site | 1 | 0.015 | 1.90 |

From the results it was seen that modifying the process to decrease BTG activity as as function of the amount of available acceptor glutamine on antibodies is able to drive the conjugation to completion. In view of differing activities across different BTG enzymes (e.g. suppliers) and among product batches, it will be advantageous to incorporate the activity level of BTG in process conditions.

TABLE 2

| $C_n$ | X | L | V | Y | Z |
|---|---|---|---|---|---|
| $(CH_2)_5$ | NH | —(C=O)—CH$_2$— | — | — | Charged compound |
| $(CH_2)_5$ | NH | —(C=O)—(CH$_2$)$_5$— | — | Spacer system | Large, charged or hydrophobic compound; toxin; auristatin; MMAE |
| $(CH_2)_5$ | NH | —(C=O)—(CH$_2$)$_5$— | Cleavable or non-cleavable linker; di- or tri- or oligo peptide; val-cit | Spacer system | Large, charged or hydrophobic compound; toxin; auristatin; MMAE |
| $(CH_2)_5$ | NH | —(C=O)—(CH$_2$)$_5$— | Cleavable or non-cleavable linker; di- or tri- or oligo peptide; val-cit; or absent | Spacer system | Large, charged or hydrophobic compound; toxin; auristatin; MMAE |
| $(CH_2)_{10}$ | NH | —(C=O)—(CH$_2$)$_5$— | Cleavable or non-cleavable linker; di- or tri- or oligo peptide; val-cit; or absent | Spacer system | Large, charged or hydrophobic compound; toxin; auristatin; MMAE |
| $(CH_2)_{15}$ | NH | —(C=O)—(CH$_2$)$_5$— | Cleavable or non-cleavable linker; di- or tri- or oligo peptide; val-cit; or absent | Spacer system | Large, charged or hydrophobic compound; toxin; auristatin; MMAE |
| $(CH_2)_5$ | NH | —CH$_2$—(CH$_2$—O—CH$_2$)$_4$—CH$_2$— | Cleavable or non-cleavable linker; di- or tri- or oligo peptide; val-cit; or absent | Spacer system | Large, charged or hydrophobic compound; toxin; auristatin; MMAE |
| $(CH_2)_5$ | NH | —CH$_2$—(CH$_2$—O—CH$_2$)$_{12}$—CH$_2$— | Cleavable or non-cleavable linker; di- or tri- or oligo peptide; val-cit; or absent | Spacer system | Large, charged or hydrophobic compound; toxin; auristatin; MMAE |
| $(CH_2)_5$ | NH | —CH$_2$—(CH$_2$—O—CH$_2$)$_{1-24}$—CH$_2$— | Cleavable or non-cleavable linker; di- or tri- or oligo peptide; val-cit; or absent | Spacer system | Large, charged or hydrophobic compound; toxin; auristatin; MMAE |
| $(CH_2)_{10}$ | NH | —CH$_2$—(CH$_2$—O—CH$_2$)$_4$—CH$_2$— | Cleavable or non-cleavable linker; di- or tri- or oligo peptide; val-cit; or absent | Spacer system | Large, charged or hydrophobic compound; toxin; auristatin; MMAE |
| $(CH_2)_{15}$ | NH | —CH$_2$—(CH$_2$—O—CH$_2$)$_4$—CH$_2$— | Cleavable or non-cleavable linker; di- or tri- or oligo peptide; val-cit; or absent | Spacer system | Large, charged or hydrophobic compound; toxin; auristatin; MMAE |
| $(CH_2)_5$ | NH | —(C=O)—CH$_2$—(CH$_2$—O—CH$_2$)$_4$—CH$_2$— | Cleavable or non-cleavable linker; di- or tri- or oligo peptide; val-cit; or absent | Spacer system | Large, charged or hydrophobic compound; toxin; auristatin; MMAE |
| $(CH_2)_{10}$ | NH | —(C=O)—CH$_2$—(CH$_2$—O—CH$_2$)$_{1-24}$—CH$_2$— | Cleavable or non-cleavable linker; di- or tri- or oligo peptide; val-cit; or absent | Spacer system | Large, charged or hydrophobic compound; toxin; auristatin; MMAE |
| $(CH_2)_{15}$ | NH | —(C=O)—CH$_2$—(CH$_2$—O—CH$_2$)$_{1-24}$—CH$_2$— | Cleavable or non-cleavable linker; di- or tri- or oligo peptide; val-cit; or absent | Spacer system | Large, charged or hydrophobic compound; toxin; auristatin; MMAE |
| $(CH_2)_5$ | NH | —(C=O)—(CH$_2$)$_{10-20}$— | Cleavable or non-cleavable linker; di- or tri- or oligo peptide; val-cit; or absent | Spacer system | Large, charged or hydrophobic compound; toxin; auristatin; MMAE |
| $(CH_2)_{10}$ | NH | —(C=O)—(CH$_2$)$_{10-20}$— | Cleavable or non-cleavable linker; di- or tri- or oligo peptide; val-cit; or absent | Spacer system | Large, charged or hydrophobic compound; toxin; auristatin; MMAE |
| $(CH_2)_{15}$ | NH | —(C=O)—(CH$_2$)$_{10-20}$— | Cleavable or non-cleavable linker; di- or tri- or oligo peptide; val-cit; or absent | Spacer system | Large, charged or hydrophobic compound; toxin; auristatin; MMAE |

TABLE 2-continued

| $C_n$ | X | L | V | Y | Z |
|---|---|---|---|---|---|
| $(CH_2)_5$ | NH | —$(CH_2)_{1-6}$— | Cleavable or non-cleavable linker; di- or tri- or oligo peptide; val-cit; or absent | Spacer system | Large, charged or hydrophobic compound; toxin; auristatin; MMAE |
| $(CH_2)_{10}$ | NH | —$(CH_2)_{1-6}$— | Cleavable or non-cleavable linker; di- or tri- or oligo peptide; val-cit; or absent | Spacer system | Large, charged or hydrophobic compound; toxin; auristatin; MMAE |
| $(CH_2)_{15}$ | NH | —$(CH_2)_{1-6}$— | Cleavable or non-cleavable linker; di- or tri- or oligo peptide; val-cit; or absent | Spacer system | Large, charged or hydrophobic compound; toxin; auristatin; MMAE |
| $(CH_2)_5$ | NH | —$(CH_2)_{10-20}$— | Cleavable or non-cleavable linker; di- or tri- or oligo peptide; val-cit; or absent | Spacer system | Large, charged or hydrophobic compound; toxin; auristatin; MMAE |
| $(CH_2)_{10}$ | NH | —$(CH_2)_{10-20}$— | Cleavable or non-cleavable linker; di- or tri- or oligo peptide; val-cit; or absent | Spacer system | Large, charged or hydrophobic compound; toxin; auristatin; MMAE |
| $(CH_2)_{15}$ | NH | —$(CH_2)_{10-20}$— | Cleavable or non-cleavable linker; di- or tri- or oligo peptide; val-cit; or absent | Spacer system | Large, charged or hydrophobic compound; toxin; auristatin; MMAE |
| $(CH_2)_5$ | NH | —(C=O)—O—$CH_2$— | Cleavable or non-cleavable linker; di- or tri- or oligo peptide; val-cit; or absent | Spacer system | Large, charged or hydrophobic compound; toxin; auristatin; MMAE |
| $(CH_2)_{10}$ | NH | —(C=O)—O—$CH_2$— | Cleavable or non-cleavable linker; di- or tri- or oligo peptide; val-cit; or absent | Spacer system | Large, charged or hydrophobic compound; toxin; auristatin; MMAE |
| $(CH_2)_{15}$ | NH | —(C=O)—O—$CH_2$— | Cleavable or non-cleavable linker; di- or tri- or oligo peptide; val-cit; or absent | Spacer system | Large, charged or hydrophobic compound; toxin; auristatin; MMAE |
| $(CH_2)_5$ | NH | —(C=O)—O—$(CH_2)_{2-20}$— | Cleavable or non-cleavable linker; di- or tri- or oligo peptide; val-cit; or absent | Spacer system | Large, charged or hydrophobic compound; toxin; auristatin; MMAE |
| $(CH_2)_{10}$ | NH | —(C=O)—O—$(CH_2)_{2-20}$— | Cleavable or non-cleavable linker; di- or tri- or oligo peptide; val-cit; or absent | Spacer system | Large, charged or hydrophobic compound; toxin; auristatin; MMAE |
| $(CH_2)_{15}$ | NH | —(C=O)—O—$(CH_2)_{2-20}$— | Cleavable or non-cleavable linker; di- or tri- or oligo peptide; val-cit; or absent | Spacer system | Large, charged or hydrophobic compound; toxin; auristatin; MMAE |
| $(CH_2)_5$ | NH | Amino acid, di- or tri- or oligo peptide | Cleavable or non-cleavable linker; di- or tri- or oligo peptide; val-cit; or absent | Spacer system | Large, charged or hydrophobic compound; toxin; auristatin; MMAE |
| $(CH_2)_{10}$ | NH | Amino acid, di- or tri- or oligo peptide | Cleavable or non-cleavable linker; di- or tri- or oligo peptide; val-cit; or absent | Spacer system | Large, charged or hydrophobic compound; toxin; auristatin; MMAE |
| $(CH_2)_{15}$ | NH | Amino acid, di- or tri- or oligo peptide | Cleavable or non-cleavable linker; di- or tri- or oligo peptide; val-cit; or absent | Spacer system | Large, charged or hydrophobic compound; toxin; auristatin; MMAE |

TABLE 2-continued

| $C_h$ | X | L | V | Y | Z |
|---|---|---|---|---|---|
| $(CH_2)_5$ | NH | $-(C=O)-CH_2-S-$ [maleimide-N linkage] | Cleavable or non-cleavable linker; di- or tri- or oligo peptide; val-cit; or absent | Spacer system; $CH_2-(CH_2-O-CH_2)_4-CH_2-$ | Large, charged or hydrophobic compound; toxin; auristatin; MMAE |
| $(CH_2)_5$ | NH | $-(C=O)-CH_5-S-$ [maleimide-N linkage] | Cleavable or non-cleavable linker; di- or tri- or oligo peptide; val-cit; or absent | Spacer system; $CH_2-(CH_2-O-CH_2)_4-CH_2-$ | Large, charged or hydrophobic compound; toxin; auristatin; MMAE |
| $(CH_2)_5$ | NH | $-CH_2-(CH_2-O-CH_2)_{1\text{-}24}-CH_2-S-$ [succinimide-N linkage] | Cleavable or non-cleavable linker; di- or tri- or oligo peptide; val-cit; or absent | Spacer system; $CH_2-(CH_2-O-CH_2)_4-CH_2-$ | Large, charged or hydrophobic compound; toxin; auristatin; MMAE |
| $-CH_2-(CH_2-O-CH_2)_3-CH_2-$ | NH | — | Cleavable or non-cleavable linker; di- or tri- or oligo peptide; val-cit; or absent | Spacer system | Large, charged or hydrophobic compound; toxin; auristatin; MMAE |
| $-CH_2-(CH_2-O-CH_2)_3-CH_2-$ | NH | $-CH_2-(CH_2-O-CH_2)_{1\text{-}24}-CH_2-$ | Cleavable or non-cleavable linker; di- or tri- or oligo peptide; val-cit; or absent | Spacer system | Large, charged or hydrophobic compound; toxin; auristatin; MMAE |
| $-CH_2-(CH_2-O-CH_2)_3-CH_2-$ | NH | $-(C=O)-CH_2-(CH_2-O-CH_2)_{1\text{-}24}-CH_2-$ | Cleavable or non-cleavable linker; di- or tri- or oligo peptide; val-cit; or absent | Spacer system | Large, charged or hydrophobic compound; toxin; auristatin; MMAE |
| $-O-(CH_2)_{1\text{-}5}$ | NH | — | Cleavable or non-cleavable linker; di- or tri- or oligo peptide; val-cit; or absent | Spacer system | Large, charged or hydrophobic compound; toxin; auristatin; MMAE |
| $-O-CH_2-(CH_2-O-CH_2)_3-CH_2-$ | NH | — | Cleavable or non-cleavable linker; di- or tri- or oligo peptide; val-cit; or absent | Spacer system | Large, charged or hydrophobic compound; toxin; auristatin; MMAE |
| $-O-CH_2-(CH_2-O-CH_2)_3-CH_2-$ | NH | $-CH_2-(CH_2-O-CH_2)_{1\text{-}24}-CH_2-$ | Cleavable or non-cleavable linker; di- or tri- or oligo peptide; val-cit; or absent | Spacer system | Large, charged or hydrophobic compound; toxin; auristatin; MMAE |
| $-O-CH_2-(CH_2-O-CH_2)_3-CH_2-$ | NH | $-(C=O)-CH_2-(CH_2-O-CH_2)_{1\text{-}24}-CH_2-$ | Cleavable or non-cleavable linker; di- or tri- or oligo peptide; val-cit; or absent | Spacer system | Large, charged or hydrophobic compound; toxin; auristatin; MMAE |
| $(CH_2)_4-CH(NH_2)-(C=O)-$ | NH | — | — | — | Charged compound |
| $(CH_2)_4-CH(NH_2)-(C=O)-$ | NH | — | di- or tri- or oligo peptide; val-cit | Spacer system | Large, charged or hydrophobic compound; toxin; auristatin; MMAE |

TABLE 2-continued

| $(C)_n$ | X | L | V | Y | Z |
|---|---|---|---|---|---|
| $(CH_2)_4-CH(NH_2)-(C=O)-$ | NH | $-(CH_2)_{1-6}-$ | Cleavable or non-cleavable linker; di- or tri- or oligo peptide; val-cit; or absent | Spacer system | Large, charged or hydrophobic compound; toxin; auristatin; MMAE |
| $(CH_2)_4-CH(NH_2)-(C=O)-$ | NH | $-(CH_2)_5-$ | Cleavable or non-cleavable linker; di- or tri- or oligo peptide; val-cit; or absent | Spacer system | Large, charged or hydrophobic compound; toxin; auristatin; MMAE |
| $(CH_2)_4-CH(NH_2)-(C=O)-$ | NH | $-CH_2-(CH_2-O-CH_2)_{1-24}-CH_2-$ | Cleavable or non-cleavable linker; di- or tri- or oligo peptide; val-cit; or absent | Spacer system | Large, charged or hydrophobic compound; toxin; auristatin; MMAE |
| $(CH_2)_5$ | NH | — | — | Spacer system; $(CH_2)_5$ | Large, charged or hydrophobic compound; toxin; auristatin; MMAF |
| $(CH_2)_{6-10}$ | NH | — | — | Spacer system; $(CH_2)_5$ | Large, charged or hydrophobic compound; toxin; auristatin; MMAF |
| $(CH_2)_{15}$ | NH | — | — | Spacer system; $(CH_2)_5$ | Large, charged or hydrophobic compound; toxin; auristatin; MMAF |
| $-CH_2-(CH_2-O-CH_2)_3-CH_2-$ | NH | — | — | Spacer system; $(CH_2)_5$ | Large, charged or hydrophobic compound; toxin; auristatin; MMAF |
| $(CH_2)_5$ | NH | $-(C=O)-CH_2-$ | — | Spacer system; $(CH_2)_5$ | Large, charged or hydrophobic compound; toxin; auristatin; MMAF |
| $(CH_2)_5$ | NH | $-(C=O)-(CH_2)_5-$ | — | Spacer system; $(CH_2)_5$ | Large, charged or hydrophobic compound; toxin; auristatin; MMAF |
| $(CH_2)_5$ | NH | $-CH_2-(CH_2-O-CH_2)_{1-24}-CH_2-$ | — | Spacer system; $(CH_2)_5$ | Large, charged or hydrophobic compound; toxin; auristatin; MMAF |
| $-O-(CH_2)_{1-5}$ | NH | $-CH_2-(CH_2-O-CH_2)_{1-24}-CH_2-$ | — | Spacer system; $(CH_2)_5$ | Large, charged or hydrophobic compound; toxin; auristatin; MMAF |
| $-O-CH_2-(CH_2-O-CH_2)_3-CH_2-$ | NH | $-(C=O)-CH_2-$ | — | Spacer system; $(CH_2)_5$ | Large, charged or hydrophobic compound; toxin; auristatin; MMAF |
| $-O-CH_2-(CH_2-O-CH_2)_3-CH_2-$ | NH | $-(C=O)-(CH_2)_5-$ | — | Spacer system; $(CH_2)_5$ | Large, charged or hydrophobic compound; toxin; auristatin; MMAF |
| $-O-CH_2-(CH_2-O-CH_2)_3-CH_2-$ | NH | $-CH_2-(CH_2-O-CH_2)_{1-24}-CH_2-$ | — | Spacer system; $(CH_2)_5$ | Large, charged or hydrophobic compound; toxin; auristatin; MMAF |
| $-CH_2-(CH_2-O-CH_2)_3-CH_2-$ | NH | $-CH_2-(CH_2-O-CH_2)_{1-24}-CH_2-$ | — | Spacer system; $(CH_2)_5$ | Large, charged or hydrophobic compound; toxin; auristatin; MMAF |
| $(CH_2)_5$ | NH | — | Non-cleavable linker; $(CH_2)_5$ | — | Large, charged or hydrophobic compound; toxin; auristatin; MMAF |
| $(CH_2)_{6-10}$ | NH | — | Non-cleavable linker; $(CH_2)_5$ | — | Large, charged or hydrophobic compound; toxin; auristatin; MMAF |

TABLE 2-continued

| $(C)_n$ | X | L | V | Y | Z |
|---|---|---|---|---|---|
| $(CH_2)_{15}$ | NH | — | Non-cleavable linker; $(CH_2)_5$ | — | Large, charged or hydrophobic compound; toxin; auristatin; MMAF |
| $—CH_2—(CH_2—O—CH_2)_3—CH_2—$ | NH | — | Non-cleavable linker; $(CH_2)_5$ | — | Large, charged or hydrophobic compound; toxin; auristatin; MMAF |
| $(CH_2)_5$ | NH | $—(C=O)—CH_2—$ | Non-cleavable linker; $(CH_2)_5$ | — | Large, charged or hydrophobic compound; toxin; auristatin; MMAF |
| $(CH_2)_5$ | NH | $—(C=O)—(CH_2)_5—$ | Non-cleavable linker; $(CH_2)_5$ | — | Large, charged or hydrophobic compound; toxin; auristatin; MMAF |
| $(CH_2)_5$ | NH | $—(C=O)—(CH_2)_5—$ | Non-cleavable linker; $(CH_2)_5$ | — | Large, charged or hydrophobic compound; toxin; auristatin; MMAF |
| $(CH_2)_5$ | NH | $—(C=O)—(CH_2)_5—$ | Non-cleavable linker; $(CH_2)_5$ | — | Large, charged or hydrophobic compound; toxin; auristatin; MMAF |
| $(CH_2)_5$ | NH | $—CH_2—(CH_2—O—CH_2)_{1-24}—CH_2—$ | Non-cleavable linker; $(CH_2)_5$ | — | Large, charged or hydrophobic compound; toxin; auristatin; MMAF |
| $—O—(CH_2)_{1-5}—$ | NH | $—CH_2—(CH_2—O—CH_2)_{1-24}—CH_2—$ | Non-cleavable linker; $(CH_2)_5$ | — | Large, charged or hydrophobic compound; toxin; auristatin; MMAF |
| $—O—CH_2—(CH_2—O—CH_2)_3—CH_2—$ | NH | $—CH_2—(CH_2—O—CH_2)_{1-24}—CH_2—$ | Non-cleavable linker; $(CH_2)_5$ | — | Large, charged or hydrophobic compound; toxin; auristatin; MMAF |
| $—O—CH_2—(CH_2—O—CH_2)_3—CH_2—$ | NH | $—(C=O)—CH_2—$ | Non-cleavable linker; $(CH_2)_5$ | — | Large, charged or hydrophobic compound; toxin; auristatin; MMAF |
| $—O—CH_2—(CH_2—O—CH_2)_3—CH_2—$ | NH | $—(C=O)—(CH_2)_5—$ | Non-cleavable linker; $(CH_2)_5$ | — | Large, charged or hydrophobic compound; toxin; auristatin; MMAF |
| $—CH_2—(CH_2—O—CH_2)_3—CH_2—$ | NH | $—(C=O)—(CH_2)_1-24—CH_2—$ | Non-cleavable linker; $(CH_2)_5$ | — | Large, charged or hydrophobic compound; toxin; auristatin; MMAF |
| $(CH_2)_5$ | O | $—(C=O)—CH_2—$ | — | Spacer system | Charged compound |
| $(CH_2)_5$ | O | $—(C=O)—(CH_2)_5—$ | — | Spacer system | Large, charged or hydrophobic compound; toxin; auristatin; MMAE |
| $(CH_2)_5$ | O | $—(C=O)—(CH_2)_5—$ | Cleavable or non-cleavable linker; di- or tri- or oligo peptide; val-cit | Spacer system | Large, charged or hydrophobic compound; toxin; auristatin; MMAE |
| $(CH_2)_5$ | O | $—(C=O)—(CH_2)_5—$ | Cleavable or non-cleavable linker; di- or tri- or oligo peptide; val-cit; or absent | Spacer system | Large, charged or hydrophobic compound; toxin; auristatin; MMAE |
| $(CH_2)_{10}$ | O | $—(C=O)—(CH_2)_5—$ | Cleavable or non-cleavable linker; di- or tri- or oligo peptide; val-cit; or absent | Spacer system | Large, charged or hydrophobic compound; toxin; auristatin; MMAE |
| $(CH_2)_{15}$ | O | $—(C=O)—(CH_2)_5—$ | Cleavable or non-cleavable linker; di- or tri- or oligo | Spacer system | Large, charged or hydrophobic compound; |

TABLE 2-continued

| $(C)_n$ | X | L | V | Y | Z |
|---|---|---|---|---|---|
| $(CH_2)_5$ | O | $-CH_2-(CH_2-O-CH_2)_4-CH_2-$ | Cleavable or non-cleavable linker; di- or tri- or oligo peptide; val-cit; or absent | Spacer system | Large, charged or hydrophobic compound; toxin; auristatin; MMAE |
| $(CH_2)_5$ | O | $-CH_2-(CH_2-O-CH_2)_{12}-CH_2-$ | Cleavable or non-cleavable linker; di- or tri- or oligo peptide; val-cit; or absent | Spacer system | Large, charged or hydrophobic compound; toxin; auristatin; MMAE |
| $(CH_2)_5$ | O | $-CH_2-(CH_2-O-CH_2)_{1-24}-CH_2-$ | Cleavable or non-cleavable linker; di- or tri- or oligo peptide; val-cit; or absent | Spacer system | Large, charged or hydrophobic compound; toxin; auristatin; MMAE |
| $(CH_2)_{10}$ | O | $-CH_2-(CH_2-O-CH_2)_4-CH_2-$ | Cleavable or non-cleavable linker; di- or tri- or oligo peptide; val-cit; or absent | Spacer system | Large, charged or hydrophobic compound; toxin; auristatin; MMAE |
| $(CH_2)_{15}$ | O | $-CH_2-(CH_2-O-CH_2)_4-CH_2-$ | Cleavable or non-cleavable linker; di- or tri- or oligo peptide; val-cit; or absent | Spacer system | Large, charged or hydrophobic compound; toxin; auristatin; MMAE |
| $(CH_2)_5$ | O | $-(C=O)-CH_2-(CH_2-O-CH_2)_4-CH_2-$ | Cleavable or non-cleavable linker; di- or tri- or oligo peptide; val-cit; or absent | Spacer system | Large, charged or hydrophobic compound; toxin; auristatin; MMAE |
| $(CH_2)_{10}$ | O | $-(C=O)-CH_2-(CH_2-O-CH_2)_{1-24}-CH_2-$ | Cleavable or non-cleavable linker; di- or tri- or oligo peptide; val-cit; or absent | Spacer system | Large, charged or hydrophobic compound; toxin; auristatin; MMAE |
| $(CH_2)_{15}$ | O | $-(C=O)-CH_2-(CH_2-O-CH_2)_{1-24}-CH_2-$ | Cleavable or non-cleavable linker; di- or tri- or oligo peptide; val-cit; or absent | Spacer system | Large, charged or hydrophobic compound; toxin; auristatin; MMAE |
| $(CH_2)_5$ | O | $-(C=O)-(CH_2)_{10-20}-$ | Cleavable or non-cleavable linker; di- or tri- or oligo peptide; val-cit; or absent | Spacer system | Large, charged or hydrophobic compound; toxin; auristatin; MMAE |
| $(CH_2)_{10}$ | O | $-(C=O)-(CH_2)_{10-20}-$ | Cleavable or non-cleavable linker; di- or tri- or oligo peptide; val-cit; or absent | Spacer system | Large, charged or hydrophobic compound; toxin; auristatin; MMAE |
| $(CH_2)_{15}$ | O | $-(C=O)-(CH_2)_{10-20}-$ | Cleavable or non-cleavable linker; di- or tri- or oligo peptide; val-cit; or absent | Spacer system | Large, charged or hydrophobic compound; toxin; auristatin; MMAE |
| $(CH_2)_5$ | O | $-(CH_2)_{1-6}-$ | Cleavable or non-cleavable linker; di- or tri- or oligo peptide; val-cit; or absent | Spacer system | Large, charged or hydrophobic compound; toxin; auristatin; MMAE |
| $(CH_2)_{10}$ | O | $-(CH_2)_{1-6}-$ | Cleavable or non-cleavable linker; di- or tri- or oligo peptide; val-cit; or absent | Spacer system | Large, charged or hydrophobic compound; toxin; auristatin; MMAE |
| $(CH_2)_{15}$ | O | $-(CH_2)_{1-6}-$ | Cleavable or non-cleavable linker; di- or tri- or oligo peptide; val-cit; or absent | Spacer system | Large, charged or hydrophobic compound; toxin; auristatin; MMAE |
| $(CH_2)_5$ | O | $-(CH_2)_{10-20}-$ | Cleavable or non-cleavable linker; di- or tri- or oligo peptide; val-cit; or absent | Spacer system | Large, charged or hydrophobic compound; toxin; auristatin; MMAE |
| $(CH_2)_{10}$ | O | $-(CH_2)_{10-20}-$ | Cleavable or non-cleavable linker; di- or tri- or oligo peptide; val-cit; or absent | Spacer system | Large, charged or hydrophobic compound; toxin; auristatin; MMAE |
| $(CH_2)_{15}$ | O | $-(CH_2)_{10-20}-$ | Cleavable or non-cleavable linker; di- or tri- or oligo peptide; val-cit; or absent | Spacer system | Large, charged or hydrophobic compound; toxin; auristatin; MMAE |

TABLE 2-continued

| C$_n$ | X | L | V | Y | Z |
|---|---|---|---|---|---|
| (CH$_2$)$_5$ | O | —(C=O)—O—CH$_2$— | Cleavable or non-cleavable linker; di- or tri- or oligo peptide; val-cit; or absent | Spacer system | Large, charged or hydrophobic compound; toxin; auristatin; MMAE |
| (CH$_2$)$_{10}$ | O | —(C=O)—O—CH$_2$— | Cleavable or non-cleavable linker; di- or tri- or oligo peptide; val-cit; or absent | Spacer system | Large, charged or hydrophobic compound; toxin; auristatin; MMAE |
| (CH$_2$)$_{15}$ | O | —(C=O)—O—CH$_2$— | Cleavable or non-cleavable linker; di- or tri- or oligo peptide; val-cit; or absent | Spacer system | Large, charged or hydrophobic compound; toxin; auristatin; MMAE |
| (CH$_2$)$_5$ | O | —(C=O)—O—(CH$_2$)$_{2-20}$— | Cleavable or non-cleavable linker; di- or tri- or oligo peptide; val-cit; or absent | Spacer system | Large, charged or hydrophobic compound; toxin; auristatin; MMAE |
| (CH$_2$)$_{10}$ | O | —(C=O)—O—(CH$_2$)$_{2-20}$— | Cleavable or non-cleavable linker; di- or tri- or oligo peptide; val-cit; or absent | Spacer system | Large, charged or hydrophobic compound; toxin; auristatin; MMAE |
| (CH$_2$)$_{15}$ | O | —(C=O)—O—(CH$_2$)$_{2-20}$— | Cleavable or non-cleavable linker; di- or tri- or oligo peptide; val-cit; or absent | Spacer system | Large, charged or hydrophobic compound; toxin; auristatin; MMAE |
| (CH$_2$)$_5$ | O | Amino acid, di- or tri- or oligo peptide | Cleavable or non-cleavable linker; di- or tri- or oligo peptide; val-cit; or absent | Spacer system | Large, charged or hydrophobic compound; toxin; auristatin; MMAE |
| (CH$_2$)$_{10}$ | O | Amino acid, di- or tri- or oligo peptide | Cleavable or non-cleavable linker; di- or tri- or oligo peptide; val-cit; or absent | Spacer system | Large, charged or hydrophobic compound; toxin; auristatin; MMAE |
| (CH$_2$)$_{15}$ | O | Amino acid, di- or tri- or oligo peptide | Cleavable or non-cleavable linker; di- or tri- or oligo peptide; val-cit; or absent | Spacer system | Large, charged or hydrophobic compound; toxin; auristatin; MMAE |
| (CH$_2$)$_5$ | O | —(C=O)—CH$_2$—S— (succinimide) | Cleavable or non-cleavable linker; di- or tri- or oligo peptide; val-cit; or absent | Spacer system; CH$_2$—(CH$_2$—O—CH$_2$)$_4$—CH$_2$— | Large, charged or hydrophobic compound; toxin; auristatin; MMAE |
| (CH$_2$)$_5$ | O | —(C=O)—CH$_5$—S— (succinimide) | Cleavable or non-cleavable linker; di- or tri- or oligo peptide; val-cit; or absent | Spacer system; CH$_2$—(CH$_2$—O—CH$_2$)$_4$—CH$_2$— | Large, charged or hydrophobic compound; toxin; auristatin; MMAE |

TABLE 2-continued

| $(C)_h$ | X | L | V | Y | Z |
|---|---|---|---|---|---|
| $(CH_2)_5$ | O | —CH$_2$—(CH$_2$—O—CH$_2$)$_{1-24}$—CH$_2$—S—[succinimide]—* | Cleavable or non-cleavable linker; di- or tri- or oligo peptide; val-cit; or absent | Spacer system; CH$_2$—(CH$_2$—O—CH$_2$)$_4$—CH$_2$— | Large, charged or hydrophobic compound; toxin; auristatin; MMAE |
| —CH$_2$—(CH$_2$—O—CH$_2$)$_3$—CH$_2$— | O | — | Cleavable or non-cleavable linker; di- or tri- or oligo peptide; val-cit; or absent | Spacer system | Large, charged or hydrophobic compound; toxin; auristatin; MMAE |
| —CH$_2$—(CH$_2$—O—CH$_2$)$_3$—CH$_2$— | O | —CH$_2$—(CH$_2$—O—CH$_2$)$_{1-24}$—CH$_2$— | Cleavable or non-cleavable linker; di- or tri- or oligo peptide; val-cit; or absent | Spacer system | Large, charged or hydrophobic compound; toxin; auristatin; MMAE |
| —CH$_2$—(CH$_2$—O—CH$_2$)$_3$—CH$_2$— | O | —(C=O)—CH$_2$—(CH$_2$—O—CH$_2$)$_{1-24}$—CH$_2$— | Cleavable or non-cleavable linker; di- or tri- or oligo peptide; val-cit; or absent | Spacer system | Large, charged or hydrophobic compound; toxin; auristatin; MMAE |
| —O—(CH$_2$)$_{1-5}$ | O | — | Cleavable or non-cleavable linker; di- or tri- or oligo peptide; val-cit; or absent | Spacer system | Large, charged or hydrophobic compound; toxin; auristatin; MMAE |
| —O—CH$_2$—(CH$_2$—O—CH$_2$)$_3$—CH$_2$— | O | —CH$_2$—(CH$_2$—O—CH$_2$)$_{1-24}$—CH$_2$— | Cleavable or non-cleavable linker; di- or tri- or oligo peptide; val-cit; or absent | Spacer system | Large, charged or hydrophobic compound; toxin; auristatin; MMAE |
| —O—CH$_2$—(CH$_2$—O—CH$_2$)$_3$—CH$_2$— | O | —(C=O)—CH$_2$—(CH$_2$—O—CH$_2$)$_{1-24}$—CH$_2$— | Cleavable or non-cleavable linker; di- or tri- or oligo peptide; val-cit; or absent | Spacer system | Large, charged or hydrophobic compound; toxin; auristatin; MMAE |
| —(CH$_2$)$_4$—CH(NH$_2$)—(C=O)— | O | — | di- or tri- or oligo peptide; val-cit | Spacer system | Charged compound |
| —(CH$_2$)$_4$—CH(NH$_2$)—(C=O)— | O | — | Cleavable or non-cleavable linker; di- or tri- or oligo peptide; val-cit; or absent | Spacer system | Large, charged or hydrophobic compound; toxin; auristatin; MMAE |
| —(CH$_2$)$_4$—CH(NH$_2$)—(C=O)— | O | —(CH$_2$)$_{1-6}$— | Cleavable or non-cleavable linker; di- or tri- or oligo peptide; val-cit; or absent | Spacer system | Large, charged or hydrophobic compound; toxin; auristatin; MMAE |
| —(CH$_2$)$_4$—CH(NH$_2$)—(C=O)— | O | —(CH$_2$)$_5$— | Cleavable or non-cleavable linker; di- or tri- or oligo peptide; val-cit; or absent | Spacer system | Large, charged or hydrophobic compound; toxin; auristatin; MMAE |
| —(CH$_2$)$_4$—CH(NH$_2$)—(C=O)— | O | —CH$_2$—(CH$_2$—O—CH$_2$)$_{1-24}$—CH$_2$— | Cleavable or non-cleavable linker; di- or tri- or oligo peptide; val-cit; or absent | Spacer system | Large, charged or hydrophobic compound; toxin; auristatin; MMAE |
| (CH$_2$)$_5$ | O | — | — | Spacer system; (CH$_2$)$_5$ | Large, charged or hydrophobic compound; toxin; auristatin; MMAE |
| (CH$_2$)$_{6-10}$ | O | — | — | Spacer system; (CH$_2$)$_5$ | Large, charged or hydrophobic compound; toxin; auristatin; MMAF |
| (CH$_2$)$_{15}$ | O | — | — | Spacer system; (CH$_2$)$_5$ | Large, charged or hydrophobic compound; |

TABLE 2-continued

| $C_h$ | X | L | V | Y | Z |
|---|---|---|---|---|---|
| —CH$_2$—(CH$_2$—O—CH$_2$)$_3$—CH$_2$— | O | — | — | Spacer system; (CH$_2$)$_5$ | Large, charged or hydrophobic compound; toxin; auristatin; MMAF |
| (CH$_2$)$_5$ | O | —(C=O)—CH$_2$— | — | Spacer system; (CH$_2$)$_5$ | Large, charged or hydrophobic compound; toxin; auristatin; MMAF |
| (CH$_2$)$_5$ | O | —(C=O)—(CH$_2$)$_5$— | — | Spacer system; (CH$_2$)$_5$ | Large, charged or hydrophobic compound; toxin; auristatin; MMAF |
| (CH$_2$)$_5$ | O | —CH$_2$—(CH$_2$—O—CH$_2$)$_{1-24}$—CH$_2$— | — | Spacer system; (CH$_2$)$_5$ | Large, charged or hydrophobic compound; toxin; auristatin; MMAF |
| —O—(CH$_2$)$_{1-5}$ | O | —CH$_2$—(CH$_2$—O—CH$_2$)$_{1-24}$—CH$_2$— | — | Spacer system; (CH$_2$)$_5$ | Large, charged or hydrophobic compound; toxin; auristatin; MMAF |
| —O—CH$_2$—(CH$_2$—O—CH$_2$)$_3$—CH$_2$— | O | —CH$_2$—(CH$_2$—O—CH$_2$)$_{1-24}$—CH$_2$— | — | Spacer system; (CH$_2$)$_5$ | Large, charged or hydrophobic compound; toxin; auristatin; MMAF |
| —O—CH$_2$—(CH$_2$—O—CH$_2$)$_3$—CH$_2$— | O | —(C=O)—CH$_2$— | — | Spacer system; (CH$_2$)$_5$ | Large, charged or hydrophobic compound; toxin; auristatin; MMAF |
| —O—CH$_2$—(CH$_2$—O—CH$_2$)$_3$—CH$_2$— | O | —(C=O)—(CH$_2$)$_5$— | — | Spacer system; (CH$_2$)$_5$ | Large, charged or hydrophobic compound; toxin; auristatin; MMAF |
| —CH$_2$—(CH$_2$—O—CH$_2$)$_3$—CH$_2$— | O | —CH$_2$—(CH$_2$—O—CH$_2$)$_{1-24}$—CH$_2$— | — | Spacer system; (CH$_2$)$_5$ | Large, charged or hydrophobic compound; toxin; auristatin; MMAF |
| (CH$_2$)$_5$ | O | — | Non-cleavable linker; (CH$_2$)$_5$ | — | Large, charged or hydrophobic compound; toxin; auristatin; MMAF |
| (CH$_2$)$_{6-10}$ | O | — | Non-cleavable linker; (CH$_2$)$_5$ | — | Large, charged or hydrophobic compound; toxin; auristatin; MMAF |
| (CH$_2$)$_{15}$ | O | — | Non-cleavable linker; (CH$_2$)$_5$ | — | Large, charged or hydrophobic compound; toxin; auristatin; MMAF |
| —CH$_2$—(CH$_2$—O—CH$_2$)$_3$—CH$_2$— | O | — | Non-cleavable linker; (CH$_2$)$_5$ | — | Large, charged or hydrophobic compound; toxin; auristatin; MMAF |
| (CH$_2$)$_5$ | O | —(C=O)—CH$_2$— | Non-cleavable linker; (CH$_2$)$_5$ | — | Large, charged or hydrophobic compound; toxin; auristatin; MMAF |
| (CH$_2$)$_5$ | O | —(C=O)—(CH$_2$)$_5$— | Non-cleavable linker; (CH$_2$)$_5$ | — | Large, charged or hydrophobic compound; toxin; auristatin; MMAF |
| (CH$_2$)$_5$ | O | —(C=O)—(CH$_2$)$_5$— | Non-cleavable linker; (CH$_2$)$_5$ | — | Large, charged or hydrophobic compound; toxin; auristatin; MMAF |
| (CH$_2$)$_5$ | O | —(C=O)—(CH$_2$)$_5$— | Non-cleavable linker; (CH$_2$)$_5$ | — | Large, charged or hydrophobic compound; toxin; auristatin; MMAF |

TABLE 2-continued

| $(C)_n$ | X | L | V | Y | Z |
|---|---|---|---|---|---|
| $(CH_2)_5$ | O | $-CH_2-(CH_2-O-CH_2)_{1-24}-CH_2-$ | Non-cleavable linker; $(CH_2)_5$ | — | toxin; auristatin; MMAF |
| $-O-(CH_2)_{1-5}$ | O | $-CH_2-(CH_2-O-CH_2)_{1-24}-CH_2-$ | Non-cleavable linker; $(CH_2)_5$ | — | Large, charged or hydrophobic compound; toxin; auristatin; MMAF |
| $-O-CH_2-(CH_2-O-CH_2)_3-CH_2-$ | O | $-CH_2-(CH_2-O-CH_2)_{1-24}-CH_2-$ | Non-cleavable linker; $(CH_2)_5$ | — | Large, charged or hydrophobic compound; toxin; auristatin; MMAF |
| $-O-CH_2-(CH_2-O-CH_2)_3-CH_2-$ | O | $-(C=O)-CH_2-$ | Non-cleavable linker; $(CH_2)_5$ | — | Large, charged or hydrophobic compound; toxin; auristatin; MMAF |
| $-O-CH_2-(CH_2-O-CH_2)_3-CH_2-$ | O | $-(C=O)-(CH_2)_5-$ | Non-cleavable linker; $(CH_2)_5$ | — | Large, charged or hydrophobic compound; toxin; auristatin; MMAF |
| $-CH_2-(CH_2-O-CH_2)_3-CH_2-$ | O | $-CH_2-(CH_2-O-CH_2)_{1-24}-CH_2-$ | Non-cleavable linker; $(CH_2)_5$ | — | Large, charged or hydrophobic compound; toxin; auristatin; MMAF |
| $(CH_2)_5$ | S | $-(C=O)-CH_2-$ | — | Spacer system | Charged compound |
| $(CH_2)_5$ | S | $-(C=O)-(CH_2)_5-$ | — | | |
| $(CH_2)_5$ | S | $-(C=O)-(CH_2)_5-$ | Cleavable or non-cleavable linker; di- or tri- or oligo peptide; val-cit | Spacer system | Large, charged or hydrophobic compound; toxin; auristatin; MMAE |
| $(CH_2)_5$ | S | $-(C=O)-(CH_2)_5-$ | Cleavable or non-cleavable linker; di- or tri- or oligo peptide; val-cit; or absent | Spacer system | Large, charged or hydrophobic compound; toxin; auristatin; MMAE |
| $(CH_2)_{10}$ | S | $-(C=O)-(CH_2)_5-$ | Cleavable or non-cleavable linker; di- or tri- or oligo peptide; val-cit; or absent | Spacer system | Large, charged or hydrophobic compound; toxin; auristatin; MMAE |
| $(CH_2)_{15}$ | S | $-(C=O)-(CH_2)_5-$ | Cleavable or non-cleavable linker; di- or tri- or oligo peptide; val-cit; or absent | Spacer system | Large, charged or hydrophobic compound; toxin; auristatin; MMAE |
| $(CH_2)_5$ | S | $-CH_2-(CH_2-O-CH_2)_4-CH_2-$ | Cleavable or non-cleavable linker; di- or tri- or oligo peptide; val-cit; or absent | Spacer system | Large, charged or hydrophobic compound; toxin; auristatin; MMAE |
| $(CH_2)_5$ | S | $-CH_2-(CH_2-O-CH_2)_{12}-CH_2-$ | Cleavable or non-cleavable linker; di- or tri- or oligo peptide; val-cit; or absent | Spacer system | Large, charged or hydrophobic compound; toxin; auristatin; MMAE |
| $(CH_2)_5$ | S | $-CH_2-(CH_2-O-CH_2)_{1-24}-CH_2-$ | Cleavable or non-cleavable linker; di- or tri- or oligo peptide; val-cit; or absent | Spacer system | Large, charged or hydrophobic compound; toxin; auristatin; MMAE |
| $(CH_2)_5$ | S | $-CH_2-(CH_2-O-CH_2)_4-CH_2-$ | Cleavable or non-cleavable linker; di- or tri- or oligo peptide; val-cit; or absent | Spacer system | Large, charged or hydrophobic compound; toxin; auristatin; MMAE |
| $(CH_2)_{10}$ | S | $-CH_2-(CH_2-O-CH_2)_4-CH_2-$ | Cleavable or non-cleavable linker; di- or tri- or oligo peptide; val-cit; or absent | Spacer system | Large, charged or hydrophobic compound; toxin; auristatin; MMAE |
| $(CH_2)_{15}$ | S | $-CH_2-(CH_2-O-CH_2)_4-CH_2-$ | Cleavable or non-cleavable linker; di- or tri- or oligo peptide; val-cit; or absent | Spacer system | Large, charged or hydrophobic compound; toxin; auristatin; MMAE |
| $(CH_2)_5$ | S | $-(C=O)-CH_2-(CH_2-O-CH_2)_4-CH_2-$ | Cleavable or non-cleavable | Spacer system | Large, charged or |

TABLE 2-continued

| $C_n$ | X | L | V | Y | Z |
|---|---|---|---|---|---|
| $(CH_2)_{10}$ | S | $-(C=O)-CH_2-(CH_2-O-CH_2)_{1-24}-CH_2-$ | Cleavable or non-cleavable linker; di- or tri- or oligo peptide; val-cit; or absent | Spacer system | Large, charged or hydrophobic compound; toxin; auristatin; MMAE |
| $(CH_2)_{15}$ | S | $-(C=O)-CH_2-(CH_2-O-CH_2)_{1-24}-CH_2-$ | Cleavable or non-cleavable linker; di- or tri- or oligo peptide; val-cit; or absent | Spacer system | Large, charged or hydrophobic compound; toxin; auristatin; MMAE |
| $(CH_2)_5$ | S | $-(C=O)-(CH_2)_{10-20}-$ | Cleavable or non-cleavable linker; di- or tri- or oligo peptide; val-cit; or absent | Spacer system | Large, charged or hydrophobic compound; toxin; auristatin; MMAE |
| $(CH_2)_{10}$ | S | $-(C=O)-(CH_2)_{10-20}-$ | Cleavable or non-cleavable linker; di- or tri- or oligo peptide; val-cit; or absent | Spacer system | Large, charged or hydrophobic compound; toxin; auristatin; MMAE |
| $(CH_2)_{15}$ | S | $-(C=O)-(CH_2)_{10-20}-$ | Cleavable or non-cleavable linker; di- or tri- or oligo peptide; val-cit; or absent | Spacer system | Large, charged or hydrophobic compound; toxin; auristatin; MMAE |
| $(CH_2)_5$ | S | $-(CH_2)_{1-6}-$ | Cleavable or non-cleavable linker; di- or tri- or oligo peptide; val-cit; or absent | Spacer system | Large, charged or hydrophobic compound; toxin; auristatin; MMAE |
| $(CH_2)_{10}$ | S | $-(CH_2)_{1-6}-$ | Cleavable or non-cleavable linker; di- or tri- or oligo peptide; val-cit; or absent | Spacer system | Large, charged or hydrophobic compound; toxin; auristatin; MMAE |
| $(CH_2)_{15}$ | S | $-(CH_2)_{1-6}-$ | Cleavable or non-cleavable linker; di- or tri- or oligo peptide; val-cit; or absent | Spacer system | Large, charged or hydrophobic compound; toxin; auristatin; MMAE |
| $(CH_2)_5$ | S | $-(CH_2)_{10-20}-$ | Cleavable or non-cleavable linker; di- or tri- or oligo peptide; val-cit; or absent | Spacer system | Large, charged or hydrophobic compound; toxin; auristatin; MMAE |
| $(CH_2)_{10}$ | S | $-(CH_2)_{10-20}-$ | Cleavable or non-cleavable linker; di- or tri- or oligo peptide; val-cit; or absent | Spacer system | Large, charged or hydrophobic compound; toxin; auristatin; MMAE |
| $(CH_2)_{15}$ | S | $-(CH_2)_{10-20}-$ | Cleavable or non-cleavable linker; di- or tri- or oligo peptide; val-cit; or absent | Spacer system | Large, charged or hydrophobic compound; toxin; auristatin; MMAE |
| $(CH_2)_5$ | S | $-(C=O)-O-CH_2-$ | Cleavable or non-cleavable linker; di- or tri- or oligo peptide; val-cit; or absent | Spacer system | Large, charged or hydrophobic compound; toxin; auristatin; MMAE |
| $(CH_2)_{10}$ | S | $-(C=O)-O-CH_2-$ | Cleavable or non-cleavable linker; di- or tri- or oligo peptide; val-cit; or absent | Spacer system | Large, charged or hydrophobic compound; toxin; auristatin; MMAE |
| $(CH_2)_{15}$ | S | $-(C=O)-O-CH_2-$ | Cleavable or non-cleavable linker; di- or tri- or oligo peptide; val-cit; or absent | Spacer system | Large, charged or hydrophobic compound; toxin; auristatin; MMAE |
| $(CH_2)_5$ | S | $-(C=O)-O-(CH_2)_{2-20}-$ | Cleavable or non-cleavable linker; di- or tri- or oligo peptide; val-cit; or absent | Spacer system | Large, charged or hydrophobic compound; toxin; auristatin; MMAE |
| $(CH_2)_{10}$ | S | $-(C=O)-O-(CH_2)_{2-20}-$ | Cleavable or non-cleavable linker; di- or tri- or oligo peptide; val-cit; or absent | Spacer system | Large, charged or hydrophobic compound; toxin; auristatin; MMAE |
| $(CH_2)_{15}$ | S | $-(C=O)-O-(CH_2)_{2-20}-$ | Cleavable or non-cleavable linker; di- or tri- or oligo peptide; val-cit; or absent | Spacer system | Large, charged or hydrophobic compound; toxin; auristatin; MMAE |

TABLE 2-continued

| $C_n$ | X | L | V | Y | Z |
|---|---|---|---|---|---|
| $(CH_2)_5$ | S | Amino acid, di- or tri- or oligo peptide | Cleavable or non-cleavable linker; di- or tri- or oligo peptide; val-cit; or absent | Spacer system | Large, charged or hydrophobic compound; toxin; auristatin; MMAE |
| $(CH_2)_{10}$ | S | Amino acid, di- or tri- or oligo peptide | Cleavable or non-cleavable linker; di- or tri- or oligo peptide; val-cit; or absent | Spacer system | Large, charged or hydrophobic compound; toxin; auristatin; MMAE |
| $(CH_2)_{15}$ | S | Amino acid, di- or tri- or oligo peptide | Cleavable or non-cleavable linker; di- or tri- or oligo peptide; val-cit; or absent | Spacer system | Large, charged or hydrophobic compound; toxin; auristatin; MMAE |
| $(CH_2)_5$ | S | —(C=O)—CH$_2$—S—[succinimide] | Cleavable or non-cleavable linker; di- or tri- or oligo peptide; val-cit; or absent | Spacer system; CH$_2$—(CH$_2$—O—CH$_2$)$_4$—CH$_2$— | Large, charged or hydrophobic compound; toxin; auristatin; MMAE |
| $(CH_2)_5$ | S | —(C=O)—CH$_5$—S—[succinimide] | Cleavable or non-cleavable linker; di- or tri- or oligo peptide; val-cit; or absent | Spacer system; CH$_2$—(CH$_2$—O—CH$_2$)$_4$—CH$_2$— | Large, charged or hydrophobic compound; toxin; auristatin; MMAE |
| $(CH_2)_5$ | S | —CH$_2$—(CH$_2$—O—CH$_2$)$_{1-24}$—CH$_2$—S—[succinimide] | Cleavable or non-cleavable linker; di- or tri- or oligo peptide; val-cit; or absent | Spacer system; CH$_2$—(CH$_2$—O—CH$_2$)$_4$—CH$_2$— | Large, charged or hydrophobic compound; toxin; auristatin; MMAE |
| —CH$_2$—(CH$_2$—O—CH$_2$)$_3$—CH$_2$— | S | — | Cleavable or non-cleavable linker; di- or tri- or oligo peptide; val-cit; or absent | Spacer system | Large, charged or hydrophobic compound; toxin; auristatin; MMAE |
| —CH$_2$—(CH$_2$—O—CH$_2$)$_3$—CH$_2$— | S | —CH$_2$—(CH$_2$—O—CH$_2$)$_{1-24}$—CH$_2$— | Cleavable or non-cleavable linker; di- or tri- or oligo peptide; val-cit; or absent | Spacer system | Large, charged or hydrophobic compound; toxin; auristatin; MMAE |
| —CH$_2$—(CH$_2$—O—CH$_2$)$_3$—CH$_2$— | S | —(C=O)—CH$_2$—(CH$_2$—O—CH$_2$)$_{1-24}$—CH$_2$— | Cleavable or non-cleavable linker; di- or tri- or oligo peptide; val-cit; or absent | Spacer system | Large, charged or hydrophobic compound; toxin; auristatin; MMAE |
| —O—(CH$_2$)$_{1-5}$ | S | — | Cleavable or non-cleavable linker; di- or tri- or oligo peptide; val-cit; or absent | Spacer system | Large, charged or hydrophobic compound; toxin; auristatin; MMAE |
| —O—CH$_2$—(CH$_2$—O—CH$_2$)$_3$—CH$_2$— | S | — | Cleavable or non-cleavable linker; di- or tri- or oligo peptide; val-cit; or absent | Spacer system | Large, charged or |

TABLE 2-continued

| $C_h$ | X | L | V | Y | Z |
|---|---|---|---|---|---|
| —O—CH$_2$—(CH$_2$—O—CH$_2$)$_3$—CH$_2$— | S | —CH$_2$—(CH$_2$—O—CH$_2$)$_{1-24}$—CH$_2$— | Cleavable or non-cleavable linker; di- or tri- or oligo peptide; val-cit; or absent | Spacer system | Large, charged or hydrophobic compound; toxin; auristatin; MMAE |
| —O—CH$_2$—(CH$_2$—O—CH$_2$)$_3$—CH$_2$— | S | —(C=O)—CH$_2$—(CH$_2$—O—CH$_2$)$_{1-24}$—CH$_2$— | Cleavable or non-cleavable linker; di- or tri- or oligo peptide; val-cit; or absent | Spacer system | Large, charged or hydrophobic compound; toxin; auristatin; MMAE |
| (CH$_2$)$_4$—CH(NH$_2$)—(C=O)— | S | — | | | Charged compound |
| (CH$_2$)$_4$—CH(NH$_2$)—(C=O)— | S | — | di- or tri- or oligo peptide; val-cit | | Large, charged or hydrophobic compound; toxin; auristatin; MMAE |
| (CH$_2$)$_4$—CH(NH$_2$)—(C=O)— | S | —(CH$_2$)$_{1-6}$— | Cleavable or non-cleavable linker; di- or tri- or oligo peptide; val-cit; or absent | Spacer system | Large, charged or hydrophobic compound; toxin; auristatin; MMAE |
| (CH$_2$)$_4$—CH(NH$_2$)—(C=O)— | S | —(CH$_2$)$_5$— | Cleavable or non-cleavable linker; di- or tri- or oligo peptide; val-cit; or absent | Spacer system | Large, charged or hydrophobic compound; toxin; auristatin; MMAE |
| (CH$_2$)$_4$—CH(NH$_2$)—(C=O)— | S | —CH$_2$—(CH$_2$—O—CH$_2$)$_{1-24}$—CH$_2$— | Cleavable or non-cleavable linker; di- or tri- or oligo peptide; val-cit; or absent | Spacer system | Large, charged or hydrophobic compound; toxin; auristatin; MMAE |
| (CH$_2$)$_5$ | S | — | — | Spacer system; (CH$_2$)$_5$ | Large, charged or hydrophobic compound; toxin; auristatin; MMAF |
| (CH$_2$)$_{6-10}$ | S | — | — | Spacer system; (CH$_2$)$_5$ | Large, charged or hydrophobic compound; toxin; auristatin; MMAF |
| (CH$_2$)$_{15}$ | S | — | — | Spacer system; (CH$_2$)$_5$ | Large, charged or hydrophobic compound; toxin; auristatin; MMAF |
| —CH$_2$—(CH$_2$—O—CH$_2$)$_3$—CH$_2$— | S | — | — | Spacer system; (CH$_2$)$_5$ | Large, charged or hydrophobic compound; toxin; auristatin; MMAF |
| (CH$_2$)$_5$ | S | —(C=O)—CH$_2$— | — | Spacer system; (CH$_2$)$_5$ | Large, charged or hydrophobic compound; toxin; auristatin; MMAF |
| (CH$_2$)$_5$ | S | —(C=O)—(CH$_2$)$_5$— | — | Spacer system; (CH$_2$)$_5$ | Large, charged or hydrophobic compound; toxin; auristatin; MMAF |
| (CH$_2$)$_5$ | S | —CH$_2$—(CH$_2$—O—CH$_2$)$_{1-24}$—CH$_2$— | — | Spacer system; (CH$_2$)$_5$ | Large, charged or hydrophobic compound; toxin; auristatin; MMAF |
| —O—(CH$_2$)$_{1-5}$ | S | —CH$_2$—(CH$_2$—O—CH$_2$)$_{1-24}$—CH$_2$— | — | Spacer system; (CH$_2$)$_5$ | Large, charged or hydrophobic compound; toxin; auristatin; MMAF |
| —O—CH$_2$—(CH$_2$—O—CH$_2$)$_3$—CH$_2$— | S | —CH$_2$—(CH$_2$—O—CH$_2$)$_{1-24}$—CH$_2$— | — | Spacer system; (CH$_2$)$_5$ | Large, charged or hydrophobic compound; toxin; auristatin; MMAF |
| —O—CH$_2$—(CH$_2$—O—CH$_2$)$_3$—CH$_2$— | S | —(C=O)—CH$_2$— | — | Spacer system; (CH$_2$)$_5$ | Large, charged or hydrophobic compound; toxin; auristatin; MMAF |

TABLE 2-continued

| (C)$_n$ | X | L | V | Y | Z |
|---|---|---|---|---|---|
| —O—CH$_2$—(CH$_2$—O—CH$_2$)$_3$—CH$_2$— | S | —(C=O)—(CH$_2$)$_5$— | — | Spacer system; (CH$_2$)$_5$ | Large, charged or hydrophobic compound; toxin; auristatin; MMAF |
| —CH$_2$—(CH$_2$—O—CH$_2$)$_3$—CH$_2$— | S | —CH$_2$—(CH$_2$—O—CH$_2$)$_{1-24}$—CH$_2$— | — | Spacer system; (CH$_2$)$_5$ | Large, charged or hydrophobic compound; toxin; auristatin; MMAF |
| (CH$_2$)$_5$ | S | — | Non-cleavable linker; (CH$_2$)$_5$ | — | Large, charged or hydrophobic compound; toxin; auristatin; MMAF |
| (CH$_2$)$_{6-10}$ | S | — | Non-cleavable linker; (CH$_2$)$_5$ | — | Large, charged or hydrophobic compound; toxin; auristatin; MMAF |
| (CH$_2$)$_{15}$ | S | — | Non-cleavable linker; (CH$_2$)$_5$ | — | Large, charged or hydrophobic compound; toxin; auristatin; MMAF |
| —CH$_2$—(CH$_2$—O—CH$_2$)$_3$—CH$_2$— | S | — | Non-cleavable linker; (CH$_2$)$_5$ | — | Large, charged or hydrophobic compound; toxin; auristatin; MMAF |
| (CH$_2$)$_5$ | S | —(C=O)—CH$_2$— | Non-cleavable linker; (CH$_2$)$_5$ | — | Large, charged or hydrophobic compound; toxin; auristatin; MMAF |
| (CH$_2$)$_5$ | S | —(C=O)—(CH$_2$)$_5$— | Non-cleavable linker; (CH$_2$)$_5$ | — | Large, charged or hydrophobic compound; toxin; auristatin; MMAF |
| (CH$_2$)$_5$ | S | —(C=O)—(CH$_2$)$_5$— | Non-cleavable linker; (CH$_2$)$_5$ | — | Large, charged or hydrophobic compound; toxin; auristatin; MMAF |
| (CH$_2$)$_5$ | S | —(C=O)—(CH$_2$)$_5$— | Non-cleavable linker; (CH$_2$)$_5$ | — | Large, charged or hydrophobic compound; toxin; auristatin; MMAF |
| (CH$_2$)$_5$ | S | —CH$_2$—(CH$_2$—O—CH$_2$)$_{1-24}$—CH$_2$— | Non-cleavable linker; (CH$_2$)$_5$ | — | Large, charged or hydrophobic compound; toxin; auristatin; MMAF |
| —O—(CH$_2$)$_{1-5}$ | S | —CH$_2$—(CH$_2$—O—CH$_2$)$_{1-24}$—CH$_2$— | Non-cleavable linker; (CH$_2$)$_5$ | — | Large, charged or hydrophobic compound; toxin; auristatin; MMAF |
| —O—CH$_2$—(CH$_2$—O—CH$_2$)$_3$—CH$_2$— | S | —CH$_2$—(CH$_2$—O—CH$_2$)$_{1-24}$—CH$_2$— | Non-cleavable linker; (CH$_2$)$_5$ | — | Large, charged or hydrophobic compound; toxin; auristatin; MMAF |
| —O—CH$_2$—(CH$_2$—O—CH$_2$)$_3$—CH$_2$— | S | —(C=O)—CH$_2$— | Non-cleavable linker; (CH$_2$)$_5$ | — | Large, charged or hydrophobic compound; toxin; auristatin; MMAF |
| —O—CH$_2$—(CH$_2$—O—CH$_2$)$_3$—CH$_2$— | S | —(C=O)—(CH$_2$)$_5$— | Non-cleavable linker; (CH$_2$)$_5$ | — | Large, charged or hydrophobic compound; toxin; auristatin; MMAF |
| —CH$_2$—(CH$_2$—O—CH$_2$)$_3$—CH$_2$— | S | —CH$_2$—(CH$_2$—O—CH$_2$)$_{1-24}$—CH$_2$— | Non-cleavable linker; (CH$_2$)$_5$ | — | Large, charged or hydrophobic compound; toxin; auristatin; MMAF |
| (CH$_2$)$_5$ | — | —(C=O)—CH$_2$— | — | — | Charged compound |
| (CH$_2$)$_5$ | — | —(C=O)—(CH$_2$)$_5$— | — | Spacer system | Large, charged or hydrophobic compound; |

TABLE 2-continued

| $(C)_n$ | X | L | V | Y | Z |
|---|---|---|---|---|---|
| $(CH_2)_5$ | — | —(C=O)—$(CH_2)_5$— | Cleavable or non-cleavable linker; di- or tri- or oligo peptide; val-cit | Spacer system | toxin; auristatin; MMAE |
| $(CH_2)_5$ | — | —(C=O)—$(CH_2)_5$— | Cleavable or non-cleavable linker; di- or tri- or oligo peptide; val-cit; or absent | Spacer system | Large, charged or hydrophobic compound; toxin; auristatin; MMAE |
| $(CH_2)_{10}$ | — | —(C=O)—$(CH_2)_5$— | Cleavable or non-cleavable linker; di- or tri- or oligo peptide; val-cit; or absent | Spacer system | Large, charged or hydrophobic compound; toxin; auristatin; MMAE |
| $(CH_2)_{15}$ | — | —(C=O)—$(CH_2)_5$— | Cleavable or non-cleavable linker; di- or tri- or oligo peptide; val-cit; or absent | Spacer system | Large, charged or hydrophobic compound; toxin; auristatin; MMAE |
| $(CH_2)_5$ | — | —$CH_2$—$(CH_2$—O—$CH_2)_4$—$CH_2$— | Cleavable or non-cleavable linker; di- or tri- or oligo peptide; val-cit; or absent | Spacer system | Large, charged or hydrophobic compound; toxin; auristatin; MMAE |
| $(CH_2)_5$ | — | —$CH_2$—$(CH_2$—O—$CH_2)_{12}$—$CH_2$— | Cleavable or non-cleavable linker; di- or tri- or oligo peptide; val-cit; or absent | Spacer system | Large, charged or hydrophobic compound; toxin; auristatin; MMAE |
| $(CH_2)_5$ | — | —$CH_2$—$(CH_2$—O—$CH_2)_{1-24}$—$CH_2$— | Cleavable or non-cleavable linker; di- or tri- or oligo peptide; val-cit; or absent | Spacer system | Large, charged or hydrophobic compound; toxin; auristatin; MMAE |
| $(CH_2)_{10}$ | — | —$CH_2$—$(CH_2$—O—$CH_2)_4$—$CH_2$— | Cleavable or non-cleavable linker; di- or tri- or oligo peptide; val-cit; or absent | Spacer system | Large, charged or hydrophobic compound; toxin; auristatin; MMAE |
| $(CH_2)_{15}$ | — | —$CH_2$—$(CH_2$—O—$CH_2)_4$—$CH_2$— | Cleavable or non-cleavable linker; di- or tri- or oligo peptide; val-cit; or absent | Spacer system | Large, charged or hydrophobic compound; toxin; auristatin; MMAE |
| $(CH_2)_5$ | — | —(C=O)—$CH_2$—$(CH_2$—O—$CH_2)_4$—$CH_2$— | Cleavable or non-cleavable linker; di- or tri- or oligo peptide; val-cit; or absent | Spacer system | Large, charged or hydrophobic compound; toxin; auristatin; MMAE |
| $(CH_2)_{10}$ | — | —(C=O)—$CH_2$—$(CH_2$—O—$CH_2)_{1-24}$—$CH_2$— | Cleavable or non-cleavable linker; di- or tri- or oligo peptide; val-cit; or absent | Spacer system | Large, charged or hydrophobic compound; toxin; auristatin; MMAE |
| $(CH_2)_{15}$ | — | —(C=O)—$CH_2$—$(CH_2$—O—$CH_2)_{1-24}$—$CH_2$— | Cleavable or non-cleavable linker; di- or tri- or oligo peptide; val-cit; or absent | Spacer system | Large, charged or hydrophobic compound; toxin; auristatin; MMAE |
| $(CH_2)_5$ | — | —(C=O)—$(CH_2)_{10-20}$— | Cleavable or non-cleavable linker; di- or tri- or oligo peptide; val-cit; or absent | Spacer system | Large, charged or hydrophobic compound; toxin; auristatin; MMAE |
| $(CH_2)_{10}$ | — | —(C=O)—$(CH_2)_{10-20}$— | Cleavable or non-cleavable linker; di- or tri- or oligo peptide; val-cit; or absent | Spacer system | Large, charged or hydrophobic compound; toxin; auristatin; MMAE |
| $(CH_2)_{15}$ | — | —(C=O)—$(CH_2)_{10-20}$— | Cleavable or non-cleavable linker; di- or tri- or oligo peptide; val-cit; or absent | Spacer system | Large, charged or hydrophobic compound; toxin; auristatin; MMAE |
| $(CH_2)_5$ | — | —$(CH_2)_{1-6}$— | Cleavable or non-cleavable linker; di- or tri- or oligo peptide; val-cit; or absent | Spacer system | Large, charged or hydrophobic compound; toxin; auristatin; MMAE |
| $(CH_2)_{10}$ | — | —$(CH_2)_{1-6}$— | Cleavable or non-cleavable linker; di- or tri- or oligo peptide; val-cit; or absent | Spacer system | Large, charged or hydrophobic compound; toxin; auristatin; MMAE |

TABLE 2-continued

| $C_n$ | X | L | V | Y | Z |
|---|---|---|---|---|---|
| $(CH_2)_{15}$ | — | $-(CH_2)_{1-6}-$ | Cleavable or non-cleavable linker; di- or tri- or oligo peptide; val-cit; or absent | Spacer system | Large, charged or hydrophobic compound; toxin; auristatin; MMAE |
| $(CH_2)_5$ | — | $-(CH_2)_{10-20}-$ | Cleavable or non-cleavable linker; di- or tri- or oligo peptide; val-cit; or absent | Spacer system | Large, charged or hydrophobic compound; toxin; auristatin; MMAE |
| $(CH_2)_{10}$ | — | $-(CH_2)_{10-20}-$ | Cleavable or non-cleavable linker; di- or tri- or oligo peptide; val-cit; or absent | Spacer system | Large, charged or hydrophobic compound; toxin; auristatin; MMAE |
| $(CH_2)_{15}$ | — | $-(CH_2)_{10-20}-$ | Cleavable or non-cleavable linker; di- or tri- or oligo peptide; val-cit; or absent | Spacer system | Large, charged or hydrophobic compound; toxin; auristatin; MMAE |
| $(CH_2)_5$ | — | $-(C=O)-O-CH_2-$ | Cleavable or non-cleavable linker; di- or tri- or oligo peptide; val-cit; or absent | Spacer system | Large, charged or hydrophobic compound; toxin; auristatin; MMAE |
| $(CH_2)_{10}$ | — | $-(C=O)-O-CH_2-$ | Cleavable or non-cleavable linker; di- or tri- or oligo peptide; val-cit; or absent | Spacer system | Large, charged or hydrophobic compound; toxin; auristatin; MMAE |
| $(CH_2)_{15}$ | — | $-(C=O)-O-CH_2-$ | Cleavable or non-cleavable linker; di- or tri- or oligo peptide; val-cit; or absent | Spacer system | Large, charged or hydrophobic compound; toxin; auristatin; MMAE |
| $(CH_2)_5$ | — | $-(C=O)-O-(CH_2)_{2-20}-$ | Cleavable or non-cleavable linker; di- or tri- or oligo peptide; val-cit; or absent | Spacer system | Large, charged or hydrophobic compound; toxin; auristatin; MMAE |
| $(CH_2)_{10}$ | — | $-(C=O)-O-(CH_2)_{2-20}-$ | Cleavable or non-cleavable linker; di- or tri- or oligo peptide; val-cit; or absent | Spacer system | Large, charged or hydrophobic compound; toxin; auristatin; MMAE |
| $(CH_2)_{15}$ | — | $-(C=O)-O-(CH_2)_{2-20}-$ | Cleavable or non-cleavable linker; di- or tri- or oligo peptide; val-cit; or absent | Spacer system | Large, charged or hydrophobic compound; toxin; auristatin; MMAE |
| $(CH_2)_5$ | — | Amino acid, di- or tri- or oligo peptide | Cleavable or non-cleavable linker; di- or tri- or oligo peptide; val-cit; or absent | Spacer system | Large, charged or hydrophobic compound; toxin; auristatin; MMAE |
| $(CH_2)_{10}$ | — | Amino acid, di- or tri- or oligo peptide | Cleavable or non-cleavable linker; di- or tri- or oligo peptide; val-cit; or absent | Spacer system | Large, charged or hydrophobic compound; toxin; auristatin; MMAE |
| $(CH_2)_{15}$ | — | Amino acid, di- or tri- or oligo peptide | Cleavable or non-cleavable linker; di- or tri- or oligo peptide; val-cit; or absent | Spacer system | Large, charged or hydrophobic compound; toxin; auristatin; MMAE |
| $(CH_2)_5$ | — | $-(C=O)-CH_2-S-$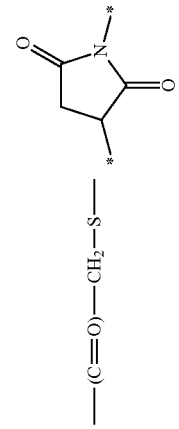 | Cleavable or non-cleavable linker; di- or tri- or oligo peptide; val-cit; or absent | Spacer system; $CH_2-(CH_2-O-CH_2)_4-CH_2-$ | Large, charged or hydrophobic compound; toxin; auristatin; MMAE |

TABLE 2-continued

| $C_n$ | X | L | V | Y | Z |
|---|---|---|---|---|---|
| (CH$_2$)$_5$ | — | —(C=O)—CH$_5$—S—[succinimide] | Cleavable or non-cleavable linker; di- or tri- or oligo peptide; val-cit; or absent | Spacer system; CH$_2$—(CH$_2$—O—CH$_2$)$_4$—CH$_2$— | Large, charged or hydrophobic compound; toxin; auristatin; MMAE |
| (CH$_2$)$_5$ | — | —CH$_2$—(CH$_2$—O—CH$_2$)$_{1-24}$—CH$_2$—S—[succinimide] | Cleavable or non-cleavable linker; di- or tri- or oligo peptide; val-cit; or absent | Spacer system; CH$_2$—(CH$_2$—O—CH$_2$)$_4$—CH$_2$— | Large, charged or hydrophobic compound; toxin; auristatin; MMAE |
| —CH$_2$—(CH$_2$—O—CH$_2$)$_3$—CH$_2$— | — | — | Cleavable or non-cleavable linker; di- or tri- or oligo peptide; val-cit; or absent | Spacer system | Large, charged or hydrophobic compound; toxin; auristatin; MMAE |
| —CH$_2$—(CH$_2$—O—CH$_2$)$_3$—CH$_2$— | — | —CH$_2$—(CH$_2$—O—CH$_2$)$_{1-24}$—CH$_2$— | Cleavable or non-cleavable linker; di- or tri- or oligo peptide; val-cit; or absent | Spacer system | Large, charged or hydrophobic compound; toxin; auristatin; MMAE |
| —CH$_2$—(CH$_2$—O—CH$_2$)$_3$—CH$_2$— | — | —(C=O)—CH$_2$—(CH$_2$—O—CH$_2$)$_{1-24}$—CH$_2$— | Cleavable or non-cleavable linker; di- or tri- or oligo peptide; val-cit; or absent | Spacer system | Large, charged or hydrophobic compound; toxin; auristatin; MMAE |
| —O—(CH$_2$)$_{1-5}$ | — | — | Cleavable or non-cleavable linker; di- or tri- or oligo peptide; val-cit; or absent | Spacer system | Large, charged or hydrophobic compound; toxin; auristatin; MMAE |
| —O—CH$_2$—(CH$_2$—O—CH$_2$)$_3$—CH$_2$— | — | —CH$_2$—(CH$_2$—O—CH$_2$)$_{1-24}$—CH$_2$— | Cleavable or non-cleavable linker; di- or tri- or oligo peptide; val-cit; or absent | Spacer system | Large, charged or hydrophobic compound; toxin; auristatin; MMAE |
| —O—CH$_2$—(CH$_2$—O—CH$_2$)$_3$—CH$_2$— | — | —(C=O)—CH$_2$—(CH$_2$—O—CH$_2$)$_{1-24}$—CH$_2$— | Cleavable or non-cleavable linker; di- or tri- or oligo peptide; val-cit; or absent | Spacer system | Large, charged or hydrophobic compound; toxin; auristatin; MMAE |
| (CH$_2$)$_4$—CH(NH$_2$)—(C=O)— | — | — | — | Spacer system | Charged compound |
| (CH$_2$)$_4$—CH(NH$_2$)—(C=O)— | — | — | di- or tri- or oligo peptide; val-cit | Spacer system | Large, charged or hydrophobic compound; toxin; auristatin; MMAE |
| (CH$_2$)$_4$—CH(NH$_2$)—(C=O)— | — | —(CH$_2$)$_{1-6}$— | Cleavable or non-cleavable linker; di- or tri- or oligo peptide; val-cit; or absent | Spacer system | Large, charged or hydrophobic compound; toxin; auristatin; MMAE |
| (CH$_2$)$_4$—CH(NH$_2$)—(C=O)— | — | —(CH$_2$)$_5$— | Cleavable or non-cleavable linker; di- or tri- or oligo peptide; val-cit; or absent | Spacer system | Large, charged or hydrophobic compound; toxin; auristatin; MMAE |
| (CH$_2$)$_4$—CH(NH$_2$)—(C=O)— | — | —CH$_2$—(CH$_2$—O—CH$_2$)$_{1-24}$—CH$_2$— | Cleavable or non-cleavable linker; di- or tri- or oligo | Spacer system | Large, charged or hydrophobic compound; |

TABLE 2-continued

| $C_n$ | X | L | V | Y | Z |
|---|---|---|---|---|---|
| $(CH_2)_5$ | — | — | peptide; val-cit; or absent | Spacer system; $(CH_2)_5$ | Large, charged or hydrophobic compound; toxin; auristatin; MMAE |
| $(CH_2)_{6-10}$ | — | — | — | Spacer system; $(CH_2)_5$ | Large, charged or hydrophobic compound; toxin; auristatin; MMAF |
| $(CH_2)_{15}$ | — | — | — | Spacer system; $(CH_2)_5$ | Large, charged or hydrophobic compound; toxin; auristatin; MMAF |
| $-CH_2-(CH_2-O-CH_2)_3-CH_2-$ | — | — | — | Spacer system; $(CH_2)_5$ | Large, charged or hydrophobic compound; toxin; auristatin; MMAF |
| $(CH_2)_5$ | — | $-(C=O)-CH_2-$ | — | Spacer system; $(CH_2)_5$ | Large, charged or hydrophobic compound; toxin; auristatin; MMAF |
| $(CH_2)_5$ | — | $-(C=O)-(CH_2)_5-$ | — | Spacer system; $(CH_2)_5$ | Large, charged or hydrophobic compound; toxin; auristatin; MMAF |
| $(CH_2)_5$ | — | $-CH_2-(CH_2-O-CH_2)_{1-24}-CH_2-$ | — | Spacer system; $(CH_2)_5$ | Large, charged or hydrophobic compound; toxin; auristatin; MMAF |
| $-O-(CH_2)_{1-5}$ | — | $-CH_2-(CH_2-O-CH_2)_{1-24}-CH_2-$ | — | Spacer system; $(CH_2)_5$ | Large, charged or hydrophobic compound; toxin; auristatin; MMAF |
| $-O-CH_2-(CH_2-O-CH_2)_3-CH_2-$ | — | $-CH_2-(CH_2-O-CH_2)_{1-24}-CH_2-$ | — | Spacer system; $(CH_2)_5$ | Large, charged or hydrophobic compound; toxin; auristatin; MMAF |
| $-O-CH_2-(CH_2-O-CH_2)_3-CH_2-$ | — | $-(C=O)-CH_2-$ | — | Spacer system; $(CH_2)_5$ | Large, charged or hydrophobic compound; toxin; auristatin; MMAF |
| $-O-CH_2-(CH_2-O-CH_2)_3-CH_2-$ | — | $-(C=O)-(CH_2)_5-$ | — | Spacer system; $(CH_2)_5$ | Large, charged or hydrophobic compound; toxin; auristatin; MMAF |
| $-CH_2-(CH_2-O-CH_2)_3-CH_2-$ | — | $-CH_2-(CH_2-O-CH_2)_{1-24}-CH_2-$ | — | Spacer system; $(CH_2)_5$ | Large, charged or hydrophobic compound; toxin; auristatin; MMAF |
| $(CH_2)_5$ | — | — | Non-cleavable linker; $(CH_2)_5$ | — | Large, charged or hydrophobic compound; toxin; auristatin; MMAF |
| $(CH_2)_{6-10}$ | — | — | Non-cleavable linker; $(CH_2)_5$ | — | Large, charged or hydrophobic compound; toxin; auristatin; MMAF |
| $(CH_2)_{15}$ | — | — | Non-cleavable linker; $(CH_2)_5$ | — | Large, charged or hydrophobic compound; toxin; auristatin; MMAF |
| $-CH_2-(CH_2-O-CH_2)_3-CH_2-$ | — | — | Non-cleavable linker; $(CH_2)_5$ | — | Large, charged or hydrophobic compound; toxin; auristatin; MMAF |
| $(CH_2)_5$ | — | $-(C=O)-CH_2-$ | — | — | Large, charged or hydrophobic compound; |

TABLE 2-continued

| $(C)_n$ | X | L | V | Y | Z |
|---|---|---|---|---|---|
| $(CH_2)_5$ | — | —(C=O)—$(CH_2)_5$— | Non-cleavable linker; $(CH_2)_5$ | — | Large, charged or hydrophobic compound; toxin; auristatin; MMAF |
| $(CH_2)_5$ | — | —(C=O)—$(CH_2)_5$— | Non-cleavable linker; $(CH_2)_5$ | — | Large, charged or hydrophobic compound; toxin; auristatin; MMAF |
| $(CH_2)_5$ | — | —(C=O)—$(CH_2)_5$— | Non-cleavable linker; $(CH_2)_5$ | — | Large, charged or hydrophobic compound; toxin; auristatin; MMAF |
| $(CH_2)_5$ | — | —$CH_2$—$(CH_2$—O—$CH_2)_{1-24}$—$CH_2$— | Non-cleavable linker; $(CH_2)_5$ | — | Large, charged or hydrophobic compound; toxin; auristatin; MMAF |
| —O—$(CH_2)_{1-5}$ | — | —$CH_2$—$(CH_2$—O—$CH_2)_{1-24}$—$CH_2$— | Non-cleavable linker; $(CH_2)_5$ | — | Large, charged or hydrophobic compound; toxin; auristatin; MMAF |
| —O—$CH_2$—$(CH_2$—O—$CH_2)_3$—$CH_2$— | — | —$CH_2$—$(CH_2$—O—$CH_2)_{1-24}$—$CH_2$— | Non-cleavable linker; $(CH_2)_5$ | — | Large, charged or hydrophobic compound; toxin; auristatin; MMAF |
| —O—$CH_2$—$(CH_2$—O—$CH_2)_3$—$CH_2$— | — | —(C=O)—$CH_2$— | Non-cleavable linker; $(CH_2)_5$ | — | Large, charged or hydrophobic compound; toxin; auristatin; MMAF |
| —O—$CH_2$—$(CH_2$—O—$CH_2)_3$—$CH_2$— | — | —(C=O)—$(CH_2)_5$— | Non-cleavable linker; $(CH_2)_5$ | — | Large, charged or hydrophobic compound; toxin; auristatin; MMAF |
| —$CH_2$—$(CH_2$—O—$CH_2)_3$—$CH_2$— | — | —$CH_2$—$(CH_2$—O—$CH_2)_{1-24}$—$CH_2$— | Non-cleavable linker; $(CH_2)_5$ | — | Large, charged or hydrophobic compound; toxin; auristatin; MMAF |

TABLE 3

| Structure of Formula Ib | (C)ₙ | X | L | V | Y | R |
|---|---|---|---|---|---|---|
| H₂N-(CH₂)₅-NH-C(=O)-CH₂-SH | (CH₂)₅ | NH | —(C=O)—CH₂— | — | — | SH |
| H₂N-CH(-)-C(=O)-NH-(CH₂)₅-SH (lysine-based with SH) | (CH₂)₄—CH(NH₂)—(C=O)— | — | —CH₂— | — | — | SH |
| H₂N-(CH₂)₅-NH-C(=O)-(CH₂)₅-SH | (CH₂)₅ | NH | —(C=O)—(CH₂)₅— | — | — | SH |
| H₂N-(CH₂)₅-NH-C(=O)-CH₂-(O-CH₂-CH₂)₃-O-CH₂-SH | (CH₂)₅<br>(CH₂)₄—CH(NH₂)—(C=O)—<br>O—(CH₂)₅<br>O—(CH₂)₅ | NH<br>—<br>NH<br>NH | —(CH₂)₅—<br>—(CH₂)₅—<br>—(C=O)—(CH₂)₅—<br>—(C=O)—(CH₂)₁₀— | —<br>—<br>—<br>— | —<br>—<br>—<br>— | SH<br>SH<br>SH<br>SH |
| (PEG-thiol structure) | (CH₂)₅ | NH | —(C=O)—CH₂—(CH₂—O—CH₂)₄—CH₂— | — | — | SH |
| | (CH₂)₅<br>(CH₂)₅<br>O—(CH₂)₅ | NH<br>NH<br>NH | —(C=O)—CH₂—(CH₂—O—CH₂)₁₋₂₄—CH₂—<br>—CH₂—(CH₂—O—CH₂)₁₋₂₄—CH₂—<br>—(C=O)—CH₂—(CH₂—O—CH₂)₁₋₂₄—CH₂— | —<br>—<br>— | —<br>—<br>— | SH<br>SH<br>SH |
| H₂N-(CH₂)₅-N₃ | —CH₂—(CH₂—O—CH₂)₃—CH₂— | — | — | — | — | N₃ |
| (PEG-azide structure) | (CH₂)₅ | NH | —(C=O)—CH₂—(CH₂—O—CH₂)₄—CH₂— | — | — | N₃ |
| | —CH₂—(CH₂—O—CH₂)₁₋₆—CH₂— | — | — | — | — | N₃ |
| | (CH₂)₅<br>O—(CH₂)₅ | NH<br>NH | —(C=O)—CH₂—(CH₂—O—CH₂)₁₋₂₄—CH₂—<br>—(C=O)—CH₂—(CH₂—O—CH₂)₁₋₂₄—CH₂— | —<br>— | —<br>— | N₃<br>N₃ |
| (methyl benzoate with PPh₂ and amide linker to H₂N-(CH₂)₅-NH-) | (CH₂)₅ | NH | —(C=O)— | — | — | (methyl 2-(diphenylphosphino)benzoate group) |

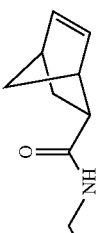

TABLE 3-continued

| Structure of Formula Ib | (C)$_n$ | X L | V Y | R |
|---|---|---|---|---|
| | (CH$_2$)$_5$ | NH—(C=O)—(CH$_2$)$_5$— | — — | maleimide |
| | (CH$_2$)$_5$ | NH—(CH$_2$)$_5$— | — — | maleimide |
| | (CH$_2$)$_4$—CH(NH$_2$)—(C=O)— | —CH$_2$— | — — | maleimide |
| | O—(CH$_2$)$_5$ | NH—(C=O)—(CH$_2$)$_5$— | — — | maleimide |
| | (CH$_2$)$_5$ | NH—(C=O)—(CH$_2$)$_5$— | — — | DBCO-carbonyl |

TABLE 3-continued
| Structure of Formula Ib | $(C)_n$ | X | L | V | Y | R |
|---|---|---|---|---|---|---|
| | $(CH_2)_5$ | NH | $-(CH_2)_5-$ | — | — |  |
| | $(CH_2)_4-CH(NH_2)-(C=O)-$ | | $-CH_2-$ | — | — | 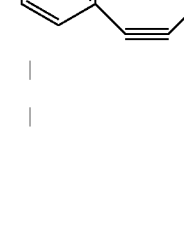 |
| | $O-(CH_2)_5$ | NH | $-(C=O)-(CH_2)_5-$ | — | — |  |
| | $-CH_2-(CH_2-O-CH_2)_4-CH_2-$ | | — | — | — | 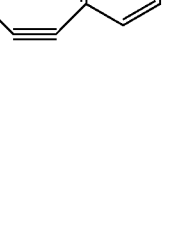 |

TABLE 3-continued
| Structure of Formula Ib | (C)$_n$ | X | L | V | Y | R |
|---|---|---|---|---|---|---|
| | (CH$_2$)$_5$ | NH | —(CH$_2$)$_2$— | — | — |  |
| | (CH$_2$)$_5$ | NH | —(C=O)—(CH$_2$)$_5$— | — | — |  |
| | (CH$_2$)$_5$ | NH | —(CH$_2$)$_5$— | — | — |  |
| | (CH$_2$)$_4$—CH(NH$_2$)—(C=O)— | | —CH$_2$— | — | — |  |
| | O—(CH$_2$)$_5$ | NH | —(C=O)—CH$_2$— | — | — |  |
| | —CH$_2$—(CH$_2$—O—CH$_2$)$_3$—CH$_2$— | | — | — | — |  |

TABLE 4

| of Formula III | R' | L' | V' | Y' | Z |
|---|---|---|---|---|---|
| (structure: maleimide-(CH₂)₅-C(=O)-Val_Cit_PAB_MMAE) | maleimide | —(CH₂)₅—(C=O)— | Val-cit | PAB | MMAE |
| | maleimide | —CH₂—(CH₂—O—CH₂)₄—CH₂—(C=O)— | Val-cit | PAB | MMAE |
| (structure: DBCO-amide-PEG-C(=O)-Val_Cit_PAB_MMAE) | DBCO | —(C=O)—CH₂)₄—(C=O)—NH—CH₂—(CH₂—O—CH₂)₄—CH₂—(C=O)— | Val-cit | PAB | MMAE |
| | DBCO | —(C=O)—CH₂)₄—(C=O)—NH—CH₂—(CH₂—O—CH₂)₄—CH₂—(C=O)— | — | — | MMAF |
| (structure: alkyne-(CH₂)₅-C(=O)-Val_Cit_PAB_MMAE) | alkyne | —(CH₂)₅—(C=O)— | Val-cit | PAB | MMAE |

TABLE 4-continued

| of Formula III | R' | L' | V' | Y' | Z |
|---|---|---|---|---|---|
| | ⇉ | —CH$_2$—(CH$_2$—O—CH$_2$)$_4$—CH$_2$—(C=O)— | Val-cit | PAB | MMAE |
| | ⇉ | —CH$_2$—(CH$_2$—O—CH$_2$)$_4$—CH$_2$—(C=O)— | — | — | MMAF |
| | N$_3$ | —(CH$_2$)$_5$—(C=O)— | Val-cit | PAB | MMAE |
| | N$_3$ | —CH$_2$—(CH$_2$—O—CH$_2$)$_4$—CH$_2$—(C=O)— | Val-cit | PAB | MMAE |
| | N$_3$ | —CH$_2$—(CH$_2$—O—CH$_2$)$_4$—CH$_2$—(C=O)— | — | — | MMAF |
| N$_3$∼∼∼∼C(=O)−Val_Cit_PAB_MMAE | | | | | |

TABLE 5
Compound of Formula 1b
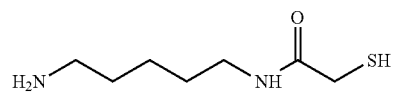
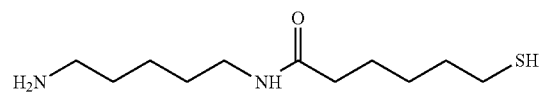 [SMILES: NCCCCCNC(=O)CCCCCS]
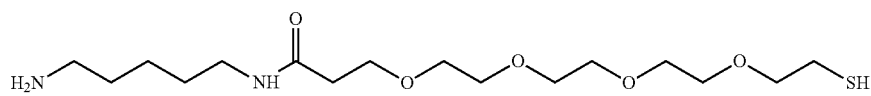
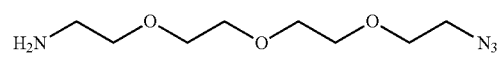
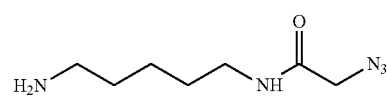
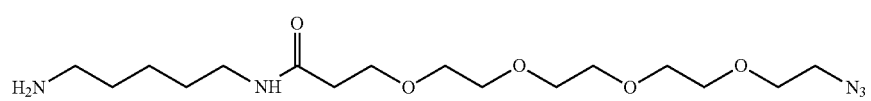 [SMILES: [N-]=[N+]=NCCOCCOCCOCCOCCC(=O)NCCCCCN]
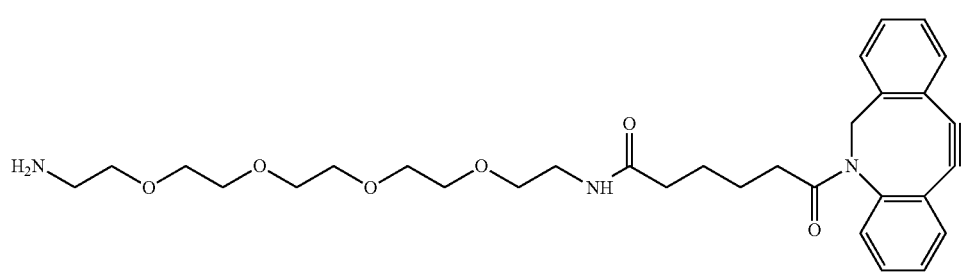 [SMILES: NCCOCCOCCOCCOCCNC(=O)CCCCC(=O)N1Cc2ccccc2C#Cc2ccccc21]
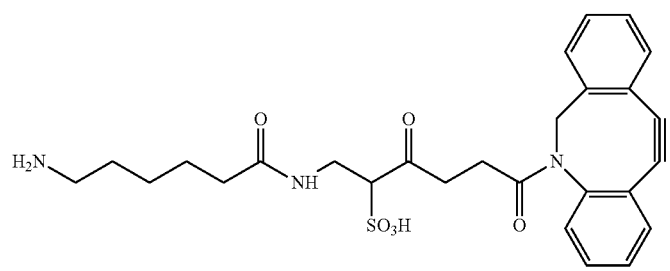 [SMILES: NCCCCCC(=O)NCC(C(=O)CCC(=O)N1Cc2ccccc2C#Cc2ccccc21)S(=O)(=O)O]
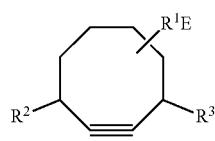
(Formula B)
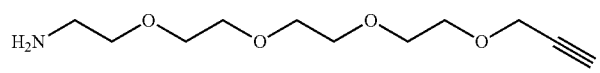 [SMILES: C#CCOCCOCCOCCOCCN]
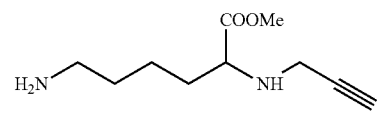

TABLE 5-continued
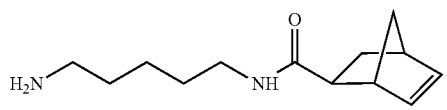 [SMILES: NCCCCCNC(=O)C1CC2C=CC1C2]
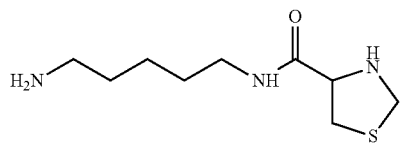 [SMILES: NCCCCCNC(=O)C1CSCN1]
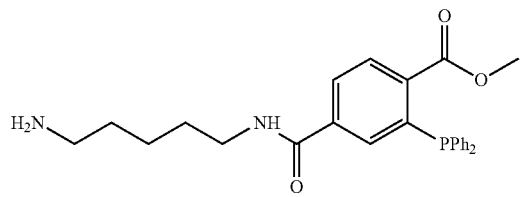
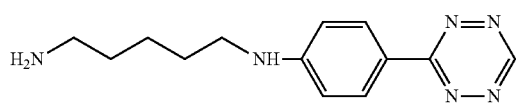
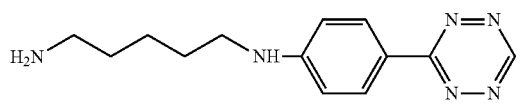
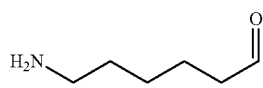
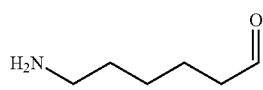
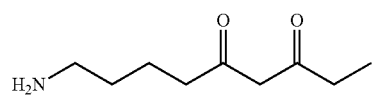
Compound of Formula III
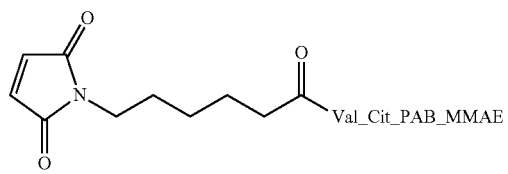
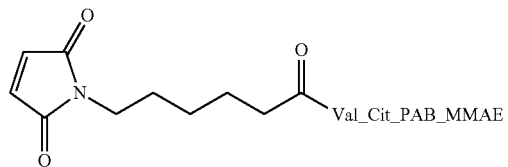
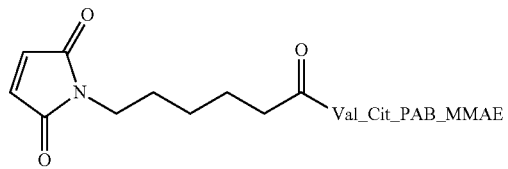

TABLE 5-continued
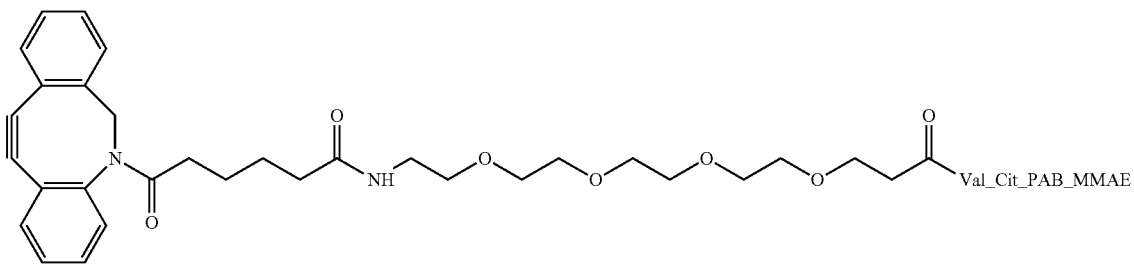
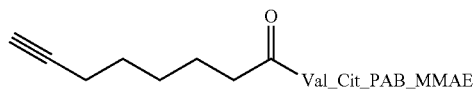
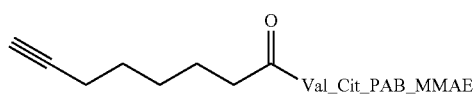
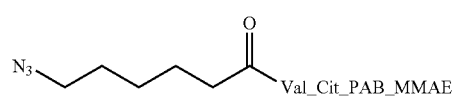
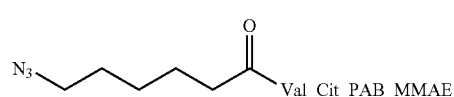
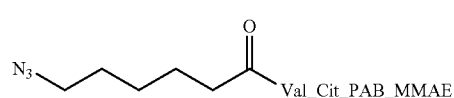
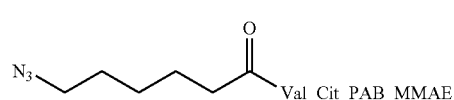
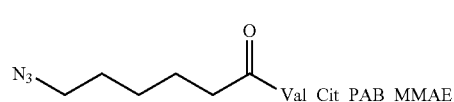
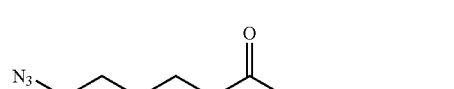
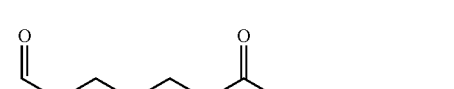
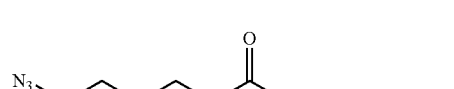
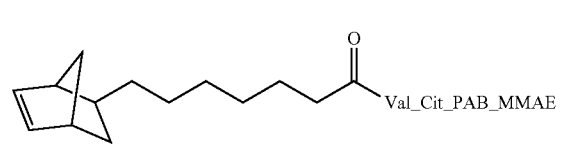
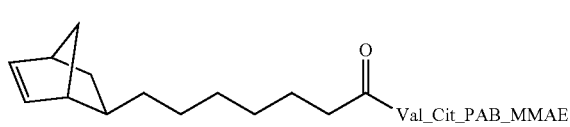

TABLE 5-continued

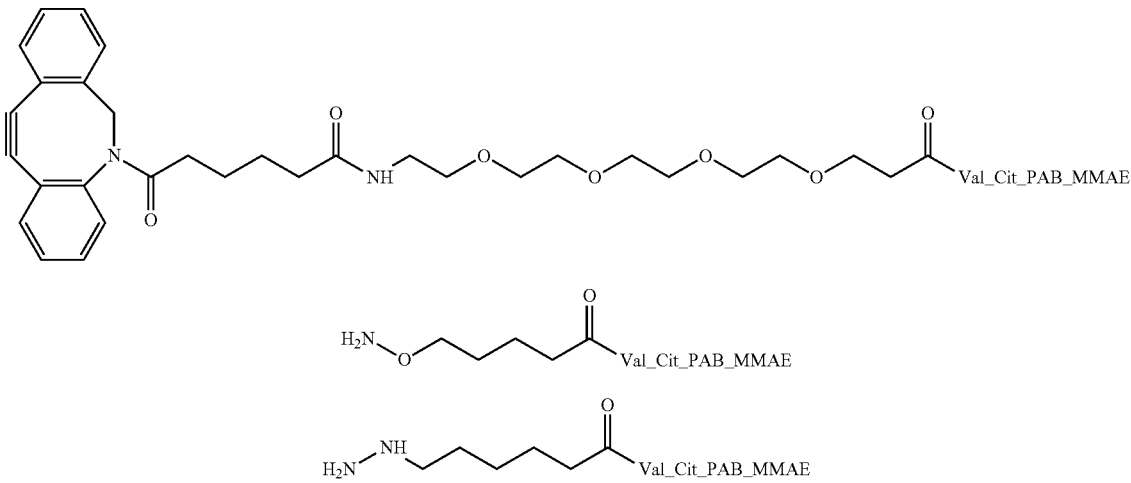

All headings and sub-headings are used herein for convenience only and should not be construed as limiting the invention in any way. Any combination of the above-described elements in all possible variations thereof is encompassed by the invention unless otherwise indicated herein or otherwise clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e. g., all exact exemplary values provided with respect to a particular factor or measurement can be considered to also provide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents, The description herein of any aspect or embodiment of the invention using terms such as reference to an element or elements is intended to provide support for a similar aspect or embodiment of the invention that "consists of"," "consists essentially of" or "substantially comprises" that particular element or elements, unless otherwise stated or clearly contradicted by context (e. g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

All publications and patent applications cited in this specification are herein incorporated by reference in their entireties as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

The invention claimed is:

1. A method for producing an antibody conjugated to a moiety of interest, comprising:
    a) providing a composition comprising a plurality of antibodies each comprising an acceptor glutamine residue; and
    b) reacting said antibody comprising an acceptor glutamine residue with a linking reagent comprising a primary amine and a moiety of interest, under suitable conditions, in the presence of an amount of bacterial transglutaminase (BTG) providing between 0.004 and 0.03 enzyme units (U), as determined by a hydroxamate activity assay, per nanomole (nmole) of acceptor glutamine, to obtain a composition comprising a plurality of antibodies comprising an acceptor glutamine residue linked to the linking reagent, wherein no more than 10% of the antibodies in the composition comprise a deamidated acceptor glutamine residue, and wherein the moiety of interest is selected from the group consisting of a hydrophobic organic compound, an organic compound having an electrically negative charge, an organic compound having a molecular weight of at least 400 g/mol, and any combination thereof.

2. The method of claim 1, wherein the moiety of interest has a molecular weight of at least 800 g/mol.

3. The method of claim 1, wherein the BTG is present in an amount providing less than about 0.06 U/nmole per nanomole of antibody, wherein the antibody has two acceptor glutamines.

4. The method of claim 1, wherein the BTG is present in an amount providing less than about 0.075 U/nmole of antibody, wherein the antibody has four acceptor glutamines.

5. The method of claim 1, wherein the linking reagent is provided in an amount which is between about 2 and about 15 molar equivalents per acceptor glutamine present on the antibody.

6. The method of claim 1, wherein the antibody comprising an acceptor glutamine residue is provided at a concentration of between about 0.01 mg/mL and about 10 mg/mL.

7. The method of claim 1, wherein the BTG enzyme is provided at a concentration of between 0.1 U/ml and about 5 U/ml.

8. The method of claim 1, wherein the antibody comprises an acceptor amino acid residue within a constant region.

9. The method of claim 1, wherein the acceptor amino acid residue is an acceptor glutamine naturally present in an Fc region.

10. The method of claim 9, wherein the acceptor amino acid residue is an acceptor glutamine naturally present in a CH2 or CH3 domain.

11. The method of claim 9, wherein the acceptor amino acid residue is an acceptor glutamine naturally present at residue 295 according to Kabat numbering.

12. The method of claim 1, wherein no more than 5% of the antibodies in the composition comprise a deamidated acceptor glutamine residue.

13. The method of claim 12, wherein no more than 2% of the antibodies in the composition comprise a deamidated acceptor glutamine residue.

14. A vessel comprising:
(a) a plurality of antibodies each comprising an acceptor glutamine residue, wherein no more than 10% of the antibodies comprise a deamidated acceptor glutamine residue;
(b) a linking reagent comprising a primary amine and a moiety of interest selected from the group consisting of a hydrophobic organic compound, an organic compound having an electrically negative charge, an organic compounds having a molecular weight of at least 400 g/mol, and any combination thereof; and
(c) a bacterial transglutaminase (BTG) in the amount of between 0.004 and 0.03 enzyme units (U), as determined by a hydroxamate activity assay, per nanomole (nmole) of acceptor glutamine.

15. The vessel of claim 14, wherein the moiety of interest is an organic compound that has a molecular weight of at least 800 g/mol.

16. The vessel of claim 14, wherein the antibody has four acceptor glutamines and the amount of BTG is less than about 0.075 U/nmole of antibody.

17. The vessel of claim 14, wherein the antibody has two acceptor glutamines and the amount of BTG is less than about 0.06 U/nmole of antibody.

18. The vessel of claim 14, wherein the antibody is a tetrameric antibody comprising two Ig heavy chains having Fc regions and two Ig light chains.

19. The vessel of claim 18, wherein the acceptor glutamine is within a constant region of the antibody.

20. The vessel of claim 19, wherein the constant region is the Fc region.

21. The vessel of claim 20, wherein the antibody comprises one acceptor glutamine on each heavy chain.

22. The vessel of claim 20, wherein the antibody comprises two acceptor glutamines on each heavy chain.

23. The vessel of claim 19, wherein the acceptor glutamine is naturally present in a CH2 or CH3 domain.

24. The vessel of claim 19 wherein the acceptor glutamine is naturally present at residue 295 according to Kabat numbering.

25. The vessel of claim 14, wherein the linking reagent is provided in an amount which is between about 2 and about 15 molar equivalents per acceptor glutamine present on the antibody.

26. The vessel of claim 14, wherein the antibody is provided at a concentration of between about 0.01 mg/ml and about 10 mg/ml.

27. The vessel of claim 14, wherein the BTG enzyme is provided at a concentration of between about 0.1 U/ml and about 5 U/ml.

* * * * *